(12) United States Patent  
Motadel

(10) Patent No.: US 8,590,736 B2
(45) Date of Patent: Nov. 26, 2013

(54) AUTOMATED PIPETTE TIP LOADING DEVICES AND METHODS

(75) Inventor: Arta Motadel, San Diego, CA (US)

(73) Assignee: Biotix, Inc., San Diego, CA (US)

( * ) Notice: Subject to any disclaimer, the term of this patent is extended or adjusted under 35 U.S.C. 154(b) by 288 days.

(21) Appl. No.: 12/757,851

(22) Filed: Apr. 9, 2010

(65) Prior Publication Data

US 2010/0258578 A1    Oct. 14, 2010

Related U.S. Application Data

(60) Provisional application No. 61/168,561, filed on Apr. 11, 2009, provisional application No. 61/250,404, filed on Oct. 9, 2009.

(51) Int. Cl.
*B65D 83/02*    (2006.01)

(52) U.S. Cl.
USPC ............... 221/92; 221/93; 221/95; 221/104

(58) Field of Classification Search
USPC ............ 221/92–93, 103–104, 107, 111, 119
See application file for complete search history.

(56) References Cited

U.S. PATENT DOCUMENTS

| | | | |
|---|---|---|---|
| 2,134,908 A | 11/1938 | Copeman | |
| 2,645,245 A | 7/1953 | Maisch | |
| 3,214,831 A | 11/1965 | Shellman et al. | |
| 3,853,217 A | 12/1974 | Scordato et al. | |
| 3,937,322 A | 2/1976 | Cohen | |
| D246,466 S | 11/1977 | Attree et al. | |
| D264,810 S | 6/1982 | Voltmann | |
| D271,239 S | 11/1983 | Lemieux et al. | |
| D276,071 S | 10/1984 | Malinoff | |
| D283,162 S | 3/1986 | Godsey | |
| D302,207 S | 7/1989 | Matkovich | |
| 5,048,957 A | 9/1991 | Berthold et al. | |
| D323,400 S | 1/1992 | Frenkel et al. | |
| 5,092,184 A * | 3/1992 | Goodell et al. | ............ 73/863.32 |
| 5,156,811 A | 10/1992 | White | |
| D337,165 S | 7/1993 | Malinoff | |
| 5,324,482 A * | 6/1994 | Scaramella et al. | .......... 422/526 |
| D349,773 S | 8/1994 | Malin et al. | |
| 5,392,914 A * | 2/1995 | Lemieux et al. | ............. 206/499 |
| 5,426,911 A | 6/1995 | Poplin et al. | |

(Continued)

FOREIGN PATENT DOCUMENTS

| | | |
|---|---|---|
| JP | 08-503911 | 4/1996 |
| JP | 2000-084419 | 3/2000 |

(Continued)

OTHER PUBLICATIONS

International Search Report and Written Opinion mailed on: Nov. 26, 2010 in International Application No. PCT/US2010/030611 filed on Apr. 9, 2010 and published as: WO 2010/118374 on: Oct. 14, 2010.
Office Action mailed on: May 24, 2011 in U.S. Appl. No. 12/577,003, filed Oct. 9, 2009, and published as 2010/0089938 on Apr. 15, 2010.
Office Action mailed on: Apr. 7, 2011 in U.S. Appl. No. 12/577,003, filed Oct. 9, 2009, and published as 2010/0089938 on Apr. 15, 2010.

(Continued)

*Primary Examiner* — Michael K Collins
(74) *Attorney, Agent, or Firm* — Grant Anderson LLP

(57) ABSTRACT

Discussed herein are methods and devices for storing, handling, loading or dispensing of pipette tips. Some embodiments allow repetitive loading of an array of multiple pipette tips that are stored in a nested configuration.

22 Claims, 34 Drawing Sheets

(56) References Cited

U.S. PATENT DOCUMENTS

| | | | |
|---|---|---|---|
| 5,441,702 A * | 8/1995 | Lemieux et al. | 422/526 |
| 5,487,872 A | 1/1996 | Hafeman et al. | |
| 5,487,997 A | 1/1996 | Stolop | |
| 5,588,792 A | 12/1996 | Tiso | |
| 5,642,816 A * | 7/1997 | Kelly et al. | 211/60.1 |
| 5,779,984 A | 7/1998 | Kelly et al. | |
| 5,789,251 A | 8/1998 | Astle | |
| 5,915,284 A | 6/1999 | Metler et al. | |
| D414,271 S | 9/1999 | Mendoza | |
| 6,007,779 A * | 12/1999 | Lemieux et al. | 422/526 |
| D420,139 S | 2/2000 | Ballin et al. | |
| D420,142 S | 2/2000 | Ballin et al. | |
| D420,743 S | 2/2000 | Monks | |
| 6,019,225 A | 2/2000 | Kalmakis et al. | |
| 6,054,099 A | 4/2000 | Levy | |
| 6,116,099 A * | 9/2000 | Carl | 73/864.14 |
| 6,182,719 B1 * | 2/2001 | Yahiro | 141/130 |
| D441,091 S | 4/2001 | Day | |
| 6,258,324 B1 * | 7/2001 | Yiu | 422/526 |
| 6,286,678 B1 * | 9/2001 | Petrek | 206/443 |
| 6,361,744 B1 | 3/2002 | Levy | |
| 6,419,086 B1 | 7/2002 | Vecchio | |
| D463,031 S | 9/2002 | Slomski et al. | |
| D463,863 S | 10/2002 | Carlson et al. | |
| D464,734 S | 10/2002 | Bema et al. | |
| D466,219 S | 11/2002 | Wynschenk et al. | |
| D469,544 S | 1/2003 | Lafond et al. | |
| 6,534,015 B1 | 3/2003 | Viot et al. | |
| D474,274 S | 5/2003 | Walters | |
| D477,416 S | 7/2003 | Roberts et al. | |
| 6,589,483 B1 * | 7/2003 | Maeda | 422/525 |
| 6,640,981 B2 | 11/2003 | Lafond et al. | |
| 6,752,967 B2 | 6/2004 | Farina et al. | |
| D492,792 S | 7/2004 | Kokaisel et al. | |
| 6,759,012 B2 | 7/2004 | Haslam et al. | |
| 6,793,891 B2 * | 9/2004 | Yiu | 422/525 |
| 6,830,732 B1 | 12/2004 | Hoffman et al. | |
| 6,875,405 B1 | 4/2005 | Mathus et al. | |
| 6,982,063 B2 * | 1/2006 | Hamel et al. | 422/511 |
| 7,105,129 B2 * | 9/2006 | Ruddock | 422/63 |
| D529,622 S | 10/2006 | Hadjis et al. | |
| D533,948 S | 12/2006 | Schaub et al. | |
| 7,169,361 B2 * | 1/2007 | Arnold et al. | 422/526 |
| 7,220,590 B2 | 5/2007 | Moritz et al. | |
| D556,338 S | 11/2007 | Coulling et al. | |
| D556,339 S | 11/2007 | Coulling et al. | |
| 7,309,469 B2 | 12/2007 | Anderson et al. | |
| D562,463 S | 2/2008 | Berndt et al. | |
| 7,335,337 B1 | 2/2008 | Smith | |
| D574,505 S | 8/2008 | Muller-Cohn et al. | |
| D574,506 S | 8/2008 | Monks | |
| D576,208 S | 9/2008 | Quercetti | |
| D598,127 S | 8/2009 | Lea | |
| D598,128 S | 8/2009 | Pihl et al. | |
| 7,585,463 B2 * | 9/2009 | Austin et al. | 422/63 |
| D601,713 S | 10/2009 | Lohn et al. | |
| D601,714 S | 10/2009 | Lohn et al. | |
| D608,013 S | 1/2010 | Coulling et al. | |
| D610,265 S | 2/2010 | Lea | |
| D620,605 S | 7/2010 | Reitze | |
| D624,196 S | 9/2010 | Himmelsbach et al. | |
| D624,660 S | 9/2010 | Himmelsbach et al. | |
| D624,661 S | 9/2010 | Himmelsbach et al. | |
| 7,820,115 B2 | 10/2010 | Zatechka et al. | |
| D628,306 S | 11/2010 | Blanc et al. | |
| D632,803 S | 2/2011 | Motadel et al. | |
| 7,892,504 B2 | 2/2011 | Taike et al. | |
| D638,138 S | 5/2011 | Wong | |
| D638,953 S | 5/2011 | Cavada et al. | |
| D645,156 S | 9/2011 | Reitze | |
| 2001/0046437 A1 * | 11/2001 | Bramwell et al. | 414/796.7 |
| 2003/0026738 A1 * | 2/2003 | Everett | 422/102 |
| 2003/0129089 A1 | 7/2003 | Arnold et al. | |
| 2004/0170534 A1 | 9/2004 | Brophy et al. | |
| 2004/0231438 A1 * | 11/2004 | Schwartz | 73/864.17 |
| 2005/0150808 A1 | 7/2005 | Sarna et al. | |
| 2006/0153736 A1 * | 7/2006 | Kalra et al. | 422/57 |
| 2007/0017870 A1 | 1/2007 | Belov et al. | |
| 2009/0092520 A1 | 4/2009 | Moulton | |
| 2009/0095091 A1 | 4/2009 | Smith | |
| 2009/0155123 A1 | 6/2009 | Williams et al. | |
| 2009/0255949 A1 | 10/2009 | Motadel | |
| 2010/0080734 A1 | 4/2010 | Brophy et al. | |
| 2010/0089938 A1 | 4/2010 | Motadel | |
| 2010/0258578 A1 | 10/2010 | Motadel | |
| 2010/0266457 A1 | 10/2010 | Rethwisch et al. | |
| 2011/0076205 A1 | 3/2011 | Kelly et al. | |

FOREIGN PATENT DOCUMENTS

| | | |
|---|---|---|
| JP | 2000-506064 | 5/2000 |
| JP | 2002-526242 | 8/2002 |
| JP | 2002-537966 | 11/2002 |
| JP | 2005-515942 | 2/2005 |
| KR | 10-2002-0092768 | 12/2002 |
| WO | WO 95/33563 | 12/1995 |
| WO | WO 98/45041 | 10/1998 |
| WO | WO 01/10556 | 2/2001 |
| WO | WO 02/45857 | 6/2002 |
| WO | WO 03/043739 | 5/2003 |
| WO | WO 2009/126945 | 10/2009 |
| WO | WO 2010/118374 | 10/2010 |

OTHER PUBLICATIONS

International Preliminary Report on Patentability mailed on: Oct. 21, 2010 in International Application No. PCT/US2009/040289 filed on Apr. 11, 2009 and published as: WO 09/126945 on: Oct. 15, 2009.

International Search Report and Written Opinion mailed on: Oct. 29, 2009 in International Application No. PCT/US2009/040289 filed on Apr. 11, 2009 and published as: WO 09/126945 on: Oct. 15, 2009.

Webpage printed from the internet on Feb. 21, 2008 at URL: http://www.matrixtechcorp.com/handheld/pipettor.aspx?id=40

MatrixTechnologies Thermo Scientific Matrix Liquid Handling Systems.

Nakane et al., "A Method for parallel automated thermal cycling of submicroliter samples," Genome Research vol. 11, Issue 3, 441-447, Mar. 2001.

Hile et al., "Microbiology Tray and Pipette Tracking as a Proactive Tangible User Interface," In Proc. of the 2nd Int. Conf. on Pervasive Computing, 2004.

Office Action mailed on: Dec. 14, 2011 in U.S. Appl. No. 12/422,250, filed Apr. 11, 2009, and published as 2009/0255949 on Oct. 15, 2009.

Office Action mailed on: Dec. 23, 2011 in U.S. Appl. No. 12/577,003, filed Oct. 9, 2009, and published as 2010/0089938 on Apr. 15, 2010.

Extended European Search Report dated: Nov. 4, 2011 in European Application No. EP09729893 filed on: Nov. 9, 2010.

Office Action mailed on: Feb. 4, 2013 in U.S. Appl. No. 12/422,250, filed Apr. 11, 2009, and published as 2009/0255949 on Oct. 15, 2009.

Office Action mailed on: Jun. 27, 2012 in U.S. Appl. No. 12/422,250, filed Apr. 11, 2009, and published as 2009/0255949 on Oct. 15, 2009.

Office Action mailed on: Jul. 16, 2012 in U.S. Appl. No. 29/345,141, filed Oct. 9, 2009.

Office Action mailed on: Jul. 30, 2012 in U.S. Appl. No. 29/335,253, filed Apr. 11, 2009.

Office Action mailed on: May 9, 2013 in U.S. Appl. No. 29/335,252, filed Apr. 11, 2009.

Office Action mailed on: Jul. 23, 2012 in U.S. Appl. No. 29/335,252, filed Apr. 11, 2009.

Office Action mailed on: Aug. 6, 2012 in U.S. Appl. No. 29/345,142, filed Oct. 9, 2009.

Office Action mailed on: Apr. 2, 2013 in U.S. Appl. No. 29/437,631, filed Nov. 19, 2012.

Office Action mailed on: May 10, 2013 in U.S. Appl. No. 29/335,253, filed Apr. 11, 2009.

Office Action mailed on Aug. 30, 2013 in U.S. Appl. No. 29/335,253, filed Apr. 11, 2009.

* cited by examiner

FIG. 6A
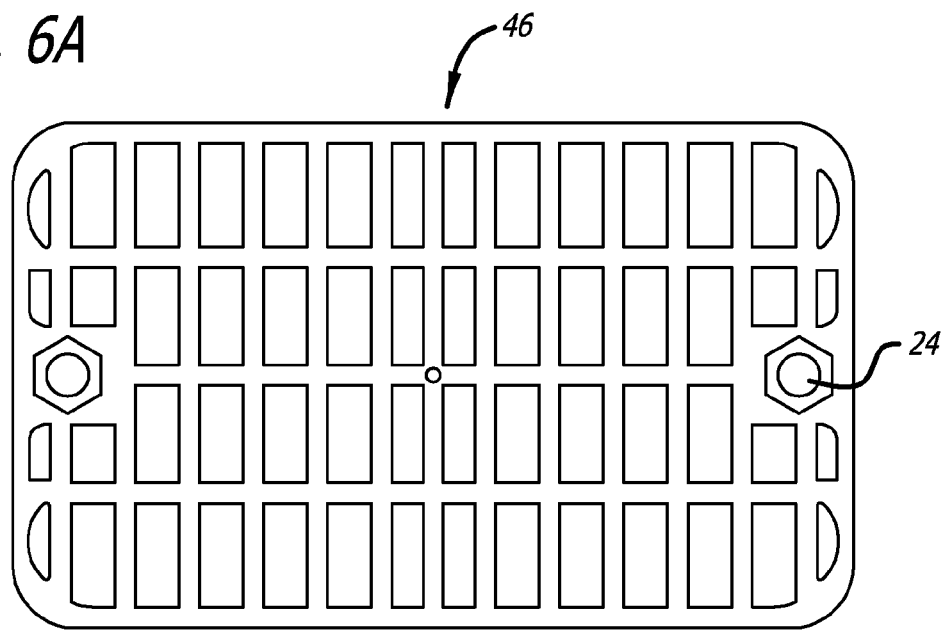
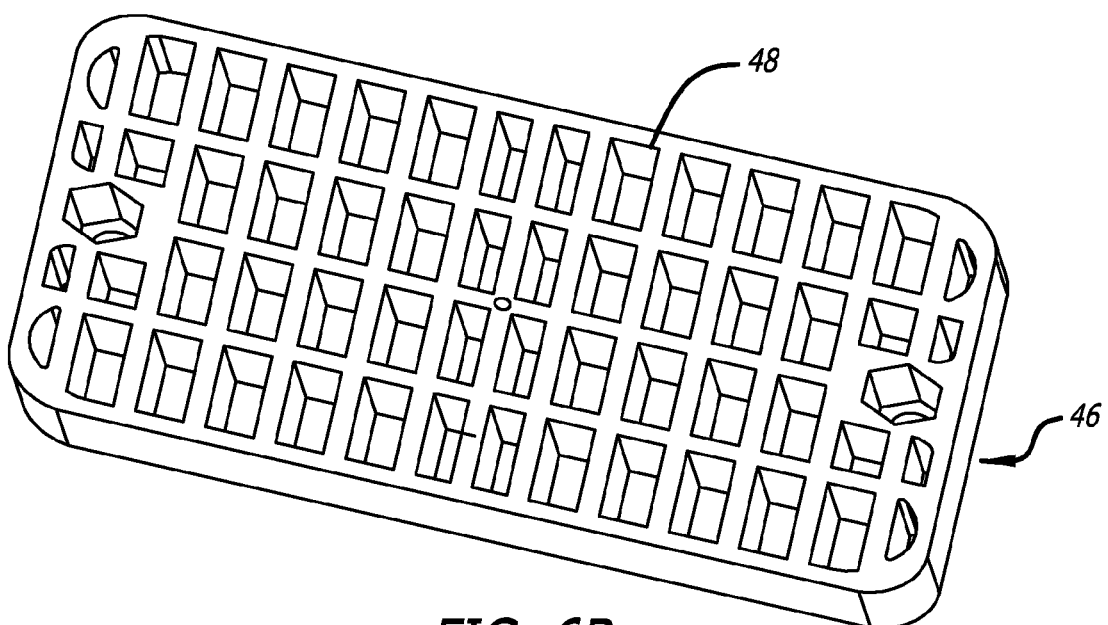
FIG. 6B

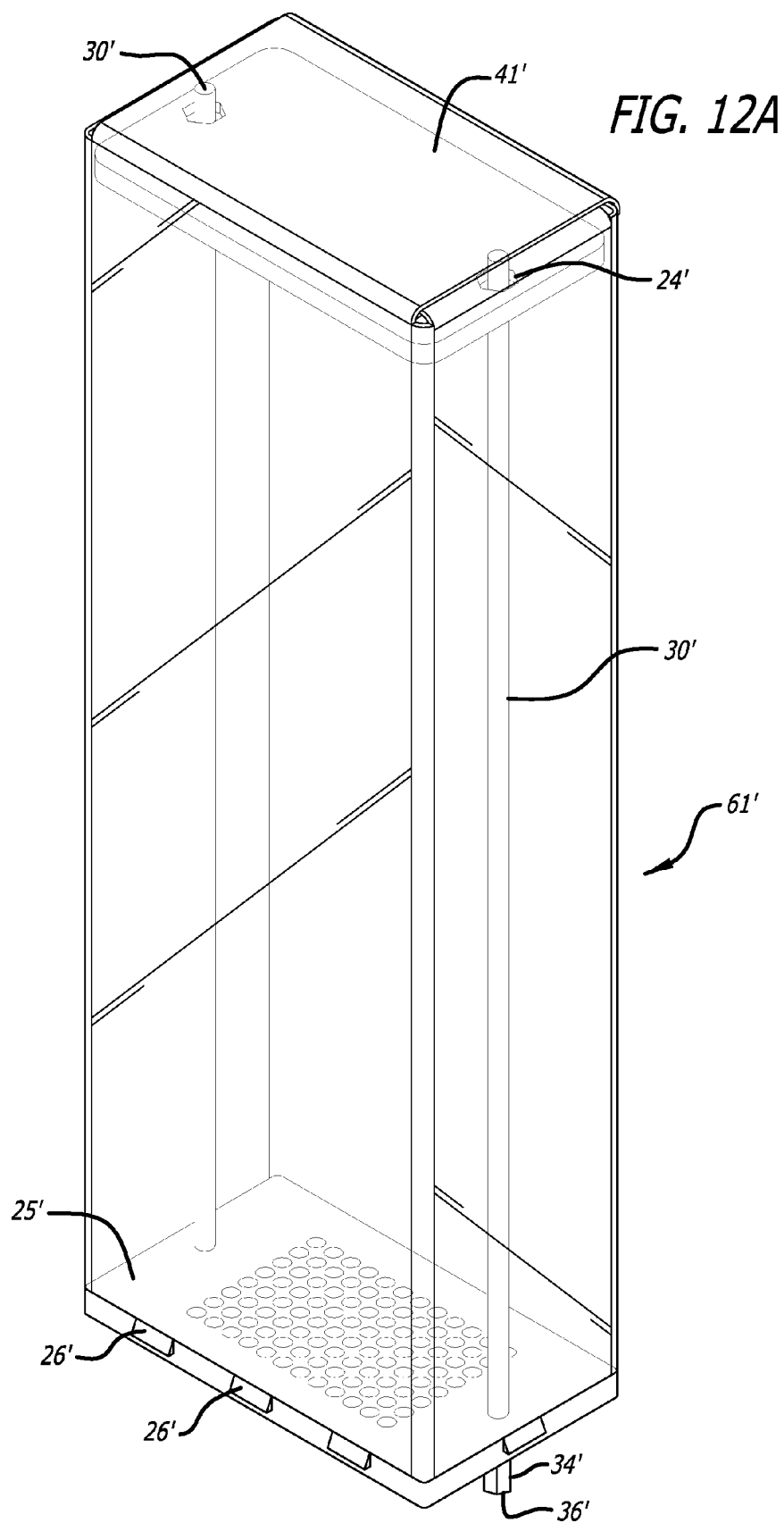

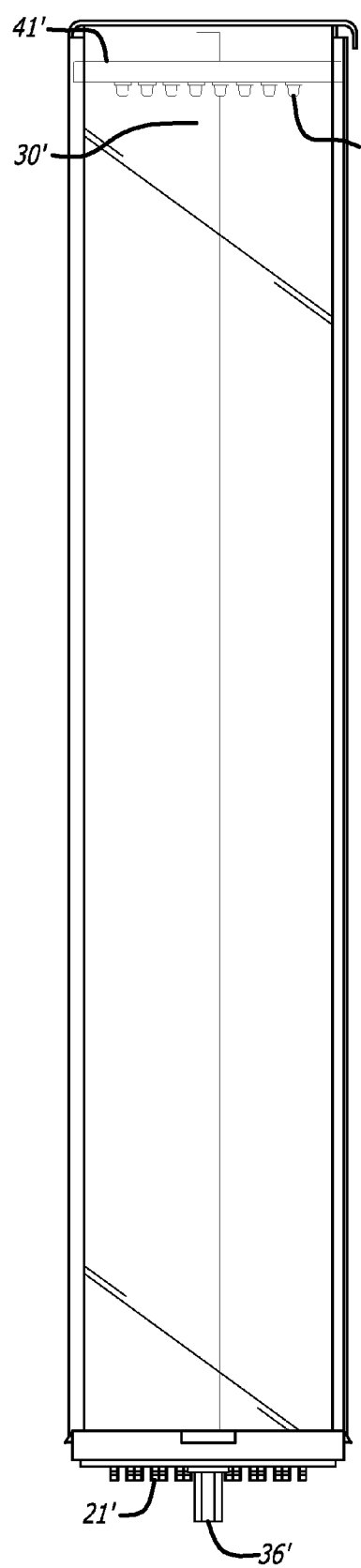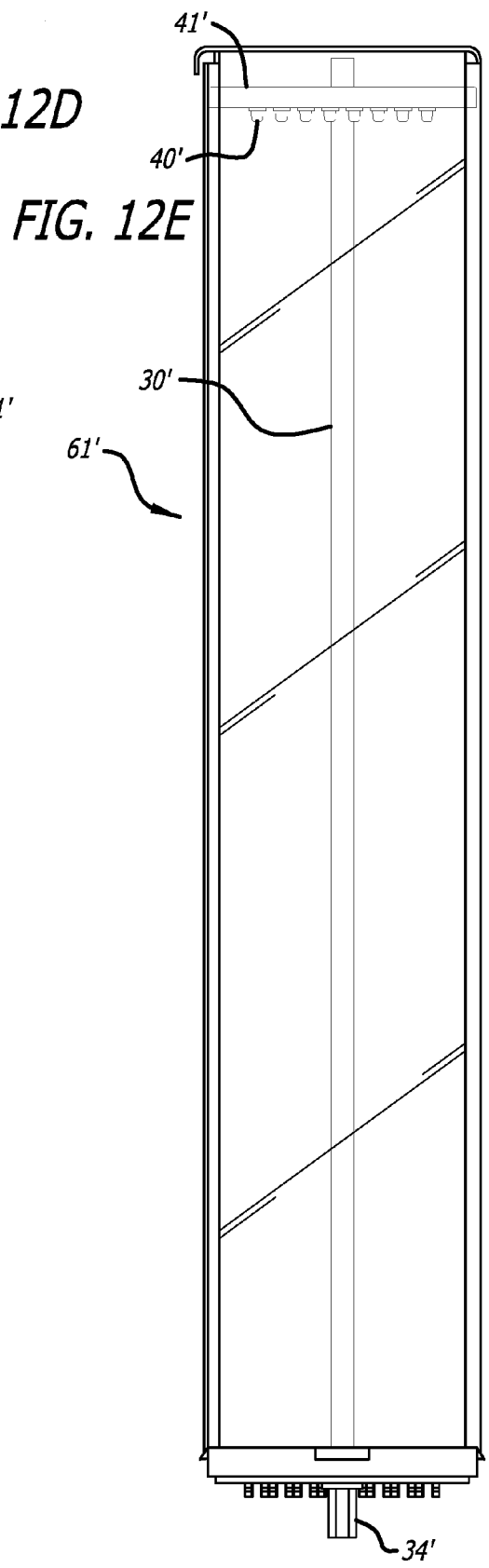
FIG. 12D
FIG. 12E

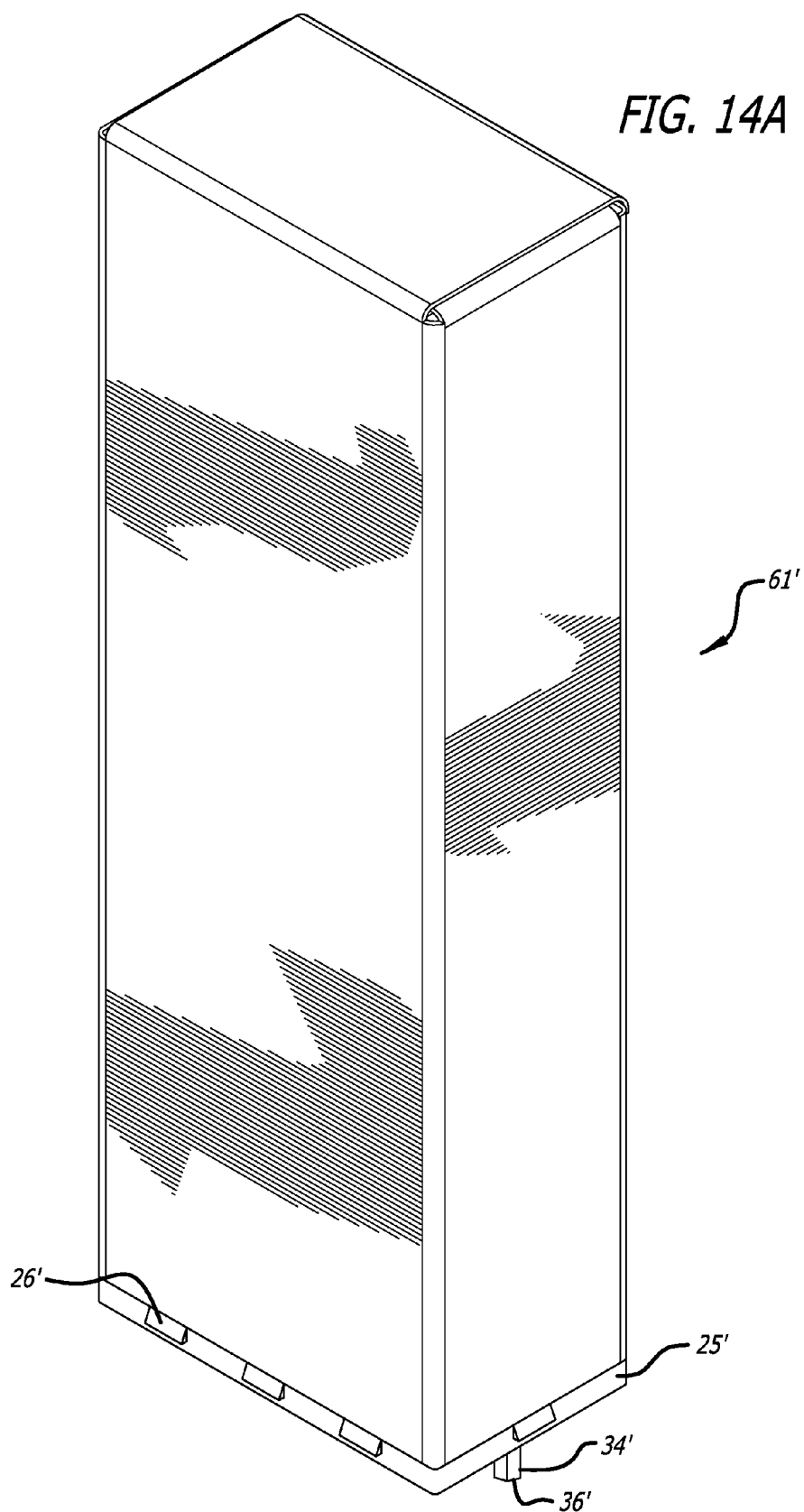

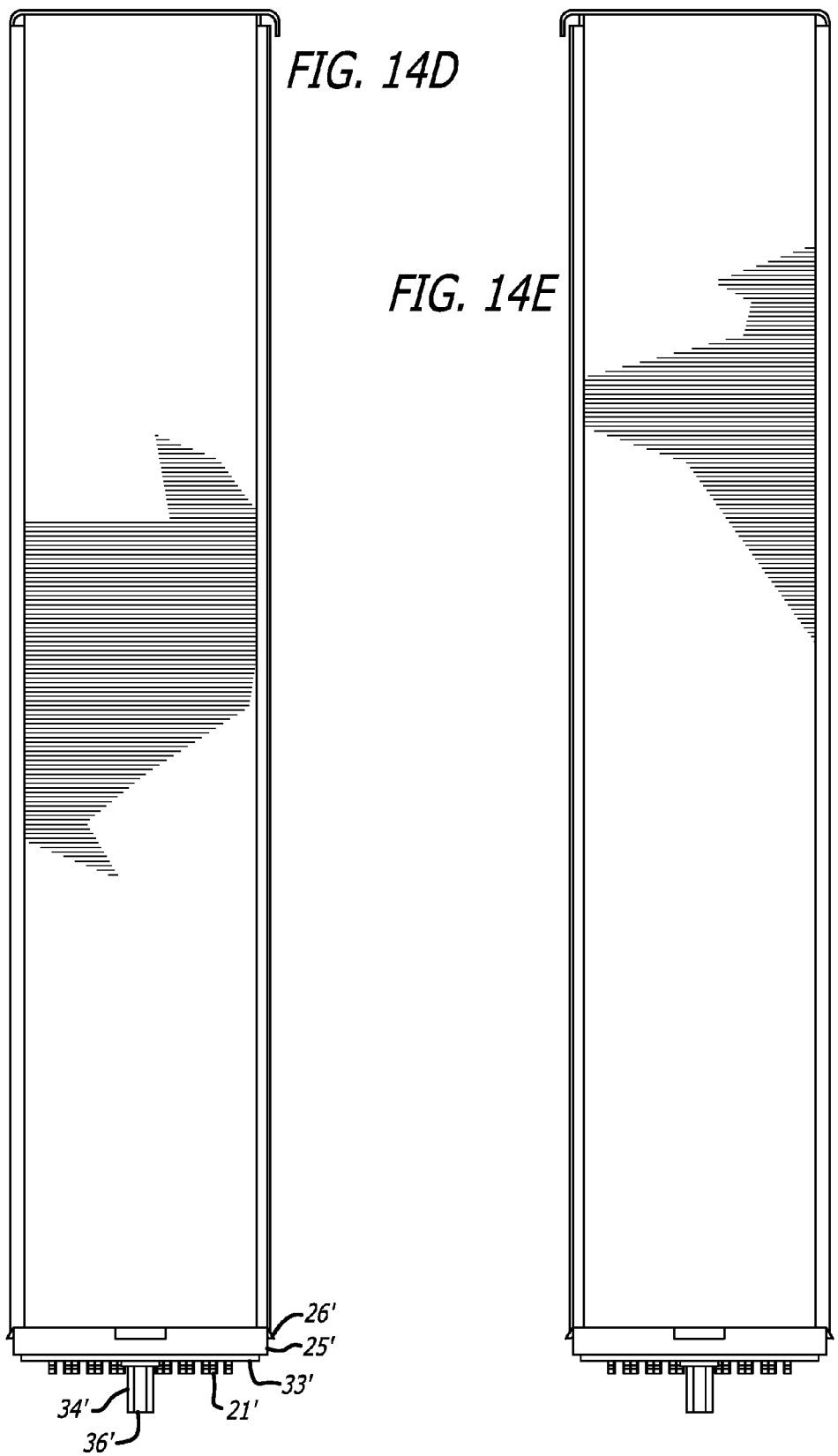

AUTOMATED PIPETTE TIP LOADING DEVICES AND METHODS

RELATED PATENT APPLICATIONS

This patent application claims the benefit of U.S. Patent Application No. 61/168,561 filed on Apr. 11, 2009, entitled AUTOMATED PIPETTE TIP LOADING DEVICES AND METHODS, naming Arta Motadel as an inventor. This patent application also claims the benefit of U.S. Patent Application No. 61/250,404 filed on Oct. 9, 2009, entitled AUTOMATED PIPETTE TIP LOADING DEVICES AND METHODS, naming Arta Motadel as an inventor. This patent application also claims the benefit of U.S. patent application Ser. No. 29/335,253 filed on Apr. 11, 2009, entitled AUTOMATED PIPETTE TIP LOADING DEVICES, naming Arta Motadel as an inventor. This patent application also claims the benefit of U.S. patent application Ser. No. 29/345,142 filed on Oct. 9, 2009, entitled AUTOMATED PIPETTE TIP LOADING DEVICE AND COMPONENTS, naming Arta Motadel as an inventor. The entire content of the foregoing patent applications is incorporated herein by reference, including all text, tables and drawings.

FIELD OF THE TECHNOLOGY

Described herein are method and device embodiments for storing, loading or handling of pipette tips. Some embodiments allow for convenient loading of multiple batches of pipette tips into loading blocks or plates with a minimal amount of waste and minimal effort by the user.

BACKGROUND

Pipette tips are used in large quantities for a wide variety of applications related to liquid material handling, such as measuring, dispensing and aspirating of the liquids. Pipette tips are often used in conjunction with hand held pipettors, such as mechanical or electrical pipettors, that have distal nozzles that are configured to be releasably engaged with a proximal port or opening of a pipette tip in a sealed relationship. The pipettor may then be used to apply a vacuum or otherwise decrease the pressure in the interior volume of the pipette tip in order to aspirate liquid into the pipette tip for transfer to another location. For some applications a single pipettor may be used, however, for some applications, particularly automated or robotic applications, pipettors or manifolds having multiple distal nozzles may be used to engage multiple pipettor tips disposed in a loading plate or block simultaneously.

For such configurations, after the pipette tips are seated onto the nozzles and removed from the loading block, a new set of pipette tips must be provided for the next cycle of liquid handling. Typically, a new set of pipette tips are taken from a package in a storage plate and loading block in a regularly spaced array and positioned for seating with the distal nozzles of the manifold. Because of the difficulty of manually handling large numbers of pipette tips due to the time consuming nature of such handling as well as the risk of contamination, pipette tips are generally pre-packaged in regularly spaced arrays spaced in pre-determined spacing to match the spacing of the array of distal nozzles. The pipette tips may be transferred from the packaging in a loading plate that is part of the packaging but may also include an entire loading plate and loading block in order to maintain the array configuration during handling and transfer to a location for seating to the manifold or pipettor.

For such multiple pipette tip arrays, because each pipette tip may require a significant amount of axial force between the respective nozzle and proximal opening of the pipette tip in order to be properly seated, the cumulative force required to seat an array of pipette tips may be quite high. For example, a 96 tip manifold may exert about 75 pounds to about 250 pounds of force on a loading block having a 96 tip array. Because of the amount of force generated, the loading block that supports the loading plate must be structurally strong and able to withstand the cumulative axial force without significant deformation. To be this strong, the block requires a significant amount of mass of material which is typically a polymer. Once the distal nozzles of the manifold have engaged and seated the pipette tips and withdrawn them from the loading plate and block, the loading block and plate are disposed of and replaced with a new loading block and plate that is full of new pipette tips. As a result, a user performing a high volume of such liquid handling cycles will be disposing of a large volume of loading blocks and plates which generates a large volume of polymer waste which may be environmentally unsound in many instances.

For embodiments of pipette tip arrays that transferred in a loading plate without the loading block of the package, the loading tray is lifted or moved from the packaging and positioned in a loading block. After each seating of an array of pipette tips, the loading plate must be removed or the z-axis position of the top of the plate will change with the addition of each new loading plate from a new package of pipette tips.

SUMMARY

Some embodiments of a pipette tip dispensing device include (a) a sleeve; (b) an activator plate within the sleeve, (c) a distal barrier plate within the sleeve disposed opposite to and spaced away from the activator plate, (d) two or more connectors in connection with the activator plate and distal barrier plate, (e) a plurality of nested pipette tip units between the activator and barrier plates, where: (i) each unit is aligned with a channel in the distal barrier plate, and (ii) the distal barrier plate comprises (1) a plurality of channels, where each channel comprises a diameter larger than the widest portion of a pipette tip, (2) a top surface, and (3) a bottom surface. In some embodiments, the bottom surface optionally comprises a plurality of tails around some or all of the channels, wherein (i) the tails extend in a nearly perpendicular orientation from the bottom surface, and (ii) the tails around each channel contact a pipette tip when a pipette tip is dispensed and passes by the tails, thereby imparting (e.g., applying) a frictional force on the pipette tip when it is dispensed. In some embodiments, the optional tails deflect outwards against the pipette tip before, and/or at the same time the pipette tip is being dispensed (e.g., the pipette tip is translating), and sometimes the tails contact the proximal portion of a pipette tip. In some embodiments, a subset of channels in the distal barrier plate are optionally surrounded by tails that eject pipette tips of an array at one time, and another subset of channels in the plate are optionally surrounded by tails that eject pipette tips of the same array at another time. A distal barrier plate may include 2, 3, 4, 5, 6, 7, 8, 9, 10, 11, 12, 13, 14, 15, 16, 17, 18, 19 or 20 of such subsets of channels. In some embodiments, the top surface and/or the bottom surface are substantially flat. In certain embodiments, the sleeve can comprise a degradable or biodegradable material (e.g., banana peel, bamboo, and the like).

In some embodiments, the channel can have 2, 3, 4, 5, 6, 7, 8, 9, 10 or more optional tails. Each channel of the barrier plate can have tails of the same length. In some embodiments, each channel of the barrier plate can have tails of different lengths. Channels located in the center of the barrier plate can have the longest tails. Channels located in the center of the barrier plate can have the shortest tails. In certain embodiments, subsequent channels concentrically disposed about a central longitudinal axis can have sequentially shorter tails in length in a stepwise manner. In some embodiments, subsequent channels concentrically disposed about a central longitudinal axis can have sequentially longer tails in length in a stepwise manner. Channels located in the center of the barrier plate along the X axis can have tails of the same length and channels along the Y axis comprise tails of varying length. In some embodiments, channels located in the center of the barrier plate along the Y axis can have tails of the same length and channels along the X axis comprise tails of varying length. Channels located in the center of the barrier plate along the X and Y axes can have tails of varying length in certain embodiments. Each channel can have an even number of tails in some embodiments. Tails directly opposite one another around a channel can have the same length in certain embodiments. Tails directly opposite one another around a channel can have a different length in some embodiments. Tails adjacent to one another can have a different length in certain embodiments. In some embodiments, the activator plate, distal barrier plate, connectors, and plurality of pipette tips are located in the sleeve. The sleeve in certain embodiments further comprises a top portion, four sides and a bottom lid. In some embodiments, the sleeve is comprised of one or more of a polymer material, chipboard, glass, Styrofoam, wood, metal, plastic, paper, or combination thereof. In some embodiments, the distal barrier plate further comprises one or more fasteners along one or more of its vertical lateral sides configured to connect with the sleeve. The term "fastener" as used herein refers to a member that connects a distal barrier plate to a sleeve member, including but not limited to Velcro, button, hook, adhesive, prong and the like. The distal barrier plate also can also have one or more connections along one or more of its vertical lateral sides configured to connect with sleeve in certain embodiments.

In certain embodiments, optional tails can be at an internal angle of about 89° to about 80° from the bottom surface of the distal barrier plate. Tails can be at an internal angle between 88-85°, 87-84°, 86-83° or 86-85° from the bottom surface of the distal barrier plate in certain embodiments. The tails can be at an internal angle of about 87° from the bottom surface of the distal barrier plate. The tails can be between 0.01 μm-2.0 mm in length in some embodiments, and sometimes the tails can be between 0.05 μm-2.0 mm in length. The tails around a channel are not in the channel in some embodiments.

The housing unit further can have a top portion and four sides in some embodiments. The movable bottom platform positions a loading block directly distal to the barrier plate to receive an ejected array of pipette tips from the dispensing device in certain embodiments. The housing can be made of any suitable material, and sometimes is a polymer material, and the polymer material of the housing can be made of a molded polypropylene in some embodiments. The polymer material of the housing can be a thickness of about 0.005 inches to about 0.05 inches in certain embodiments. The activator plate can have a member on the top portion of the plate that maintains contact with and restricts lateral displacement of the proximal portion of the pipette tips. The member can be selected from the group consisting of foam, a raised grid, and a plurality of proximal alignment members in some embodiments. The activator plate can be made from a polymer material, and the polymer material of the activator plate can be made of a molded polypropylene in some embodiments. The polymer material of the activator plate can be a thickness of about 0.30 inches to about 0.65 inches. The activator plate can have a top portion and a roof portion in some embodiments. The polymer material is molded with raised ridges on the top portion and the roof portion in certain embodiments. The ridges can provide strength and rigidity to the activator plate in some embodiments. In some embodiments, the housing unit also includes a motor, electrical engine or other type of drive mechanism that can translate a plate in an automated dispensing unit.

A pipette tip array can have 96, 384, or more numbers of pipette tips, and a pipette tip unit can be arranged in an array of pipette tip units. Each nested pipette tip unit can have 2, 3, 4, 5, 6, 7, 8, 9, 10, 11, 12, 13, 14, 15, 16, 17 or more pipette tips. The connectors are rods in some embodiments. The rods in connection with the activator plate and the distal barrier plate can have threads. The activator plate and the distal barrier plate are translated towards one another by rotation of the rods in certain embodiments. The activator plate can have threaded members, and each threaded member engages a threaded portion of each rod, whereby the activator plate translates towards the distal barrier plate by rotation of the rods in some embodiments. The rods sometimes are rotated by a motor. The motor is activated by a user controlled mechanism in some embodiments. The user controlled mechanism is a lever switch, button, or sensor in certain embodiments. The motor stops rotating the rods by a pressure sensor gauge in some embodiments. The pipette tips that have passed through the distal barrier plate are sterilized in certain embodiments, and sterilization sometimes is by UV irradiation, ionization, alcohol or gamma radiation. In some embodiments, the sterilization can be initiated by a controller or switch activated by a user.

Certain embodiments of a method of simultaneously dispensing an array of multiple pipette tips into a loading block, include (a) providing a dispensing device that includes a nested array of regularly spaced pipette tips between a top activator plate and a bottom distal barrier plate, wherein: (i) the activator plate and the distal barrier plate are in connection with two or more connectors, (ii) the distal barrier plate includes (1) a plurality of channels, where each channel has a diameter larger than the widest portion of a pipette tip, (2) a top surface, and (3) a bottom surface, (b) engaging the dispensing device with a loading block such that distal ends of the pipette tips are disposed above and/or within receptacles of the loading block, and (c) actuating a motor of the dispensing device in effective connection with the connectors that moves the connectors, whereby (i) the activator plate and the distal barrier plate are translated towards one another thereby applying an axial force on the array of pipette tips, and (ii) the array of pipette tips is ejected into respective receptacles in the loading block. In some embodiments, the connectors are rods. In certain embodiments, the bottom surface comprises a plurality of tails around some or all of the channels, wherein the tails extend in a nearly perpendicular orientation from the flat bottom surface. In some embodiments the axial force dispenses the array of pipette tips through the channels and past the optional tails and the tails contact and deflect outwards against the pipette tips and impart a frictional force on the pipette tips. In some embodiments, the optional tails deflect outwards against the pipette tip before, and/or at the same time the pipette tip is being dispensed (e.g., the pipette tip is translating), and sometimes the tails contact the proximal portion of a pipette tip. In some embodiments, a subset of channels in the distal barrier plate are surrounded by tails that eject pipette tips of an array at one time, and another subset of channels in the plate are surrounded by tails that eject pipette tips of the same array at another time. A distal barrier plate may include 2, 3, 4, 5, 6, 7, 8, 9, 10, 11, 12, 13, 14, 15, 16, 17, 18, 19 or 20 of such subsets of channels. In some embodiments, the top surface and/or the bottom surface are substantially flat.

In some embodiments pertaining to the method embodiments of the preceding paragraph, the barrier plate can have 2, 3, 4, 5, 6, 7, 8, 9, 10 or more optional tails. Each channel of the barrier plate can have tails of the same length. In some embodiments, each channel of the barrier plate can have tails of different lengths. Channels located in the center of the barrier plate can have the longest tails. In certain embodiments, channels located in the center of the barrier plate can have the shortest tails. Subsequent channels concentrically disposed about a central longitudinal axis can have sequentially shorter tails in length in a stepwise manner. In some embodiments, subsequent channels concentrically disposed about a central longitudinal axis can have sequentially longer tails in length in a stepwise manner. Channels located in the center of the barrier plate along the X axis can have tails of the same length and channels along the Y axis comprise tails of varying length. In certain embodiments, channels located in the center of the barrier plate along the Y axis can have tails of the same length and channels along the X axis comprise tails of varying length. In certain embodiments, channels located in the center of the barrier plate along the X and Y axes can have tails of varying length. Each channel can have an even number of tails in some embodiments. Tails directly opposite one another around a channel can have the same length in certain embodiments. Tails directly opposite one another around a channel can have a different length in some embodiments. Tails adjacent to one another can have a different length in certain embodiments. Optional tails can be at an internal angle of about 89° to about 80° from the bottom surface of the distal barrier plate. In some embodiments, tails can be at an internal angle between 88-85°, 87-84°, 86-83° or 86-85° from the bottom surface of the distal barrier plate. Tails can be at an internal angle of about 87° from the bottom surface of the distal barrier plate in some embodiments. Optional tails can be between 0.01 μm-2.0 mm in length, and sometimes tails can be between 0.05 μm-2.0 mm in length. Tails around a channel are not in the channel in certain embodiments. The actuating step can be repeated by automatic or manual activation until all the nested pipette tips are ejected from the dispensing device in some embodiments. The automatic activation can be performed by a pressure gauge sensor in certain embodiments. The manual activation can be performed by a lever switch, button, or sensor in some embodiments.

Certain embodiments are described further in the following description, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

Certain features common to some or all the figures (e.g., FIG., or FIGS.) presented herein are identified by a prime symbol (') after the reference character. For example a feature labeled 14 in one drawing and substantially similar or substantially identical to a feature in one or more additional drawings, would be labeled 14' in the second and subsequent drawings. In instances where a figure is not explicitly described, but contains reference characters containing the prime symbol ('), it will be understood the description given for the reference character in one figure, will be substantially identical for the reference character with the prime symbol.

FIG. 2A shows X and Y axes referenced herein.

FIG. 3 shows an optional base plate.

FIG. 5 shows an activator plate or actuator plate.

FIG. 6A shows another view of an activator plate. FIG. 6A shows the roof surface of the plate. FIG. 6B shows the plate from FIG. 6A at a slanted angle.

FIGS. 12A-12H illustrate various views of an auto eject cartridge with a transparent sleeve, with and without pipette tips. FIG. 12A shows a perspective view of an auto eject cartridge with a transparent sleeve without pipette tips. FIG. 12B shows a front view of an auto eject cartridge with a transparent sleeve without pipette tips. FIG. 12C shows a rear view of an auto eject cartridge with a transparent sleeve without pipette tips. FIGS. 12D and 12E show side views of an auto eject cartridge with a transparent sleeve without pipette tips. FIG. 12F shows a top view of a cartridge with a transparent sleeve without pipette tips. FIG. 12G shows a bottom view of cartridge with a transparent sleeve without pipette tips. FIG. 12H shows a front view of an auto eject cartridge with a transparent sleeve loaded a nested array of regularly spaced pipette tips between a top activator plate and a bottom distal barrier plate. A cartridge may be provided with or without a nested array of spaced pipette tips.

FIGS. 14A-14G show various views of an auto eject cartridge with an opaque sleeve, without pipette tips. FIG. 14A shows a perspective view of an auto eject cartridge with an opaque sleeve without pipette tips. FIG. 14B shows a front view of an auto eject cartridge with an opaque sleeve without pipette tips. FIG. 14C shows a rear view of an auto eject cartridge with an opaque sleeve without pipette tips. FIGS. 14D and 14E show side views of an auto eject cartridge with an opaque sleeve without pipette tips. FIG. 14F shows a top view of an auto eject cartridge with an opaque sleeve without pipette tips. FIG. 14G shows a bottom view of an auto eject cartridge with an opaque sleeve without pipette tips. A cartridge may be provided with or without a nested array of regularly spaced pipette tips.

DETAILED DESCRIPTION

Figure 1A:
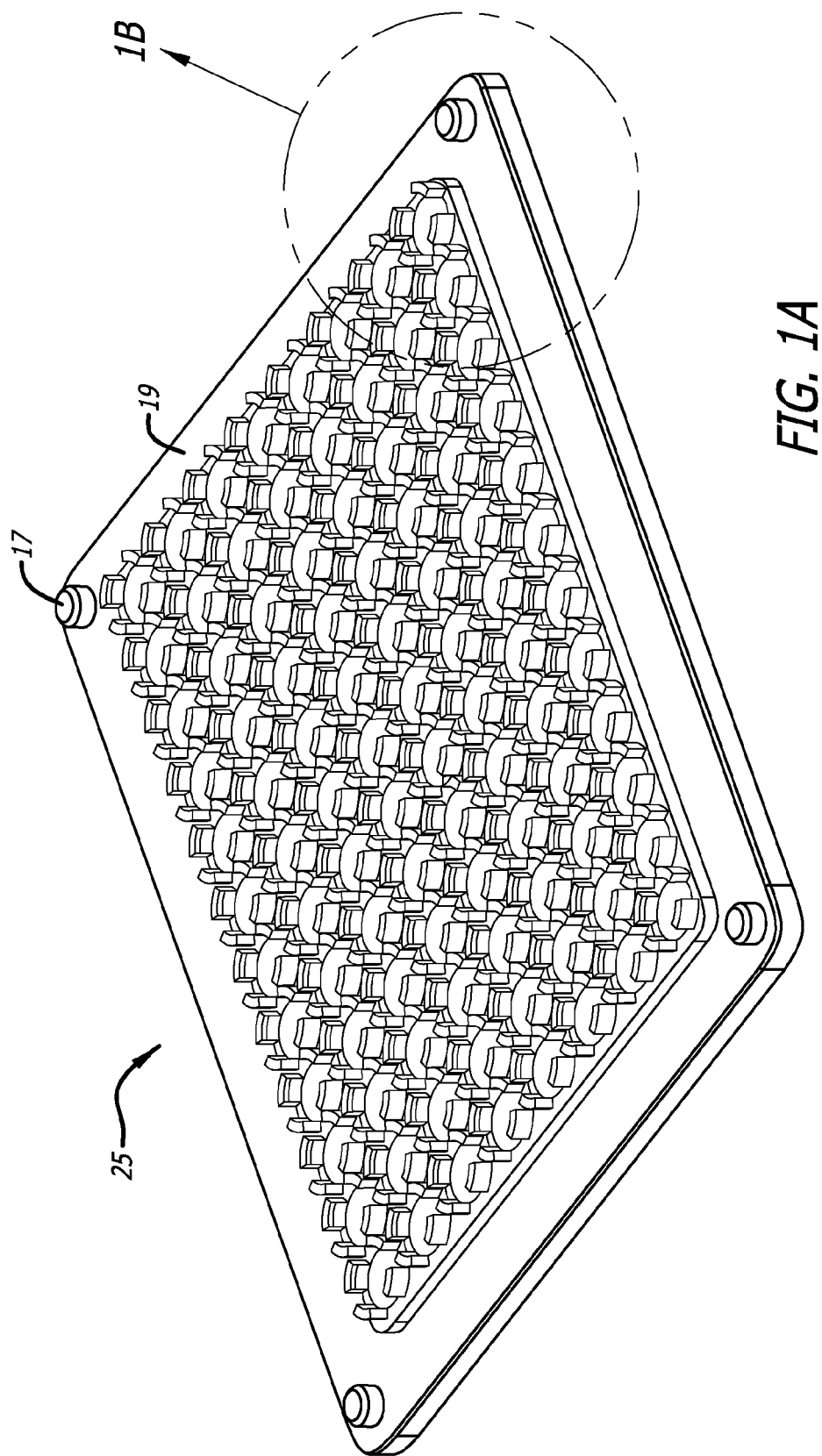
FIG. 1A shows a perspective view of a distal barrier plate with optional tails pointing in an upward orientation.

Discussed herein are method and device embodiments for handling, storage and dispensing of pipette tips used for a variety of material handling applications. Pipette tips may generally be engaged with a distal nozzle of a pipettor or similar device in order to draw and drop liquid slugs in precise amounts. Such tips may be used for the transfer and handling of liquids for applications such as titration and dispensing of liquids, DNA sequencing, cycle sequencing, PCR and other DNA analysis as well as other liquid handling applications. For many of these applications, large numbers of samples must be processed in a precise manner and, as such, a large number of pipette tips are used for such methods. In order to avoid cross contamination of samples, pipette tips are typically used only once for each sample being processed. Because of the large number of samples being processed and the single use nature of the pipette tips, a large number of pipette tips need to engaged with pipettor type devices and then removed from those devices and disposed of.

Due to such large volume handling and disposal, it is desirable for some applications to have devices and methods for pipette tip transfer and loading in arrays of multiple tips from a single packaging source to avoid the need for disposing of a package for each array loaded onto a pipettor device. What is also desirable for some applications are devices and methods for loading an array of multiple pipette tips without the need to transfer a separate loading plate from the packaging of the tips which may cause additional waste for disposal in addition to affecting the cumulative z-axis height of the pipette tips being loaded. Some pipette tip dispensing device and method embodiments discussed herein are directed to the handling, storage and simultaneous dispensing of a plurality of pipette tips disposed in a regularly spaced array into a loading plate or block. Some of these embodiments have the capacity to serially dispense multiple arrays or pipette tips without transferring loading plates or the need for handling of individual pipette tips. Some embodiments of pipette tip dispensing devices discussed herein are also capable of dispensing arrays of multiple pipette tips accurately and conveniently without the need to transfer a loading tray from the packaging of the pipette tips.

Device and method embodiments described herein provide several advantages. Device and method embodiments herein allow for storing, loading or handling of pipette tips, and allow for convenient loading of pipette tips without the need to transfer a storage plate that may affect the z-axis location of the top surface of the loading block into which the pipette tips are transferred. Device and method embodiments herein also allow for multiple pipette tips to be loaded simultaneously without the transfer of a storage plate. Such embodiments also allow for pipette tips to be stored in a nested configuration, in one or more nested column arrays for some embodiments, and allow the bottom pipette tip of each nested column to be conveniently dispensed into a loading plate or loading block.

Pipette Tips

A pipette tip can be of any geometry useful for dispensing fluids in combination with a dispensing device. Pipette tips sometimes are available in sizes that hold from 0 to 10 microliters, 0 to 20 microliters, 1 to 100 microliters, 1 to 200 microliters and from 1 to 1000 microliters, for example. The external appearance of pipette tips may differ, and certain pipette tips can have a continuous tapered wall forming a central channel or tube that is roughly circular in horizontal cross section, in some embodiments. A pipette tip can have any cross-sectional geometry that results in a tip that (i) provides suitable flow characteristics, and (ii) can be fitted to a dispenser (e.g., pipette), for example. Pipette tips sometimes taper from the widest point at the top-most portion of the pipette tip (pipette proximal end or end that engages a dispenser), to a narrow opening at the bottom most portion of the pipette tip (pipette distal end or end used to acquire or dispel fluid). In certain embodiments, a pipette tip wall includes two or more taper angles. The inner surface of the pipette tip sometimes forms a tapered continuous wall, in some embodiments, and in certain embodiments, the external wall may assume an appearance ranging from a continuous taper to a stepped taper or a combination of smooth taper with external protrusions. An advantage of an externally stepped taper is compatibility with pipette tip racks from different manufacturers. The bore of the top-most portion of the central channel or tube generally is wide enough to accept a particular dispenser apparatus (e.g., nozzle, barrel).

In some embodiments, a pipette tip has (i) an overall length of about 1.10 inches to about 3.50 inches (e.g., about 1.25, 1.50, 1.75, 2.00, 2.25, 2.50, 2.75, 3.00, 3.25 inches); (ii) a fluid-emitting distal section terminus having an inner diameter of about 0.01 inches to about 0.03 inches (e.g., about 0.015, 0.020, 0.025 inches) and an outer diameter of about 0.02 to about 0.7 inches (e.g., about 0.025, 0.03, 0.04, 0.05, 0.06 inches); and (iii) a dispenser-engaging proximal section terminus having an inner diameter of about 0.10 inches to about 0.40 inches (e.g., about 0.15, 0.20, 0.25, 0.30, 0.35 inches) and an outer diameter of about 0.15 to about 0.45 inches (e.g., about 0.20, 0.25, 0.30, 0.35, 0.45 inches). In the latter embodiments, the inner diameter is less than the outer diameter.

The wall of the distal section of a pipette tip sometimes is continuously tapered from the wider portion, which is in effective connection with the proximal section, to a narrower terminus. The wall of the distal section, in some embodiments, forms a stepped tapered surface. The angle of each taper in a distal section is between about zero degrees to about thirty degrees from the central longitudinal vertical axis of the pipette tip (e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 degrees), in certain embodiments. In some embodiments, the wall of the distal section forms stepped vertical sections. The wall thickness of a distal section may be constant along the length of the section, or may vary with the length of the section (e.g., the wall of the distal section closer to the proximal section of the pipette tip may be thicker or thinner than the wall closer to the distal section terminus; the thickness may continuously thicken of thin over the length of the wall). The distal section of a pipette tip generally terminates in an aperture through which fluid passes into or out of the distal portion. A distal section of a pipette tip may contain a filter, insert or other material.

The wall of the proximal section of a pipette tip sometimes is continuously tapered from the top portion, a narrower terminus. The top portion generally is open and often is shaped to receive a pipette tip engagement portion of a dispensing device. The wall of a proximal section, in some embodiments, forms a stepped tapered surface. The angle of each taper in the proximal section is between about zero degrees to about thirty degrees from the central longitudinal vertical axis of the pipette tip (e.g., about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 degrees), in certain embodiments. The wall thickness of a proximal section may be constant over the length of the section, or may vary with the length of the proximal section (e.g., the wall of the proximal section closer to the distal section of the pipette tip may be thicker or thinner than the wall closer to the top of the proximal section; the thickness may continuously thicken or thin over the length of the wall). A proximal section of a pipette tip may contain a filter, insert or other material.

In certain embodiments, pipette tips in a pipette tray comprise one or more of a filter component and/or an insert component. A filter may be located in any suitable portion of a pipette tip, and sometimes is located in a proximal portion of a pipette tip near a pipette tip aperture that can engage a dispensing device. A filter can be of any shape (e.g., plug, disk; U.S. Pat. Nos. 5,156,811 and 7,335,337) and can be manufactured from any material that impedes or blocks migration of aerosol through the pipette tip to the proximal section terminus, including without limitation, polyester, cork, plastic, silica, gels, and the like, and combinations thereof. In some embodiments a filter may be porous, non-porous, hydrophobic, hydrophilic or a combination thereof. A filter in some embodiments may include vertically oriented pores, and the pore size may be regular or irregular. Pores of a filter may include a material (e.g., granular material) that can expand and plug pores when contacted with aerosol (e.g., U.S. Pat. No. 5,156,811). In certain embodiments, a filter may include nominal, average or mean pore sizes of about 10, 9, 8, 7, 6, 5, 4, 3, 2, 1, 0.5, or 0.05 micrometers, for example. A section of a pipette tip also may include an insert or material that can interact with a molecule of interest, such as a biomolecule. The insert or material may be located in any suitable location for interaction with a molecule of interest, and sometimes is located in the distal section of a pipette tip (e.g., a material or a terminus of an insert may be located at or near the terminal aperture of the distal section). An insert may comprises one or more components that include, without limitation, multicapillaries (e.g., US 2007/0017870), fibers (e.g., randomly oriented or stacked, parallel orientation), and beads (e.g., silica gel, glass (e.g. controlled-pore glass (CPG)), nylon, Sephadex®, Sepharose®, cellulose, a metal surface (e.g. steel, gold, silver, aluminum, silicon and copper), a magnetic material, a plastic material (e.g., polyethylene, polypropylene, polyamide, polyester, polyvinylidenedifluoride (PVDF)), Wang resin, Merrifield resin or Dynabeads®). Beads may be sintered (e.g., sintered glass beads) or may be free (e.g., between one or two barriers (e.g., filter, frit)). Each insert may be coated or derivitized (e.g., covalently or non-covalently modified) with a molecule that can interact with (e.g., bind to) a molecule of interest (e.g., C18, nickel, affinity substrate).

Figure 7:
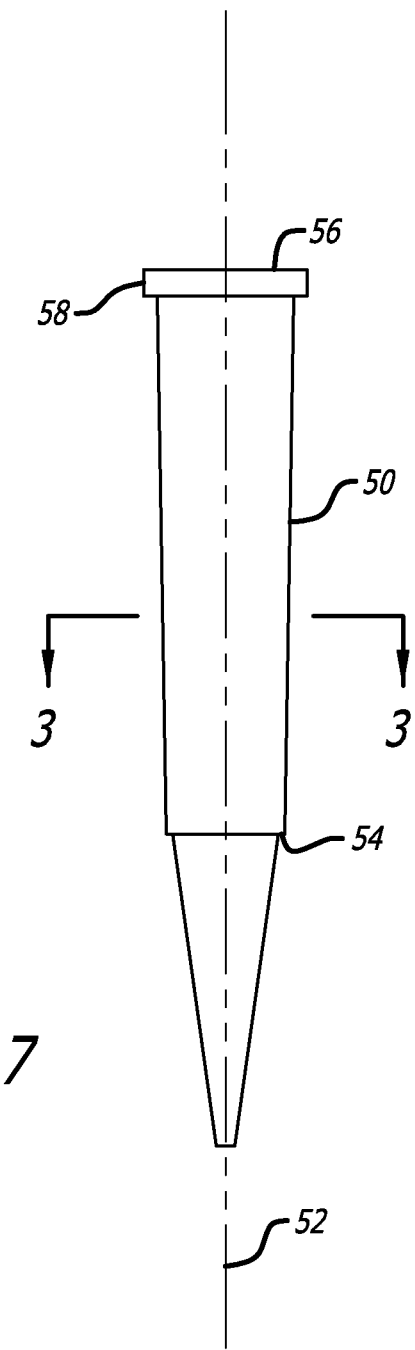
FIG. 7 shows an elevation view of an embodiment of a pipette tip.

A specific embodiment of pipette tip 50 is shown in FIG. 7, however, pipette tips may have a wide variety of configurations, dimensions and materials, each of which may be accommodated for use with any of the dispensing device embodiments discussed herein. For example, pipette tips may be configured as filter tips that include one, two, three or more filter elements disposed within a barrel of the tip in order to block aerosols from the pipettor device as well as other purposes.

The pipette tip 50 shown has a generally barrel shaped configuration which is concentrically disposed about a longitudinal axis 52 of the pipette tip 50. An inner lumen, not shown, extends coaxially along the length of the pipette tip 50 and tapers generally from the proximal opening of the pipette tip to a smaller distal opening. The proximal opening at a proximal end 56 of the tip 50 may have an inside surface with a tapered contour that is configured to engage an outer surface of a distal nozzle of a pipettor device, such as a pipettor device, in a sealed and releasable arrangement.

An outer surface of the proximal end of the pipette tip may have a rim, shoulder or other structure 58 that forms a major outer transverse dimension of the tip 50 which is disposed at the axial position of the pipette tip 50 having the largest transverse dimension. The barrel shaped configuration may have a generally round transverse cross section with the major outer transverse dimension at the proximal end 56 of the pipette tip of about 0.2 inches to about 0.4 inches, more specifically, about 0.25 inches to about 0.35 inches, for some embodiments. The outer transverse dimension of the pipette tip may taper to a minor outer transverse dimension at a distal end of the pipette tip 50 of about 0.02 inches to about 0.05 inches, more specifically, about 0.03 inches to about 0.04 inches, for some embodiments. The inner lumen may have a contour and taper that substantially corresponds to the taper and contour profile of the outer surface. The distal port or opening at the distal end of the inner lumen of the pipette tip may have a transverse dimension or diameter of about 0.01 inches to about 0.03 inches, more specifically, about 0.015 inches to about 0.025 inches, for some embodiments.

The shoulder portions 54 of the outer surface of some pipette tip embodiments 50 may have a minor transverse dimension that will fit within the proximal opening of another similar pipette tip and a major transverse dimension that is larger than the proximal opening of a similar pipette tip. With such an arrangement, the shoulder portion 54 of a first pipette tip thereby includes a distal surface or feature that may engage a proximal end or surface of another corresponding second pipette tip that is in nested engagement with the first pipette tip. The engagement of the shoulder portion of the first pipette tip with a proximal surface of the second pipette tip allows the transfer axial force between the first and second nested pipette tips without engaging the respective inner and outer tapered surfaces of the tips which might cause them to bind together making release of the tips from each other difficult.

The wall thickness of some embodiments of pipette tips may be about 0.003 inches to about 0.01 inches and the overall length of some pipette tip embodiments may be about 1.5 inches to about 3.5 inches, more specifically, about 2 inches to about 3 inches. Some embodiments of pipette tips may be made of suitable polymers such as polypropylene, polyethylene, polystyrene, polyurethane and the like as well as any other suitable polymers.

A pipette tip unit is arranged in an array of pipette tip units in some embodiments. Each unit has a plurality of nested pipette tips, and units are arranged in an array in certain embodiments. The relative configuration of nested pipette tips often is determined where a first portion of an inner surface of a first pipette tip interferes with a second portion of the outer surface of a second pipette tip nesting in and above the first pipette tip (e.g., the inner diameter of the first portion is about equal to the outer diameter of the second portion). Pipette tips can be dispensed as an array of pipette tips one pipette tip (i.e., one level) high. For example, a pipette tip array can fill all the holes in a loading block. When a device of the present technology is filled with an array of pipette tip units and actuated, a one-layer pipette tip array would be ejected into an empty loading block 7, thus filling it, in some embodiments. Each pipette tip unit comprises 2, 3, 4, 5, 6, 7, 8, 9, 10, 11, 12, 13, 14 or more nested pipette tips in some embodiments. The pipette tips often are nested continuously, and there often are no intermediate plates or intermediate components between the nested pipette tips.

Distal Barrier Plate

In some embodiments, the distal barrier plate 25, FIGS. 1A-1C, 2A-2C and 10A-10E may have a thickness and material rigidity sufficient to prevent significant deformation upon the application of actuation force to the pipette tips 50 disposed in the plate 25. As such, the distal barrier plate 25 may have a thickness of about 0.05 inches to about 0.3 inches, more specifically, about 0.1 inches to about 0.25 inches. For some embodiments, the barrier plate 25 may be made from suitable metal, such as aluminum, or polymers such as polypropylene, polycarbonate, polyethylene, polystyrene, polyurethane and the like as well as any other suitable polymers that may be molded, thermoformed or the like. For some embodiments, the barrier plate 25 may have a length of about 2 inches to about 6 inches and a width of about 1 inch to about 4 inches.

In some embodiments, certain geometric aspects of the distal barrier plate, through which pipette tips are dispensed, are substantially similar to, or the same as, geometric aspects of a pipette tip rack or holder configured for use in conjunction with automated dispensing devices and/or biological workstations. Such geometric aspects can include, for example, center-to-center distances between channels, channel diameter, rectangular dimensions around the perimeter of the channels. In some embodiments, a distal barrier plate of a pipette tip dispenser device is configured to load pipette tips into racks that conform to American National Standards Institute (ANSI) standard dimensions, accepted by the Society for Biomolecular Sciences (SBS), for devices used in high throughput applications related to the use of microtiter plates (e.g., multi-channel dispensers (manual or automated), pipette tip racks, pipette tips, and the like), in certain embodiments. In certain embodiments, barrier plate 25 may have a footprint length of between about 5 inches and about 5.1 inches (e.g., length of about 5.00 inches, about 5.01 inches, about 5.02 inches, about 5.03 inches, about 5.04 inches, about 5.05 inches, about 5.06 inches, about 5.07 inches, about 5.08 inches, about 5.09 inches and about 5.10 inches), and in some embodiments barrier plate 25 has a footprint width of between about 3.3 and about 3.4 inches (e.g., length of about 3.30 inches, about 3.31 inches, about 3.32 inches, about 3.33 inches, about 3.34 inches, about 3.35 inches, about 3.36 inches, about 3.37 inches, about 3.38 inches, about 3.39 inches, and about 3.40 inches), as measured from edge to edge across the appropriate dimension (e.g., length dimension or width dimension). In embodiments configured to dispense 96 pipette tips, the pipette tip center to center distance, which conforms with the center to center distance of many commercially available pipette tip racks, is in the range of between about 0.35 to about 0.36 inches. In embodiments configured to dispense 384 pipette tips, the pipette tip center to center distance, which also conforms with the center to center distance of many commercially available pipette tip racks, is in the range of about 0.17 inches to about 0.18 inches. Pipette tips often are dispensed in an array compatible with a wide variety of commercially available pipette tip holders by devices described herein.

In some embodiments, a distal barrier plate can be configured as a one-piece plate, and in certain embodiments a distal barrier plate can be configured as a two-piece plate. A one-piece distal barrier plate embodiment is illustrated in FIGS. 10A-10E. Distal barrier plates configured as a two-piece plate sometimes comprise a base plate or carrier plate (see FIG. 3A-3B) operably connected to a barrier plate or a plate with the functionality of a barrier plate (e.g., a plate with optional tails that provides the functionality of the distal barrier plate (see FIG. 1A and FIG. 2A)). The optional tails are pointed upward in FIGS. 1A-1D and 2A-2C, and pointed downward in FIGS. 10A-10E. The tails of the distal barrier plate normally point downward in an assembled, functional cartridge for an automated pipette tip loading device.

In some one-piece embodiments, the distal barrier plates comprise bores through which the connector rods are disposed. In certain embodiments, the barrier plate bores can be threaded. Threaded barrier plate bores allow rotation of the connector rods, thus enabling translation of the barrier plate and activator plate toward one another. The mode of action of barrier and activator plate movement is described below. In certain two-piece distal barrier plate embodiments, the bores or threaded bores, through which the connector rods are disposed, can be part of the base plate described in further detail below. In some embodiments, bores of a distal barrier plate are substantially smooth.

In some embodiments, the vertical spacing between the top of the barrier plate 25 and the top of the loading block 7 below it, may be configured such that the most distal end or distal portion of a pipette tip 50, which is more distal to the optional tails 21 of the barrier plate 25, is disposed within a hole of a loading block 7 so long as that loading block is engaged with the moving plate 3 of the housing (see FIG. 8A). In this arrangement, the pipette tips 50 are preloaded into the holes of the loading block 7. After being ejected from the barrier plate 25 passing through the channels 18 and past the optional tails 21, the pipette tips 50 will continue down into the holes of the loading block 7. Such distal tip engagement of the pipette tips into the holes of the loading block 7 reduces or prevents potential jams or mis-feeds of the pipette tips after ejection from the channels 18 of the barrier plate 25.

FIGS. 1, 2 and 10 illustrate an embodiment of a pipette tip dispensing device distal barrier plate 25 having a plurality of channels 18, where each channel has a diameter larger than the widest portion of a pipette tip, which can be the major outer transverse dimension 58 of a pipette tip or the largest outer diameter of the proximal portion of a pipette tip. The barrier plate 25 in FIGS. 1, 2 and 10 has a substantially flat top surface 23, and a substantially flat bottom surface 29 that optionally has a plurality of tails 21 around some or all of channels 18. The bossed arrangement of substantially flat surface 29 having a thickness 33 in conjunction with substantially flat surface 19 is optional, and surface 29 may be continuous to the perimeter of the plate in some embodiments with no bossed region. FIG. 1B illustrates optional tails 21 extending in a nearly perpendicular orientation from the flat bottom surface 19. The tails 21 around each channel 18 contact the pipette tip, and optionally deflect outwards against the proximal portion of a pipette tip, when a pipette tip is dispensed and passes by the tails 21, thereby imparting a frictional force on the pipette tip when it is dispensed. Distal barrier plate 25 sometimes also includes optional tails 21 with inner surface 31 and optional pins 17.

Figure 1B:
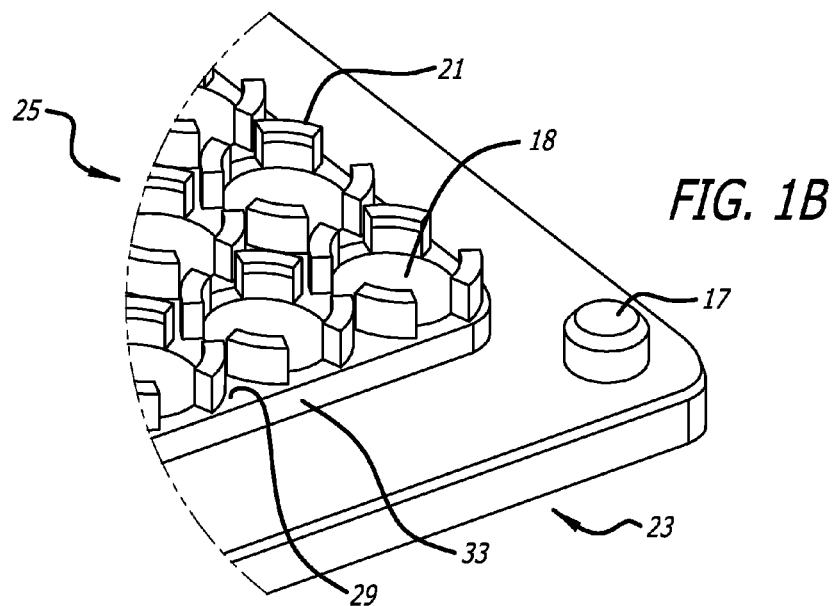
FIG. 1B shows an enlarged cut away view of FIG. 1A (see arrows in FIG. 1A) detailing the optional tails.
Figure 1C:
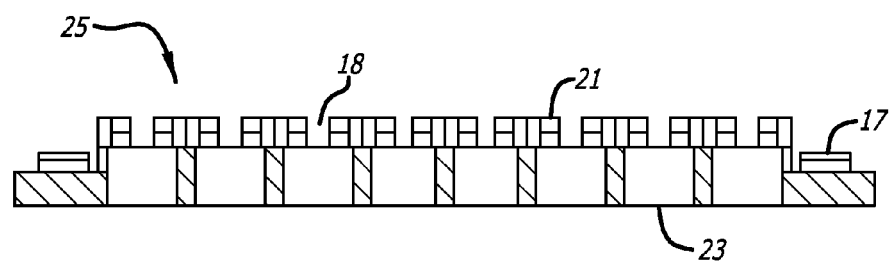
FIG. 1C shows a lateral partial profile view of the tails, where all the tails are the same length.
Figure 1D:
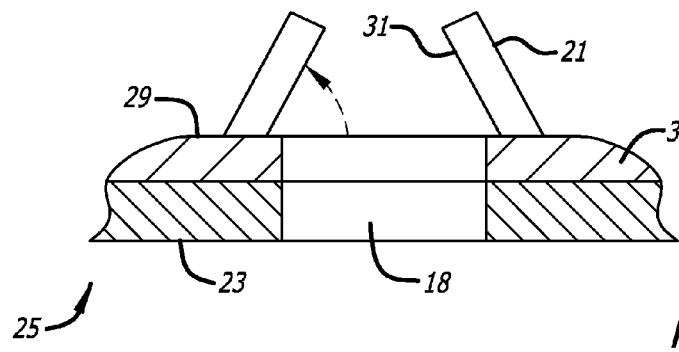
FIG. 1D shows an enlarged cut away, lateral partial profile view of one channel, where the tails are angled.
Figure 2A:
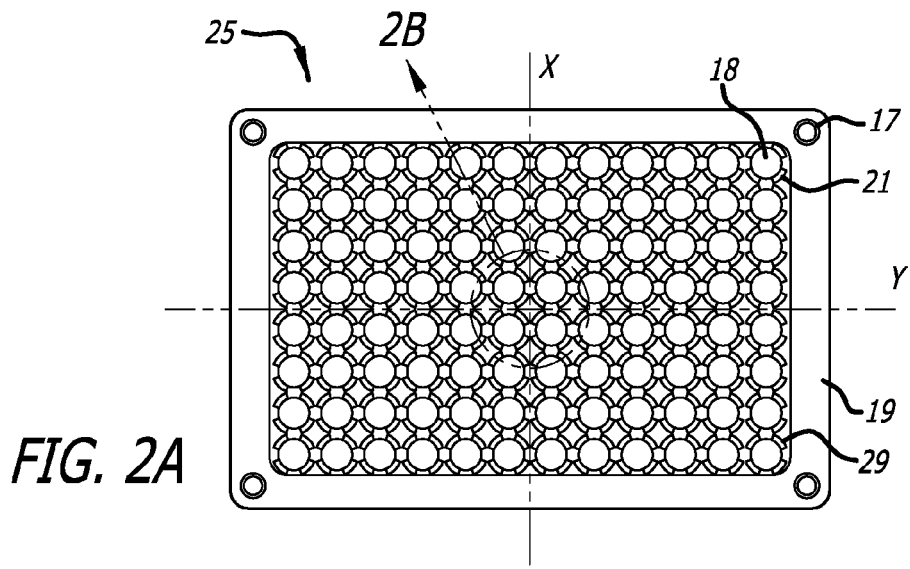
FIG. 2A shows a bottom view of a distal barrier plate with optional tails arranged in a nearly perpendicular orientation with respect to the bottom surface of the plate.
Figure 2B:
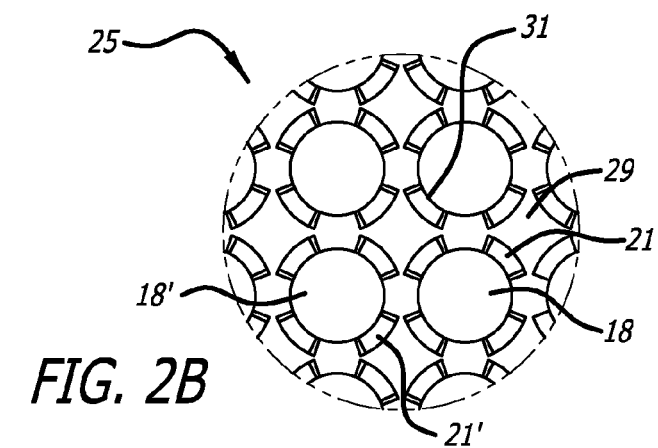
FIG. 2B shows an enlarged cut away view of FIG. 2A (see arrows in FIG. 2A) detailing certain aspects of tails and their orientation to channels.
Figure 2C:
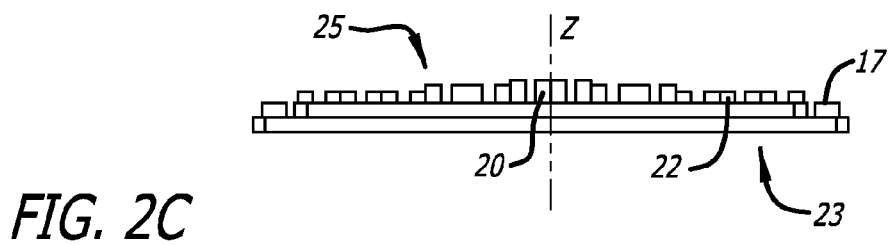
FIG. 2C shows a lateral profile view of the optional tails, where the tails are varied in length.
Figure 10A:
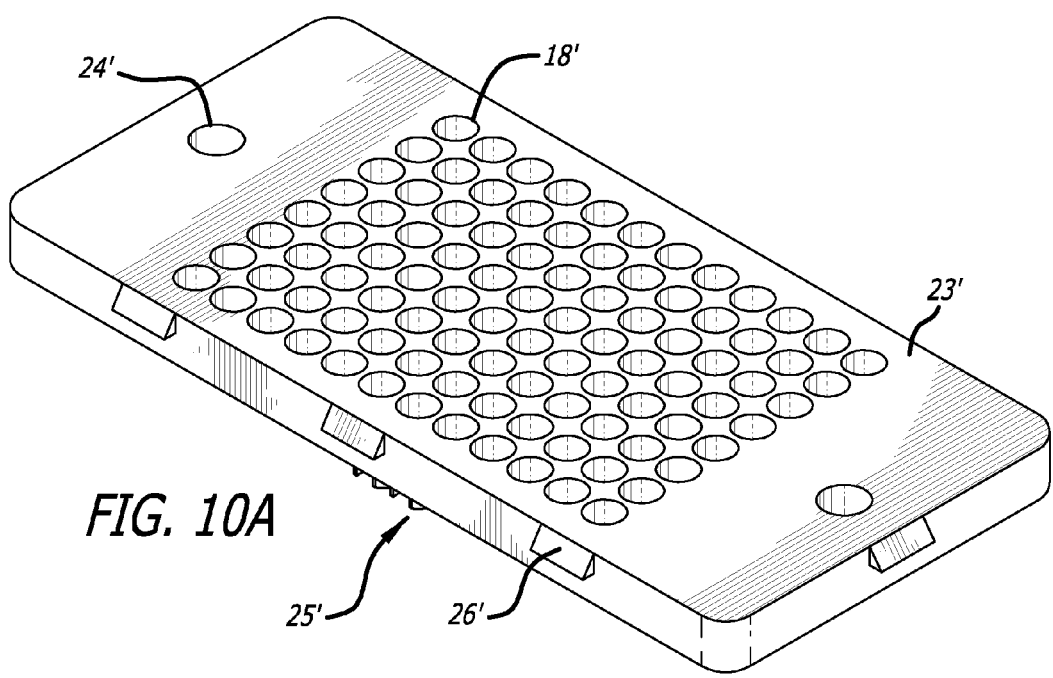
FIG. 10A shows a perspective view of a distal barrier plate.
Figure 10B:
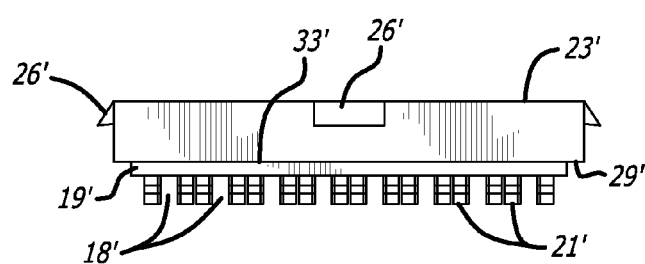
FIG. 10B shows a width side view of a distal barrier plate.
Figure 10C:
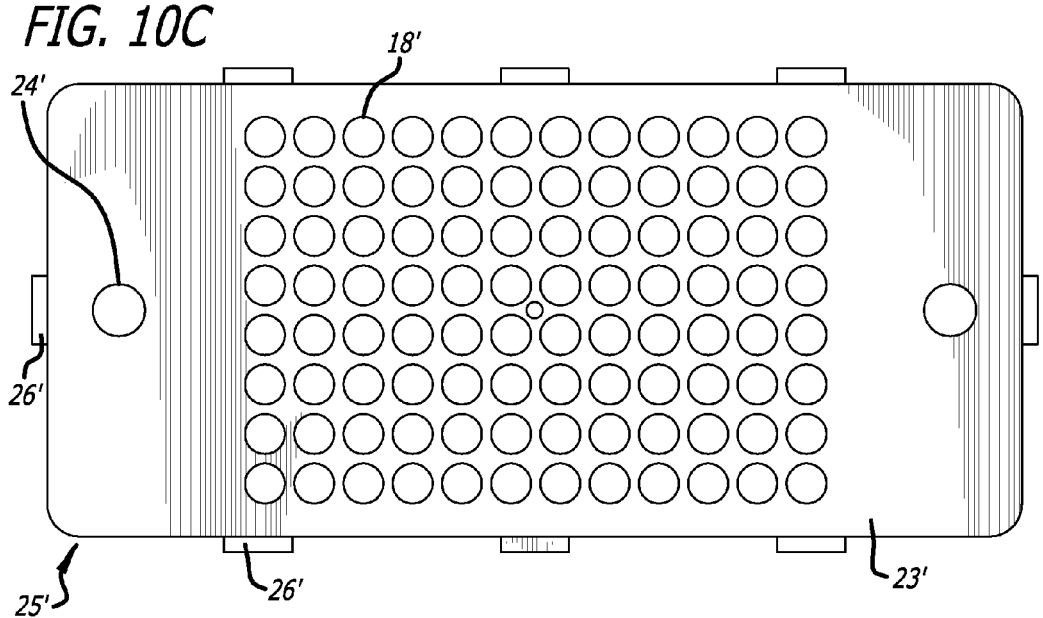
FIG. 10C shows a top view of a distal barrier plate.
Figure 10D:
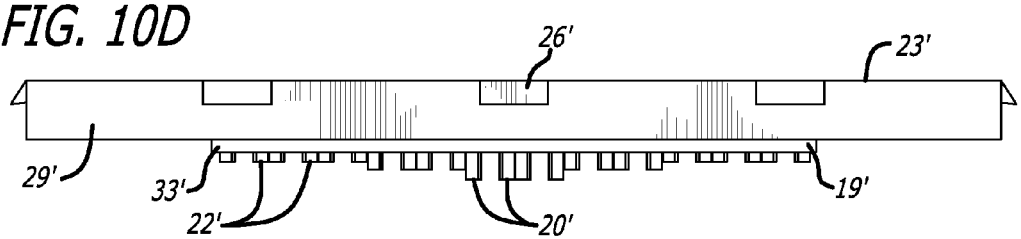
FIG. 10D shows a length side view of a distal barrier plate.
Figure 10E:
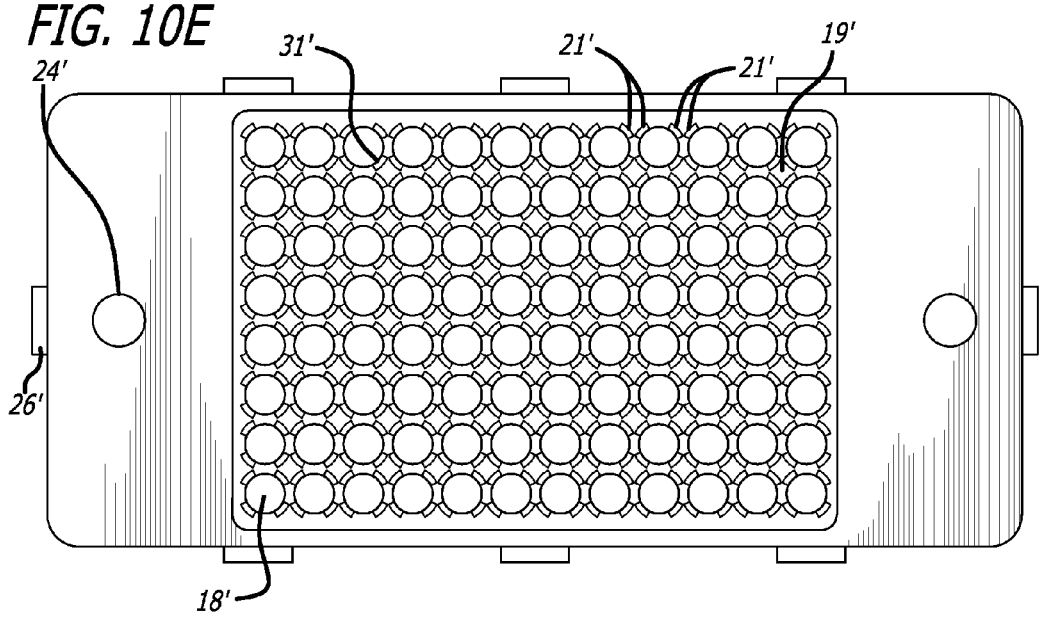
FIG. 10E shows a bottom view of a distal barrier plate.
Figure 11A:
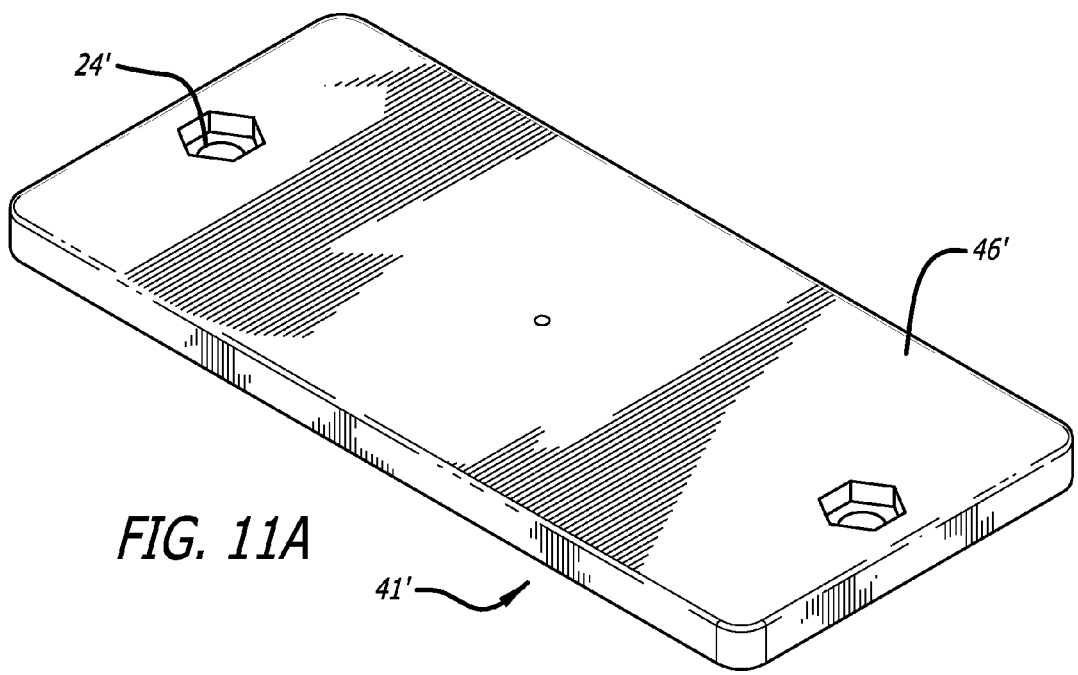
FIG. 11A shows a perspective view of an activator plate, also referred to herein as an actuator plate.
Figure 11B:
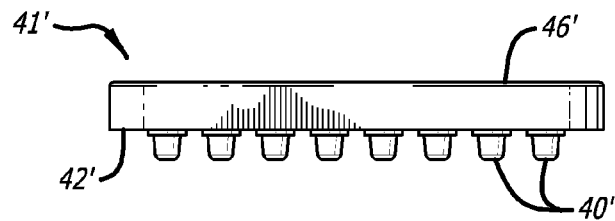
FIG. 11B shows a width side view of an activator plate.
Figure 11C:
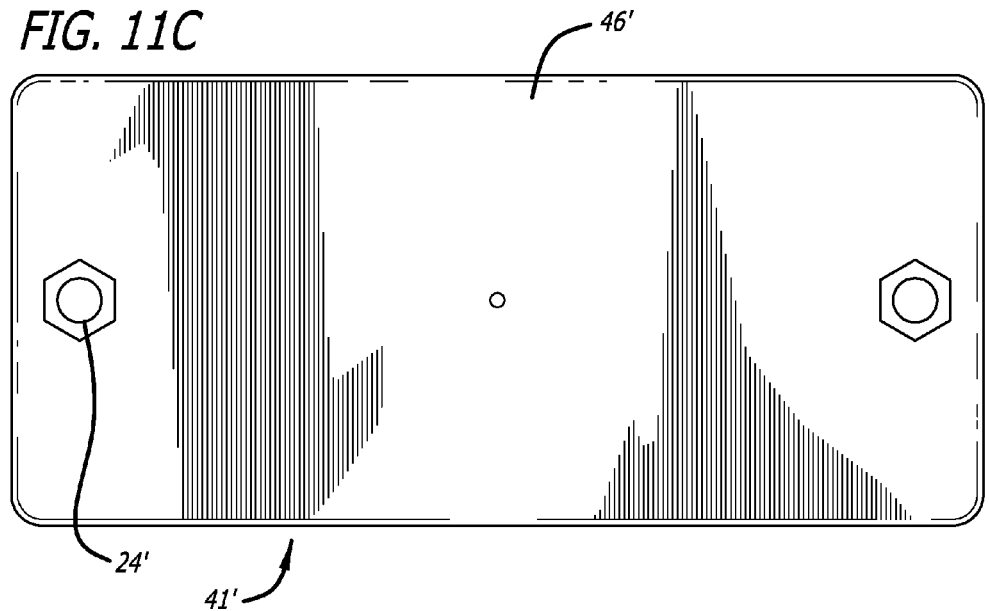
FIG. 11C shows a top view of an activator plate.
Figure 11D:
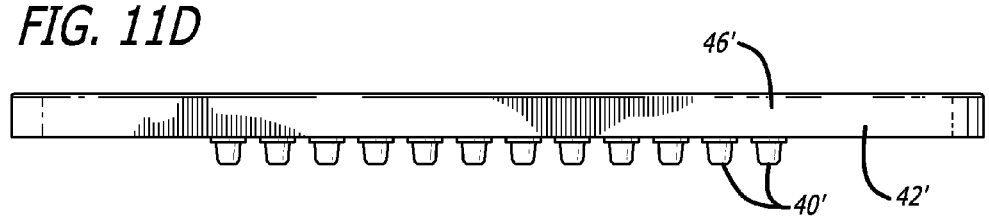
FIG. 11D shows a length side view of an activator plate.
Figure 11E:
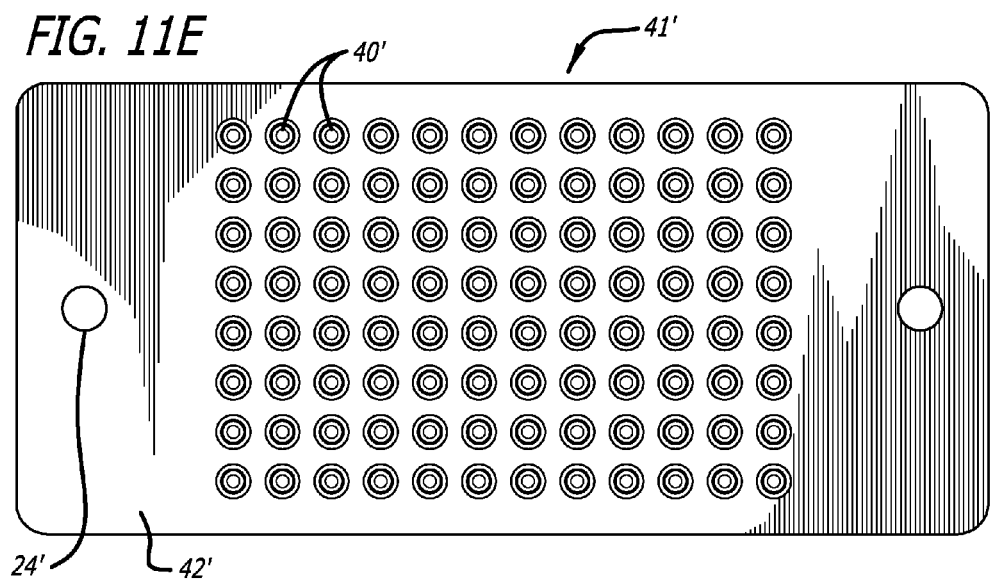
FIG. 11E shows a bottom view of an activator plate.

Each channel optionally can have 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 or more tails. FIGS. 1, 2 and 10 illustrate an embodiment of the barrier plate having four tails 21 per channel. FIG. 1 illustrates an embodiment of the barrier plate where each channel of the barrier plate comprises tails of the same length. FIG. 1B shows an enlarged view of each channel with tails of the same length. FIG. 1C shows a profile view of the tails 21 where they are all of the same length in the barrier plate. FIGS. 2C and 10D show an example of channels of the barrier plate having tails of different lengths, where tail 20 is longer than tail 22. Channels located in the center of the barrier plate can also be the longest tails, as seen in FIGS. 2C and 10D. Subsequent channels concentrically disposed about a central longitudinal axis can have sequentially shorter tails in length in a stepwise manner, also seen in FIG. 2C. FIGS. 10A-10E also show a barrier plate embodiment having tails of different lengths surrounding a channel. In some embodiments channels located in the center of the barrier plate can have the shortest tails, which are not shown in the drawings. And in certain embodiments, subsequent channels concentrically disposed about a central longitudinal axis can have sequentially longer tails in length in a stepwise manner.

Downward movement of the pipette tips within the housing unit often is achieved by pressure or force, not gravity in most embodiments, and downward movement often is actuated by a user. In some embodiments, downward force or pressure often begins with user-induced activation on the actuator plate, with the pressure or axial force greatest at the sides of the plate. In certain embodiments, downward force or pressure sometimes begins with the arrival or detection of a pipette tip rack or holder in the appropriate position to receive pipette tips. The pressure or axial force then spreads peripherally to the center of the activator and distal barrier plates.

A user may actuate the device several times, unloading or ejecting an array of pipette tips from the bottom of the distal barrier plate each time. Pipette tips may be dispensed until, for example, the device is empty of pipette tips and/or insufficient axial force is placed on the device, for example.

It has been determined that providing a distal barrier plate that releases pipette tips in an array at different times can be advantageous. A distal barrier plate in which all channels have the same frictional profile ejects all tips of an array at the same time, which requires a particular actuating force by the user or operator, referred to hereafter as total force or "$F_T$." A distal barrier plate in which some channels have a different frictional profile compared to other channels, however, ejects tips in an array at different times. Without being limited by theory, a portion of force $F_T$ first ejects one subset of pipette tips in the array through channels having a first frictional profile, and another portion of $F_T$ then ejects a second subset of pipette tips in the array through channels having a second frictional profile. Thus, releasing tips in an array at different times effectively spreads out $F_T$ over time, and effectively reduces the actuating force required to eject tips of an array at any one point of time.

The term "same frictional profile" as used herein refers to channels in a distal barrier plate that apply the same frictional force to pipette tips in an array for the same amount of time. The term "different frictional profile" refers to a channel in a distal barrier plate that applies a different frictional force and/or applies the same or different frictional force to a pipette tip for a different amount of time, as compared to another channel in the plate.

In some embodiments, a distal barrier plate includes a subset of channels that ejects pipette tips at a rate different than another subset of channels. In certain embodiments, a distal barrier plate includes 2 to 100 different subsets of channels, each of which eject a pipette tip of one array at a different time (e.g., 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 different subsets). Thus, a distal barrier plate can include 2 to 100 different subsets of channels, each of which have a different frictional profile. The time lapse between the time one set of tips is released from one subset of channels to the time another set of tips is released from another subset of channels can be between about 0.00001 seconds to about 5 seconds (e.g., 0.0001, 0.001, 0.01, 0.1, 1 second), and the total time required to eject pipette tips in an array can vary from about 0.001 seconds to about 5 seconds (e.g., 0.01, 0.1, 1 second). In some embodiments, a distal barrier plate is provided in which all channels have the same frictional profile and all dispense pipette tips at the same time.

In some embodiments, pipette tips at or near the center of a distal barrier plate eject first, and pipette tips near the edge of a distal barrier plate eject last. In certain embodiments, subsets of channels disposed in a linear and/or radial orientation away from the center to the periphery of the plate sequentially eject tips at progressively increasing times.

In certain embodiments, pipette tips at or near the center of a distal barrier plate are ejected last, and pipette tips at or near the edge of a distal barrier plate are ejected first. In such embodiments, subsets of channels disposed in a linear and/or radial orientation from the periphery of the plate to the center of the plate sequentially eject tips at progressively increasing times.

Where it is noted herein that a channel applies a particular frictional force to a pipette tip for particular period of time, the channel periphery or channel walls may apply a frictional force to the pipette tip. Often, however, a feature outside a channel applies a frictional force to the pipette tip (e.g., projections or tails around a channel in connection with a top and/or bottom surface of the plate).

Certain features of a distal barrier plate can apply a particular frictional force to a pipette tip. For example, channel features, including but not limited to channel diameter; channel texture; the presence or absence of one or more projections in the channel (e.g., connected to a channel interior wall); the shape, size, length, thickness, width, rigidity, texture, and/or angle of one or more projections in a channel; or combination of the foregoing, can affect the frictional force applied to a pipette tip as it is ejected. Also, the presence or absence of one of more optional projections outside a channel (e.g., connected to top and/or bottom surface of a distal barrier plate); the shape, size, length, thickness, width, texture and/or angle of one of more projections outside a channel, or a combination of the foregoing, can affect the frictional force applied to a pipette tip as it is ejected.

Any suitable number of optional projections can be present around or near a channel, including without limitation about 1 to about 50 projections. Projections can contact one or more surfaces of a pipette tip, in some embodiments. Projections can contact the widest portion (e.g., largest diameter portion) of a pipette tip (e.g., proximal region portion), and sometimes do or do not contact lower diameter portions of a pipette tip (e.g., distal region portion). Projections sometimes flex against a portion of a pipette tip (e.g., proximal region portion) when the pipette tip is dispensed past the projections. Projections in some embodiments are elastic, and can return to about the same position after a pipette tip is ejected. Projections in connection with the top surface or bottom surface of a distal barrier plate sometimes are referred to herein as "tails," as described herein.

The length of an optional projection (e.g., tail) can affect the time at which pipette tips are ejected. Without being limited by theory, tails having a relatively longer length apply a frictional force for a longer period of time and result in a tip ejection time that is longer than for relatively shorter tails. FIGS. 2A and 2C show channels located in the center of the barrier plate along the X axis can have tails of the same length and channels along the Y axis can have tails of varying length. In some embodiments, channels located in the center of the barrier plate along the Y axis can have tails of the same length and channels along the X axis can have tails of varying length or channels located in the center of the barrier plate along the X and Y axes comprise tails of varying length, which is not shown. Channels can have an even or odd number of tails. For channels having even number of tails, the tails directly opposite one another around a channel can have the same length. And in certain embodiments tails directly opposite one another around a channel can have a different length. Tails adjacent to one another can also have a different length. The tails can be between 0.01 μm-2.0 mm in length. The tails can be between 0.05 μm-2.0 mm in length. The tails can be about 0.01, 0.02, 0.03, 0.04, 0.05, 0.06, 0.07, 0.08, 0.09, 0.1, 0.12, 0.14, 0.16, 0.18, 0.2, 0.22, 0.24, 0.26, 0.28, 0.30, 0.32, 0.34, 0.36, 0.38, 0.4, 0.42, 0.44, 0.46, 0.48, 0.5, 0.52, 0.54, 0.56, 0.58, 0.6, 0.62, 0.64, 0.66, 0.68, 0.7, 0.72, 0.74, 0.76, 0.78, 0.8, 0.82, 0.84, 0.86, 0.88, 0.9, 0.92, 0.94, 0.96, 0.98, 1.0, 1.2, 1.4, 1.6, 1.8, or 2.0 mm in length, in certain embodiments. A distal barrier plate in some embodiments may include tails having different lengths at different channels (e.g., tails around a first channel have a first length, and tails around a second channel have a second length). For example, in certain embodiments the length of tails for each channel progressively increases or decreases (i) from the center of the X-axis to each end of the X-axis and/or (ii) from the center of the Y-axis to each end of the Y-axis. As used herein, the term "progressive" refers to linear, stepwise, sigmoidal, and exponential, in particular embodiments.

The internal angle of optional projections or tails also can affect the time at which pipette tips are ejected. For example, a relatively smaller internal angle for tails or projections can result in a relatively longer time required to eject a pipette tip. The term "internal angle" as used herein with respect to a tail around a channel is an angle measured from the midpoint of a channel at the bottom surface of the plate towards the tail surface facing the channel (e.g., surface 31 in FIG. 1D), as illustrated in FIG. 1D as angle theta. For example, an internal angle of 90° from the bottom surface 19 of the distal barrier plate would be exactly parallel to the Z axis as shown in FIG. 1C. Tails of the barrier plate often are nearly perpendicular with respect to, and often are at an internal angle of almost 90° from, the bottom surface 19 of the distal barrier plate. In some embodiments, tails 21 are at an internal angle of about 89° to about 80° from the bottom surface 19 of the distal barrier plate. Tails can be at an internal angle between 88-85°, 87-84°, 86-83° or 86-85° from the bottom surface of the distal barrier plate. Tails are at an internal angle of about 87° from the bottom surface of the distal barrier plate in some embodiments. A distal barrier plate in some embodiments may include tails having different angles at different channels (e.g., tails around a first channel have a first internal angle, and tails around a second channel have a second internal angle). For example, in certain embodiments the internal angle of tails for each channel progressively increases or decreases (i) from the center of the X-axis to each end of the X-axis and/or (ii) from the center of the Y-axis to each end of the Y-axis.

Texture of the optional tails or projections can affect the time required to eject a pipette tip from a distal barrier plate. In some embodiments, texture can modulates the length, thickness or angle of a tail. Tails can comprise smooth surfaces in some embodiments, and in certain embodiments, tails can comprise texture on one or more surfaces. A tail can be entirely smooth, may be entirely textured, or may include textured and smooth surfaces, in some embodiments. A plate can comprise tails that are smooth and some tails that comprise texture. Tail texture can include, without limitation, ridges, barbs, grooves, grains, embossed, etches, pores, pits, lines, scratches, scores, scrapes, cuts, carvings, incisions and the like. Tail texture can increase frictional force on pipette tips moving past the tails when dispensed. Texture also can aid in channeling pipette tips through the tails and into a loading block (e.g., linear or twisted grooves (e.g., rifled grooves) extending from a tail top to tail bottom). A distal barrier plate in some embodiments may include tails having different textures at different channels (e.g., tails around a first channel have a first texture that applies a first frictional force to pipette tips, and tails around a second channel have a second texture that applies a second frictional force to pipette tips). For example, in certain embodiments the texture of tails for each channel progressively increases or decreases the frictional force (i) from the center of the X-axis to each end of the X-axis and/or (ii) from the center of the Y-axis to each end of the Y-axis.

Optional tails around a channel often are not in the channel, and the portion of a tail joined to the distal barrier plate bottom surface sometimes is co-extensive with the edge of a channel. In some embodiments, the base portion of a tail joined to the distal barrier plate bottom surface is displaced a distance from the channel perimeter that it surrounds, which distance can be a mean, nominal, average or maximum distance of about 0.001 millimeters to about 2 millimeters (e.g., the portion of the tail closest to the channel perimeter that the tail surrounds is offset 0.005, 0.01, 0.05, 0.1, 0.5 or 1 millimeters from the perimeter). The term "displaced" as used herein with respect to tail orientation refers to displaced away from channel perimeter such that the tail base is partially over the channel perimeter, or displaced away from the channel perimeter so that there is a gap between the channel perimeter and the tail base on the plate bottom surface equal to the displaced distance. Thus, the term "surrounds" as used herein with respect to a tail refers to a tail associated with a channel, where the tail base is co-extensive with, or displaced towards or away from, the channel perimeter. For example, tail 21 surrounds channel 18, and tail 21' surrounds channel 18', but tail 21 does not surround channel 18', as shown in FIG. 2B.

Optional tails described herein generally are not prone to breakage as pipette tips are dispensed through a distal barrier plate comprising the tails. Without being limited by theory, the nearly perpendicular orientation of tails with respect to the bottom surface of a distal barrier plate contributes to tail stability, as this orientation requires little flexion of tails to apply a force to the pipette tips. In certain embodiments, the maximum, mean, median or nominal tail flexion is about 0.01 degrees to about 10 degrees (e.g., about 0.05, 0.1, 0.5, 1, 2, 3, 4, 5, 6, 7, 8, 9 degrees). The term "flex outward" as used herein refers to a tail flexing a certain number of degrees added to the internal angle. For example, a tail that flexes outwards by 2 degree adds 2 degrees to the internal angle in the flexed state; if the tail in the unflexed state has an internal angle of 87 degrees, the tail in the flexed state has an internal angle of 89 degrees. In certain embodiments, no more than 1, 2, 3, 4, 5, 6, 7, 8, 9 or 10 tails, or portions thereof, are separated from the distal barrier plate for a set of 480 pipette tips dispensed through the plate.

A tail may have any convenient shape. A surface of a tail can be of a shape that includes without limitation, square, rectangle, rhombus, parallelogram, circle, oval, arced, curved, planar, non-planar, and the like. The thickness of a tail can be continuous or tapered (e.g., tapered towards the top (i.e., in association with the plate) or bottom (i.e., at the tail terminus) of the tail).

Base Plate

Figure 3A:
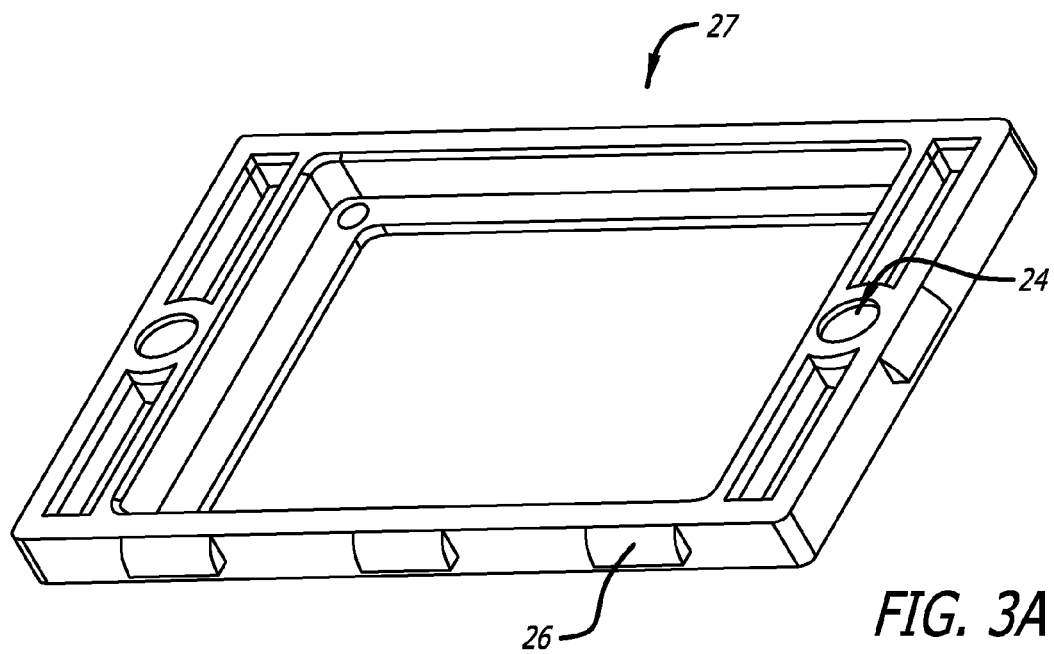
FIG. 3A shows the top surface and FIG. 3B shows the bottom surface.
Figure 3B:
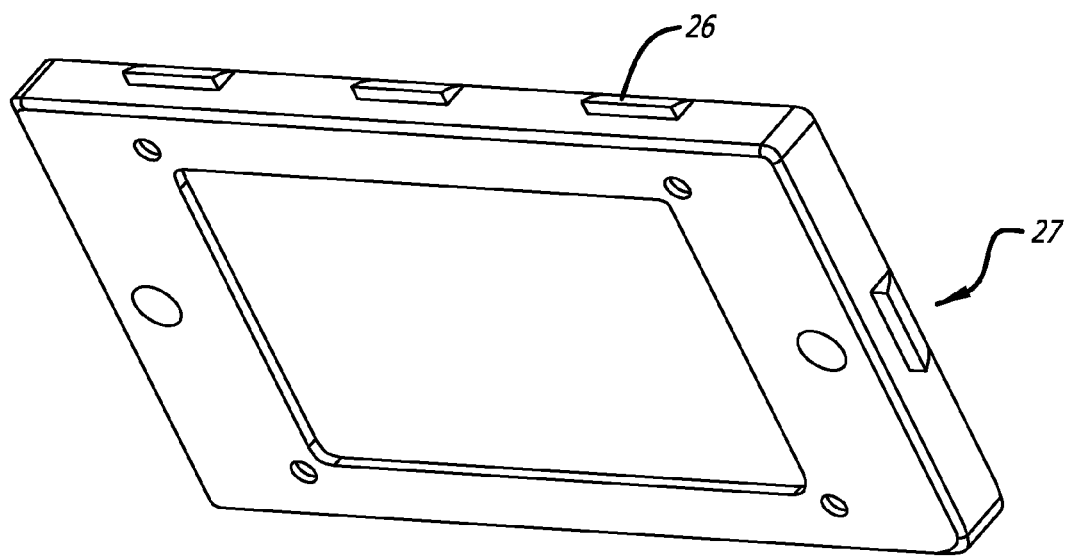

In some embodiments, an automated pipette tip loading device can have a distal barrier plate configured in two pieces, a base plate and a barrier plate. FIGS. 3A and 3B show an optional embodiment for base plate 27 which the distal barrier plate 25 can snap into by pins 17 at the four corners of the barrier plate. The pins 17 match the four holes in the base plate so that the distal barrier plate 25 can be centered in the middle of the base plate 27. One of ordinary skill in the art will recognize other ways the base plate 27 and distal barrier plate 25 can be held together. For example, magnets, guides, fasteners, and buttons can also hold the plates together. The base plate 27 is shown having two holes 24 for placement of rods 28 to connect the distal barrier plate 25 and actuator plate 41. In certain embodiments, the distal barrier plate and the base plate are formed into one plate serving both functions. A one piece distal barrier plate/base plate embodiment is illustrated in FIGS. 10A-10E.

FIG. 3A shows the proximal surface of the base plate and FIG. 3B shows the distal surface of the base plate. The base plate 27 also has prongs 26 which are used in packaging the auto eject cartridge 6. The prongs 26 aid in placement of the disposable, recyclable, rectangular sleeve that covers the auto eject cartridge 6, as seen in FIGS. 8A and 8B, 12A-12H and 14A-14G. The prongs also secure a removable, disposable, recyclable bottom lid, not shown, that protects the pipette tips from damage or contamination during shipment. The lip of the bottom lid slightly telescopes above the prongs to be secured. The bottom lid is removed when the auto eject cartridge is place into the housing unit.

Proximal Actuator Plate

In some embodiments, the proximal actuator plate, also referred to as an "activator plate" (e.g., 41 in FIGS. 5A-5C, also see FIGS. 11A-11E), has a member on the top portion 42 of the actuator that maintains contact with and restricts lateral displacement of the proximal portion 56 of the pipette tips 50. The member can be any material known to one of skill in the art, for example the member can be foam, a raised grid, or a plurality of proximal alignment members 40. As noted above for the distal barrier plate, the raised grid or plurality of proximal alignment members 40, are spaced and configured to conform to the footprint of a pipette tip rack or holder that conforms to American National Standards Institute (ANSI) standard dimensions, accepted by the Society for Biomolecular Sciences (SBS), for devices used in high throughput applications related to the use of microtiter plates (e.g., multi-channel dispensers (manual or automated), pipette tip racks, pipette tips, and the like), in some embodiments.

Figure 5A:
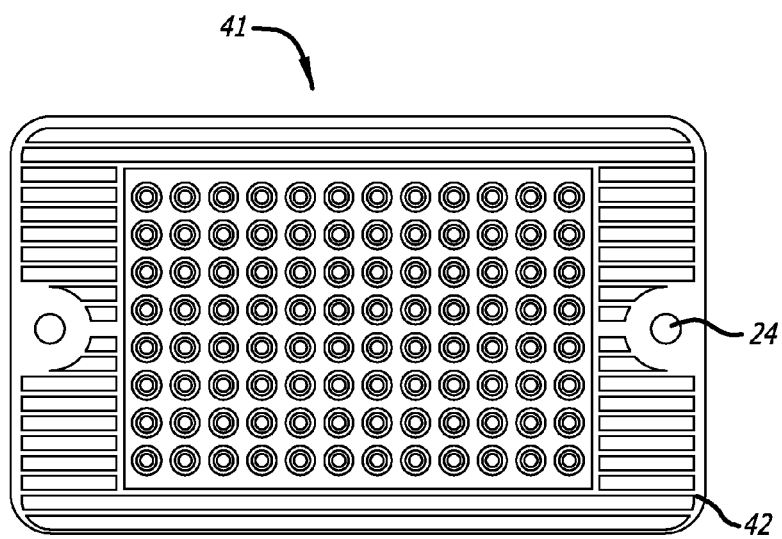
FIG. 5A shows the top portion of the plate.
Figure 5B:
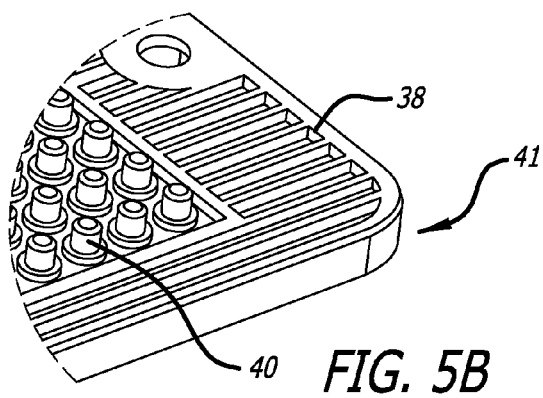
FIG. 5B shows an enlarged corner section of the plate from FIG. 5A.
Figure 5C:
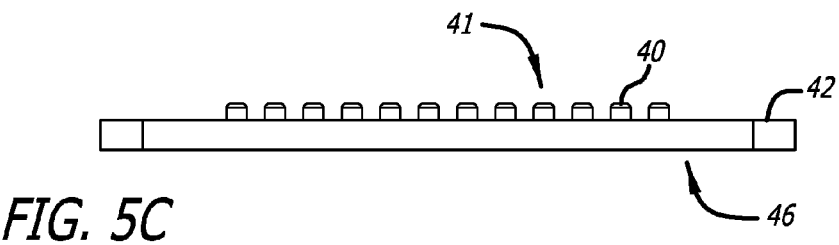
FIG. 5C shows a lateral view of the activator plate in FIG. 5A.

FIGS. 5A-5C (see also FIGS. 11B and 11E) show embodiments with a plurality of proximal alignment members 40 disposed substantially in a plane in a regularly spaced array and each proximal alignment member 40 is configured to releasably engage and restrict lateral displacement of a proximal end 56 of a pipette tip 50 that is engaged with the alignment member 40. The proximal alignment members can be of any convenient shape suitable for engaging and aligning pipette tips held in a nested array in the automated pipette tip loading device. Non-limiting examples of cross-sectional shapes useable for alignment members in actuator plate embodiments described herein include circular, square, star shaped, triangular, cone shape, hexagonal, octagonal, a polygon shape and the like.

In some embodiments, the proximal alignment members 40 may be cone shaped abutments extending from a distal surface of the actuator plate 41 that may be configured to engage or fit within the proximal port of corresponding pipette tips to be used with the proximal actuator plate 41. The proximal actuator plate 41 may be made from suitable metals, such as aluminum, or polymers such as polypropylene, polycarbonate, polyethylene, polystyrene, polyurethane and the like as well as any other suitable polymers that may be molded, thermoformed or the like. The proximal actuator plate 41 and proximal alignment members 40 may be molded from a monolithic structure of the same material for some embodiments. The proximal actuator plate 41 may have a thickness of about 0.05 inches and about 0.25 inches. The proximal actuator plate 41 may be secured to a plurality of rods and may be configured with sufficient rigidity to maintain a generally planar configuration when applying axial force to an array of pipette tips 50 engaged with the proximal members 40 thereof as the pipette tips are being pushed through the tips 21 of the distal barrier plate 25. Some pipette tip array embodiments of the actuator plate 41 and barrier member may include 96 pipette tip arrays of 8×12 pipette tips spaced about 9 mm apart center to center, some other embodiments may include 384 pipette tip arrays of 16×24 pipette tips spaced about 4.5 mm apart center to center. Other pipette tip array embodiments may include more or less pipettes depending on the application.

The proximal actuator plate 41 in FIGS. 5A and 5B (see also FIGS. 11A, 11C and 11E) show two holes or bores 24 for placement of rods 28 to connect the distal barrier plate 25 and actuator plate 41. The holes or bores, 24, through which the connector rods exert a downward force on the actuator plate, sometimes are threaded, and in some embodiments are smooth. In certain embodiments, plate 41 includes a recess configured to receive a threaded nut that engages with a connector rod. A threaded feature in the bore and/or nut in plate 41, in some embodiments, can interact with a threaded connector rod and facilitate displacement of the actuator plate and barrier plate towards each other (e.g., by rotation of the threaded connector rod). The barrier plate often has corresponding bores or threaded bores through which a distal portion of the connector rods translate, enabling the rods to exert an upward force on the barrier plate. The corresponding bores in the barrier plate aid in the displacement of the actuator plate and barrier plate towards each other.

Optionally, the top portion of the actuator plate 41 has ridges or grooves 38 which provide strength and ridgidity to the actuator plate 41. As seen in FIGS. 6A and 6B, the roof portion 46 of the actuator plate also can have ridges or grooves 48 which can also provide strength and ridgidity to the plate. In some embodiments, the roof portion of the actuator plate can have a smooth surface as illustrated in FIGS. 11A, 12A, 14A and 14F.

A force may be effectively applied to an actuator plate in a number of manners. In some embodiments, an actuator plate is pulled downward, and in certain embodiments, an actuator plate is pushed downwards, to dispense pipette tips. In embodiments where a motor effectively applies a force to an actuator plate, the motor may be located in any orientation with respect to the actuator plate, including, for example, above, below or to the side of the actuator plate. The applied force sometimes it the result of rotation of the connector rods through threaded bores and/or threaded nuts in the actuator and distal barrier plates, which in turn mechanically displaces the actuator and distal barrier plates towards each other, as described in further detail below. In embodiments where a threaded nut is utilized, bores in the actuator plate sometimes are smooth.

Connectors

Figure 4:
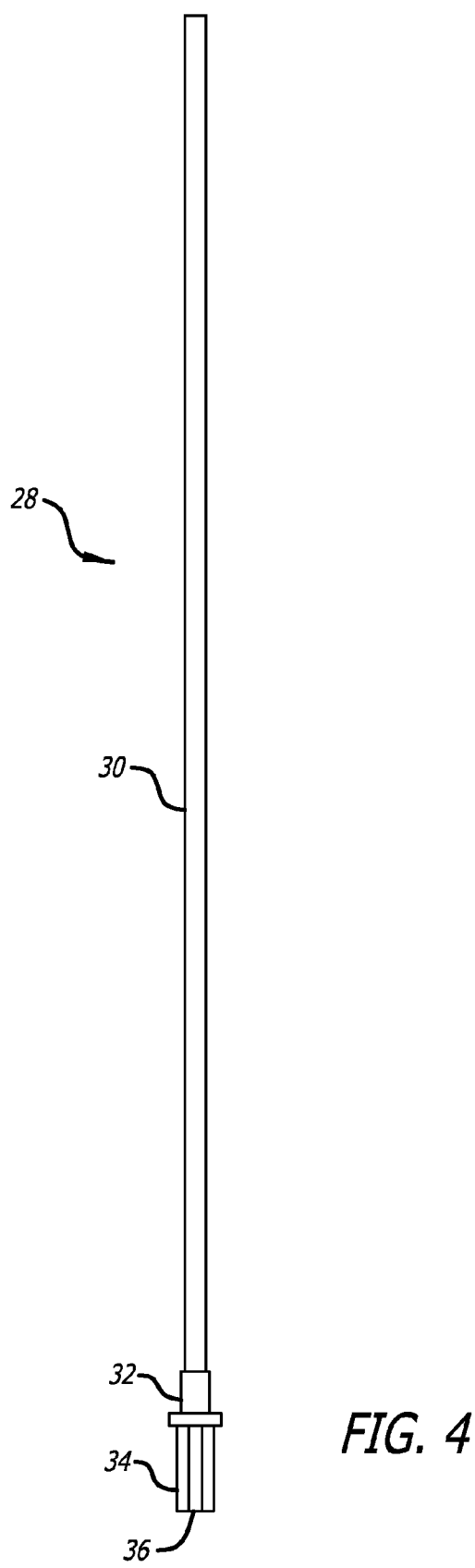
FIG. 4 shows a rod of the automated pipette tip dispensing device.

Referring to FIG. 4, a rod 28 is shown in detail as one embodiment of a connector that connects the actuator plate 41 and distal barrier plate 25. Any suitable connectors that can perform the same or a similar function of connecting actuator plate 41 and distal barrier plate 25 and facilitating displacement of the plates towards each other, can be used. Non-limiting examples of connectors include a bar (rectangular, L-shaped cross section), tube (e.g., telescoping, non-telescoping), piston (e.g., piston in sleeve configuration), spring, chain, vise, crank, screw, lever, dolly, clamp, hook, or grapple can be connectors in some embodiments. A rod has any suitable shape, and can comprise a circle, oval, square, rectangle, rhombus, L-shaped, S-shaped, or parallelogram cross section in some embodiments, and in certain embodiments, can comprise a substantially planar, non-planar or curved surface. Connectors also are illustrated in FIGS. 12A-12E and 12H.

In FIG. 4, the rod has a shaft 30, grommet 32, bolt 34 and a distal portion 36. The shaft 30 of the rod can be threaded. A connector may be movably engaged (e.g., slidably engaged) with a distal barrier plate, and in some embodiments a connector may translate through the distal barrier plate when pipette tips are dispensed. A connector may be fixed while pipette tips are dispensed in some embodiments, and an actuator plate may translate with respect to the connector, in certain embodiments. A connector may rotate, translate vertically (e.g., with respect to a distal barrier plate), ratchet, telescope and the like, or combination of the foregoing, while pipette tips are dispensed, in some embodiments. A connector may be effectively fixed with respect to a distal barrier plate and/or an actuator plate in certain embodiments. A connector may translate with respect to a distal barrier plate and or actuator plate in some embodiments.

Connector Drive System

As noted above, connectors can facilitate translation of the proximal activator plate and distal barrier plate towards each other, thereby dispensing pipette tips into a waiting pipette tip rack or holder. The connectors, illustrated as rods in some embodiments described herein, can be rotated, sometimes by a force imparted by a motor, to cause the required movement of the activator and barrier plates with respect to each other. Bolt 34 and distal portion 36 of connector rods 30 sometimes can be configured to functionally engage a drive mechanism of connector drive system, or robot drive, 70, illustrated in FIGS. 15 and 16.

Figure 15:
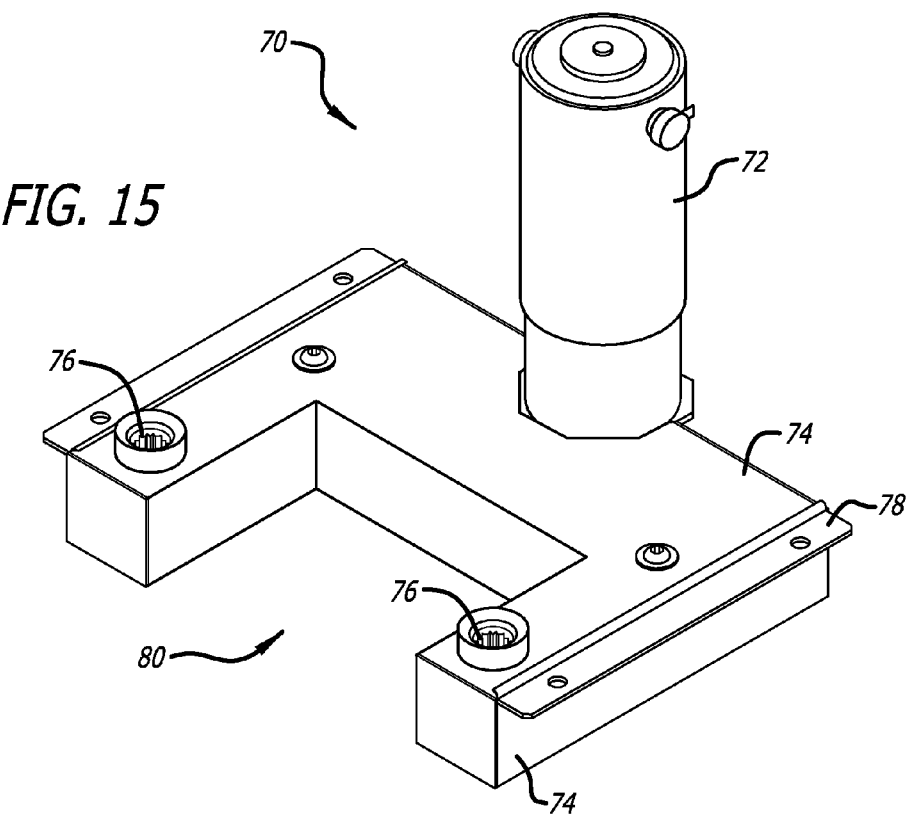
FIG. 15 shows a perspective view of a motor or drive embodiment (e.g., robot drive) utilized to directly or indirectly rotate connector rods that operationally connect the activator and distal barrier plates, and enable the activator and distal barrier plates to vertically translate towards each other to dispense pipette tips into a pipette tip rack or loading block.

Connector drive system or mechanism 70 can include: motor or drive 72, motor base and drive housing 74, connector drive 76, optional mounting system 78 and pipette tip rack staging area cutout 80, as illustrated in FIG. 15. Connector drive system 70 also can include drive belts/chains 82 and 84 and intermediate drive mechanism 86. Motor or drive 72 often provides sufficient energy or force to rotate the connectors through the functional engagement of bolt 34, 34' and connector distal portion 36, 36' with connector drive 76. Any method of transmitting the force of motor or drive 72 to connector drive 76 can be utilized. In some embodiments, force is transmitted directly (e.g., direct connection of motor output to connector drive 76), and in certain embodiments, force is transmitted indirectly (e.g., the output of the motor operates an intermediate drive mechanism 86 that is functionally coupled to connector drive 76). Non-limiting examples of methods for transmitting the force of motor or drive 72 to connector drive 76, directly or indirectly, include gear drives, shaft drives, belt drives, chain drives, the like and combinations thereof. Optional mounting system 78 can be used to secure connector drive system 70 to a frame or housing unit, thereby stabilizing and/or immobilizing connector drive system 70 in an appropriate location to allow functionality of connector drive system 70.

Figure 16:
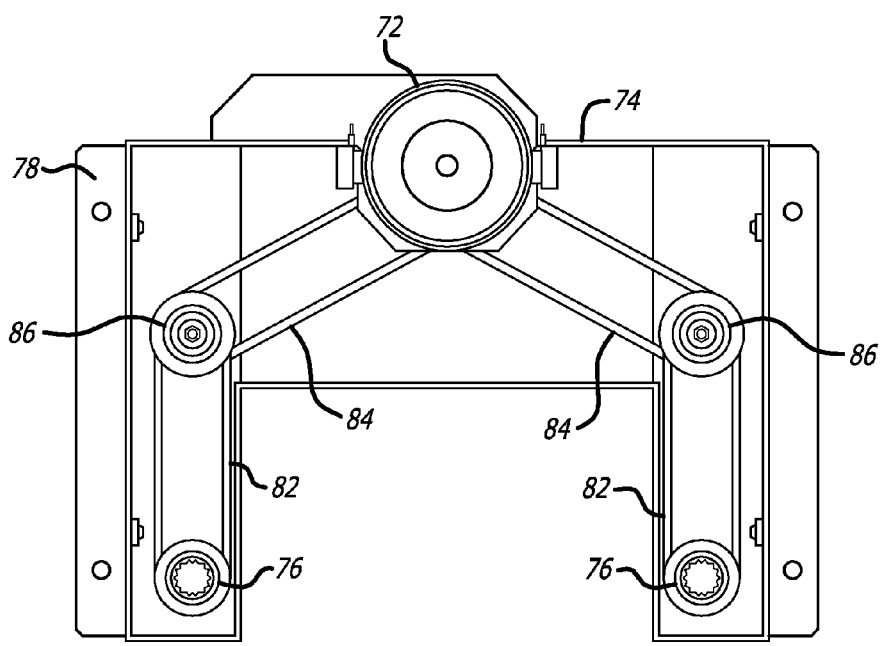
FIG. 16 shows a top view of a drive motor embodiment, with the top covering plate removed to show a non-limiting embodiment of an indirect drive mechanism.

Shown in an embodiment described in FIG. 16 is an indirect force transmission approach, where the force of motor or drive 72 is transmitted using belt system 84 to cause rotation of intermediate drive 86 (e.g., pulley, cam, or gear). The rotation of intermediate drive 86 is translated to rotation of connector drive 76 by the action of a second belt system 82, as illustrated in FIG. 16. Use of indirect force transmission methods as described herein and others available to a user allow the force imparted by a single motor or drive 72 to be split and transmitted to two or more remote locations, with the added benefit of being able to deliver the force to a desired location without the need for a direct path from motor 70 to connector drive 76.

Rotation of connector drives 76 rotates connector shafts 30, 30' via the functional engagement of nut 34, 34' and distal portion 36, 36'. Distal portion 36, 36' sometimes is configured as a nut or bolt to engage socket shaped drive 76, as illustrated in some embodiments provided herein (see FIG. 15). Any suitable pairing of geometries can be selected provided that the chosen shapes are capable of transmitting the required force to translate the plates towards each other, and overcome the frictional force imparted by the plurality of optional tails surrounding each channel in distal barrier plate 25. Non-limiting examples of geometric pairings suitable for use as connector drive 76 and base or distal portion of rod 30, 30' include 3 sided, 4 sided, 6 sided, 8 sided, or 12 sided "nuts" or "bolts" with the corresponding "socket", slots and tabs, pegs and holes, the like or combinations thereof.

Rotation of shafts 30 via connector drives 76, movably translate proximal activator plate 41, 41' and distal barrier plate 25, 25' towards each other, thereby forcing a layer of pipette tips through the channels in barrier plate 25, 25' into a pipette tip rack or holder staged on a platform occupying the space left by drive system cutout 80. Pipette tip racks can be placed manually on a platform or tray placed in drive system cutout 80, in some embodiments. In certain embodiments, an automated platform can insert or remove a pipette tip rack in the appropriate location in drive system cutout 80 to receive dispensed pipette tips as described herein. In some embodiments, the pipette tip dispensing cycle is initiated by the insertion of a pipette tip rack in the receiving position by a manual or automated platform. In certain embodiments, the platform or movable stage moves horizontally, and in some embodiments, the platform or stage moves vertically, into the space left by drive system cutout 80. In certain embodiments, arrival of a platform or movable stage into drive cutout 80 triggers pipette tip dispensing and sterilization cycles.

As noted above, the movement of the platform or stage that holds an empty pipette tip rack or holder can be manually or automatically activated by a user. In certain embodiments, the platform movement is controlled manually by a user-activated switch or level. In some embodiments, the platform movement is automated, and can be activated by a user by a switch or controller, or by placing a pipette tip rack on the moveable platform, which then initiates the pipette tip dispensing and sterilization cycles by automated sensor (e.g., sensor detects the arrival of pipette tip rack, and initiates dispensing and sterilization cycles). In embodiments utilizing an automated platform, the platform movement sometimes is controlled by a motor that can insert the platform into drive system cutout 80. In certain embodiments, motor or drive 72 can be activated by a user controlled mechanism. In some embodiments, a user controlled mechanism is a switch (e.g., lever switch), button, or sensor. In some embodiments, the motor stops rotating the rods by a pressure sensor gauge. In some embodiments, a user is a person or machine (e.g., robot, computer).

Auto Eject Cartridge

Figure 8A:
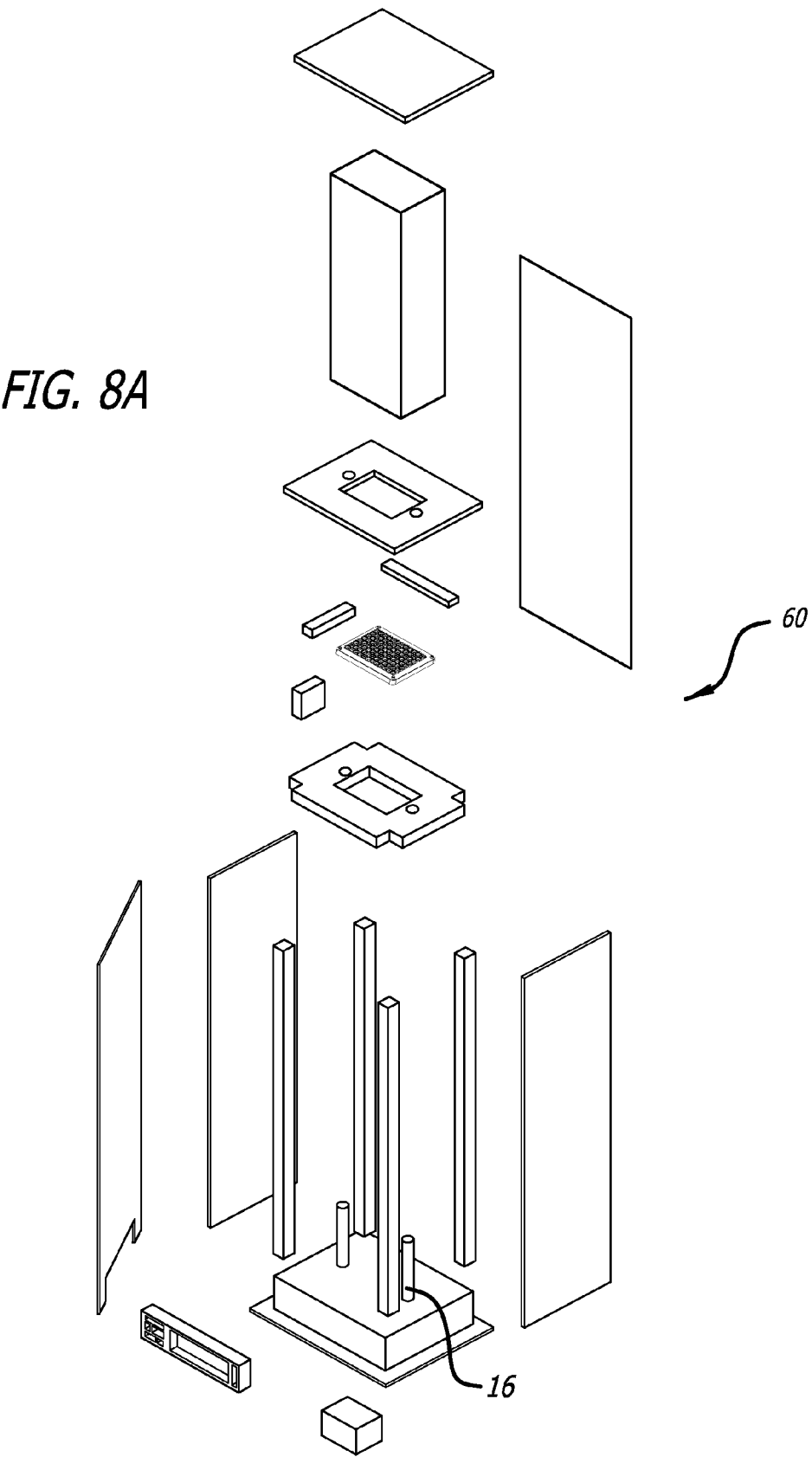
FIGS. 8A and 8B show the assembly of components of the automated pipette tip dispensing device.
Figure 8B:
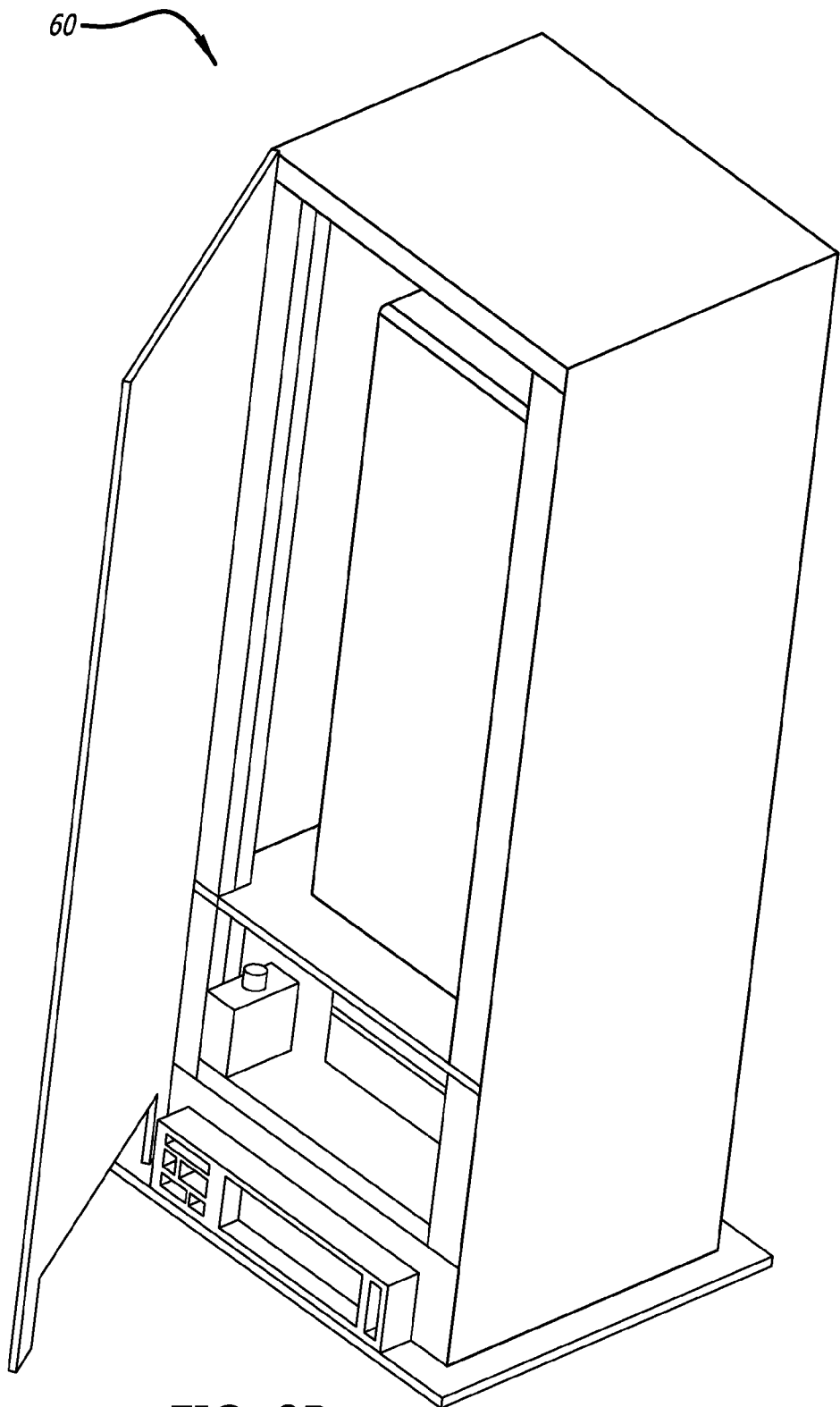
Figure 9A:
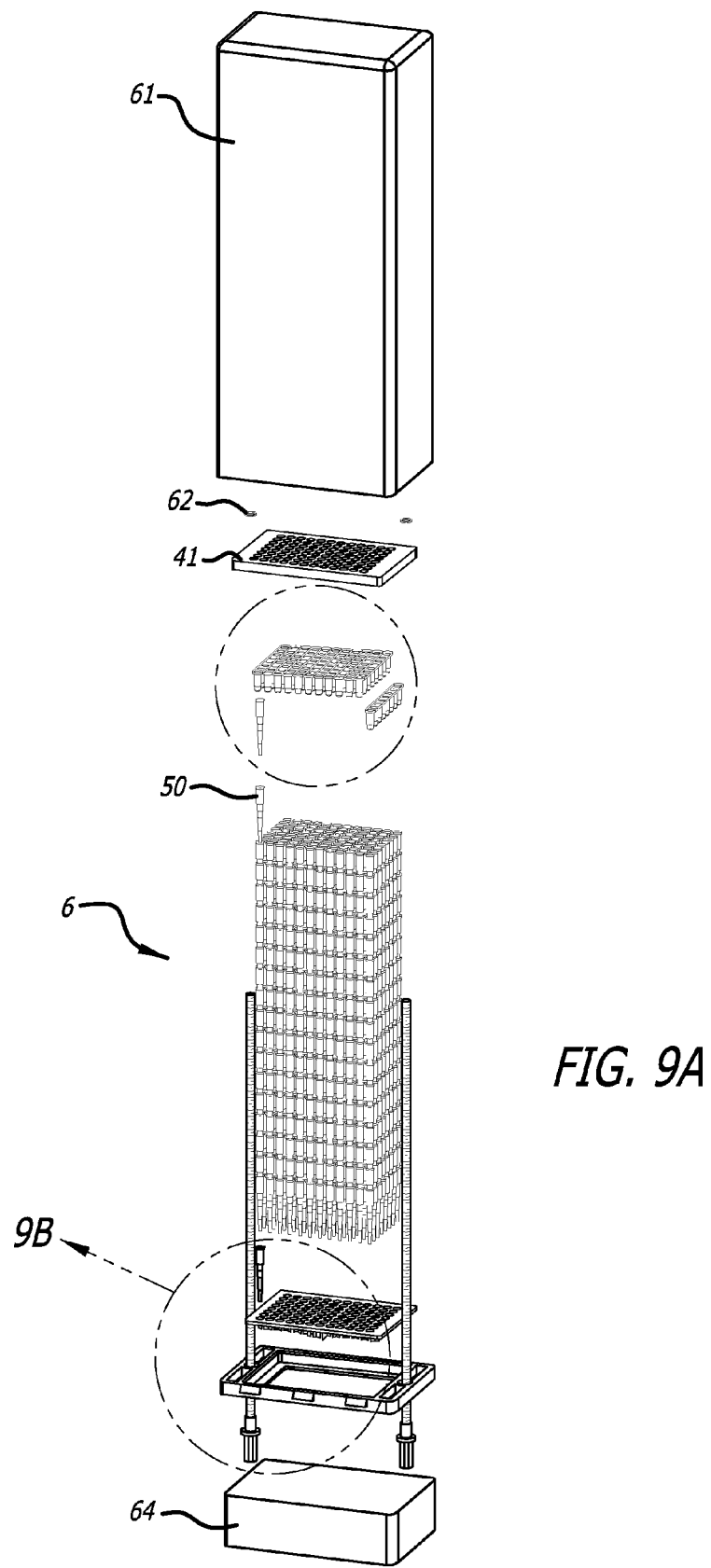
FIG. 9 shows an auto eject cartridge and its components.

An auto eject cartridge (e.g., element 6 of FIGS. 8A, 8B and 9 (see also FIGS. 12A-12H)), often includes several components. In some embodiments, cartridge 6 includes arrays of pipette tips 50, activator plate 41, distal barrier plate 25, base plate 27, rods 28, nuts 62, and rectangular sleeve 61 and bottom lid 64. Aside from the outer sleeve 61 and lid 64, other mechanical components work together in dispensing an array of pipette tips from the bottom of the auto eject cartridge 6 and into the loading block 7 below. Sleeve 61 in some instances may refer to both the sleeve 61 as seen in FIG. 9A and the bottom lid 64 as one storage unit that houses all the components seen in FIG. 9A. In some instances, sleeve 61 only refers to the top and side portions of the sleeve without the bottom lid 64 as seen in FIGS. 8A and 8B. In some embodiments, the distal barrier plate 25 and base plate 27 are one in the same and not two separate components. Together they can be referred to as the distal barrier plate 25, as described below within this section. In some embodiments, connectors of the activator 41 and distal barrier plate 25 are rods 28. The rods 28 can have threads etched into their outer surface such that another threaded component can be securely engaged to it. The activator plate 41 can include threaded members, and each threaded member engages a threaded portion of each rod. 28. Rotation of the rods 28 by a motor can translate the activator plate 41 towards the distal barrier plate 25 by rotation of the rods 28. The motor 13 is activated by a user controlled mechanism. The user controlled mechanism can be a variety of known devices. For example, a controlled mechanism can be a lever switch, button, or sensor. The motor can stop rotating the rods by a pressure sensor gauge after ejection of an array of pipette tips 50 from the distal barrier plate 25.

Figure 12B:
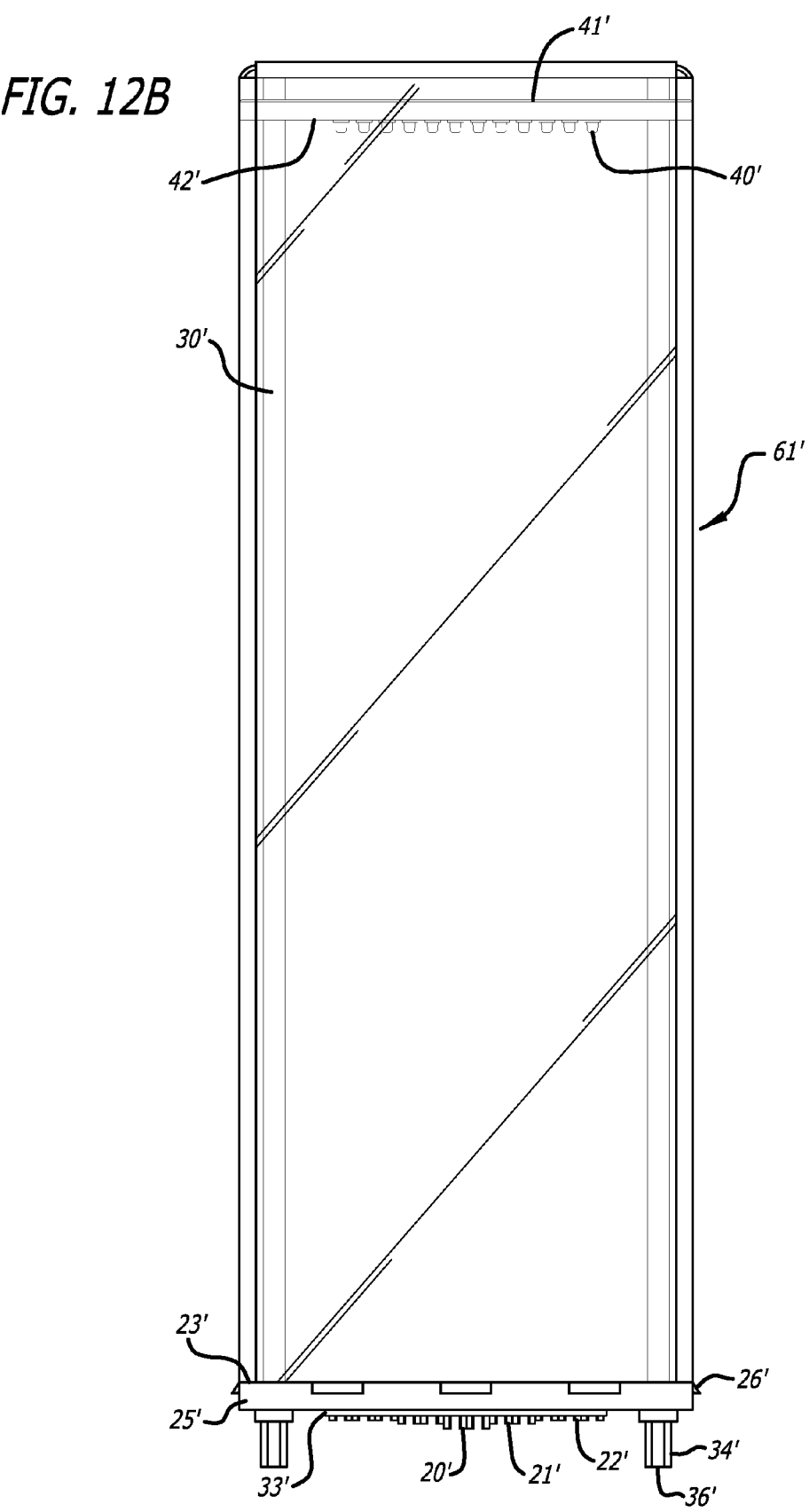
Figure 12C:
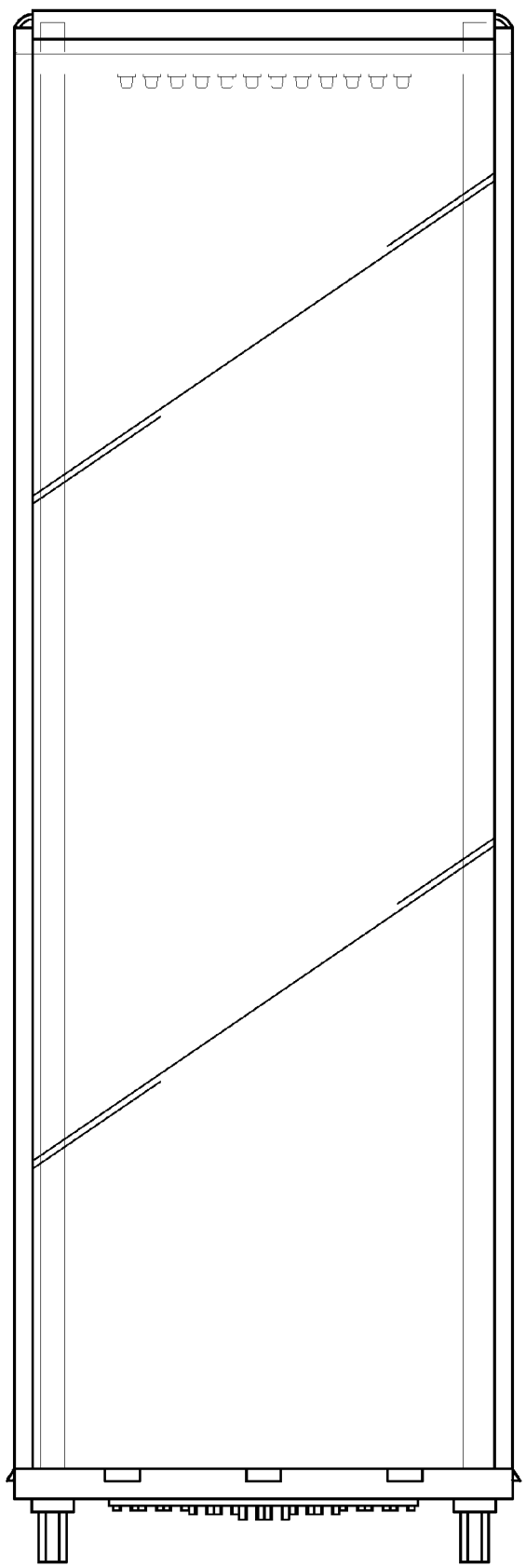
Figure 12F:
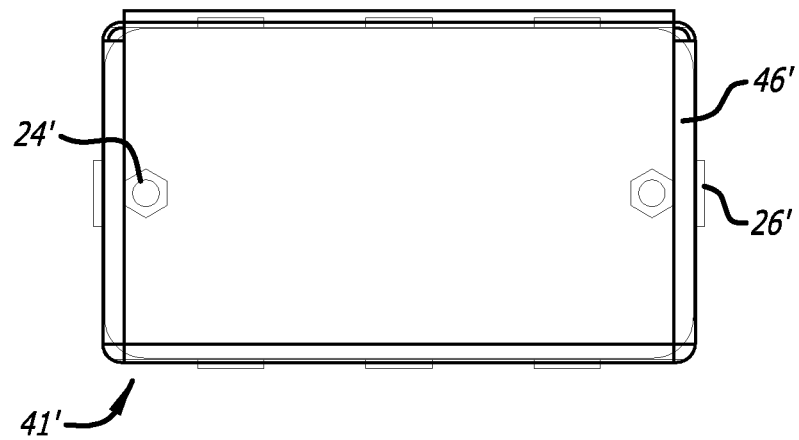
Figure 12G:
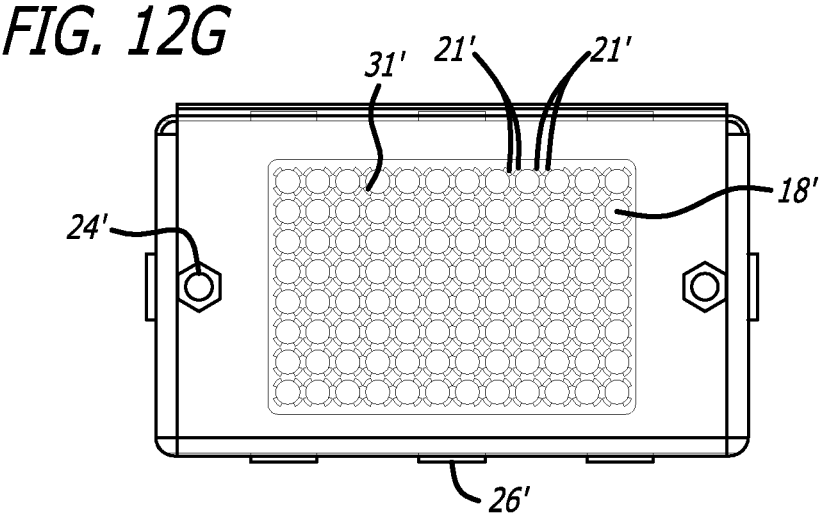
Figure 12H:
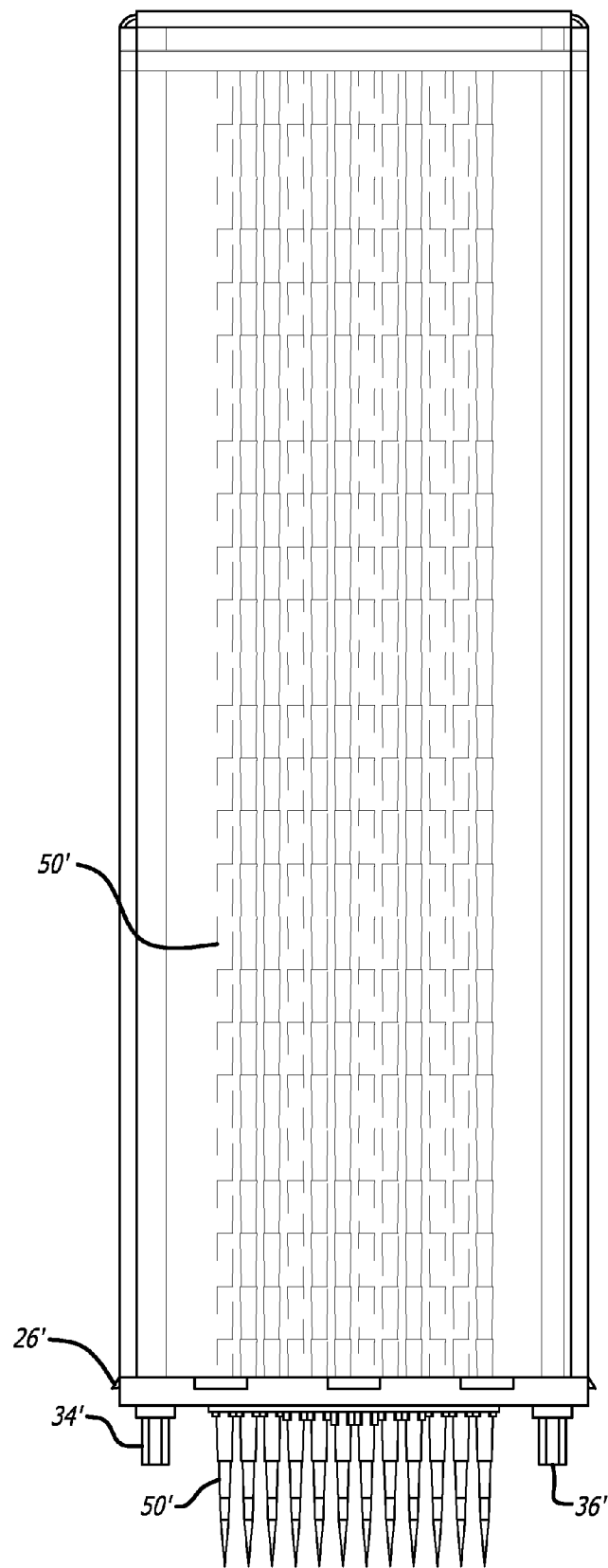
Figure 13A:
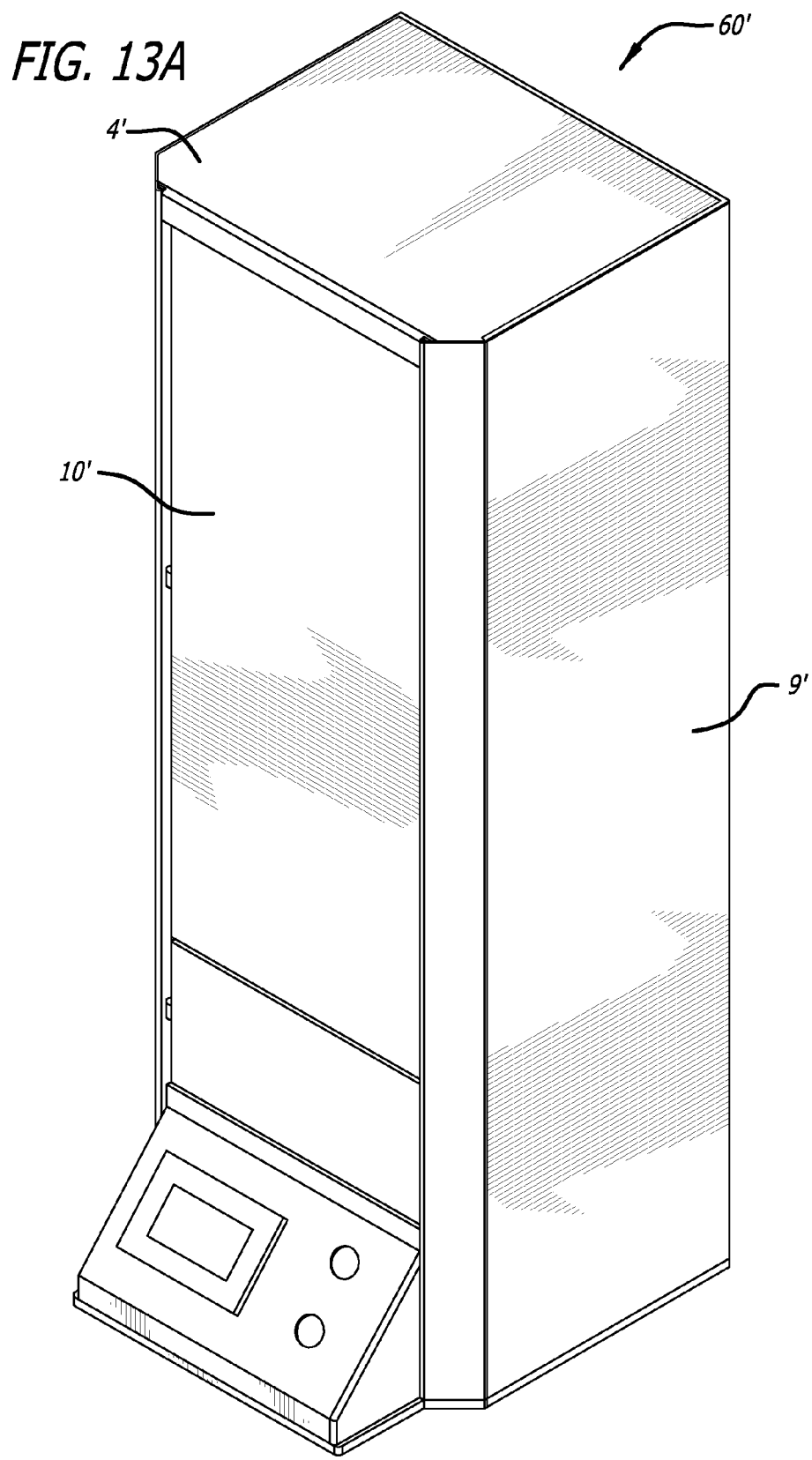
FIG. 13A shows a perspective view of the auto eject housing unit.
Figure 13B:
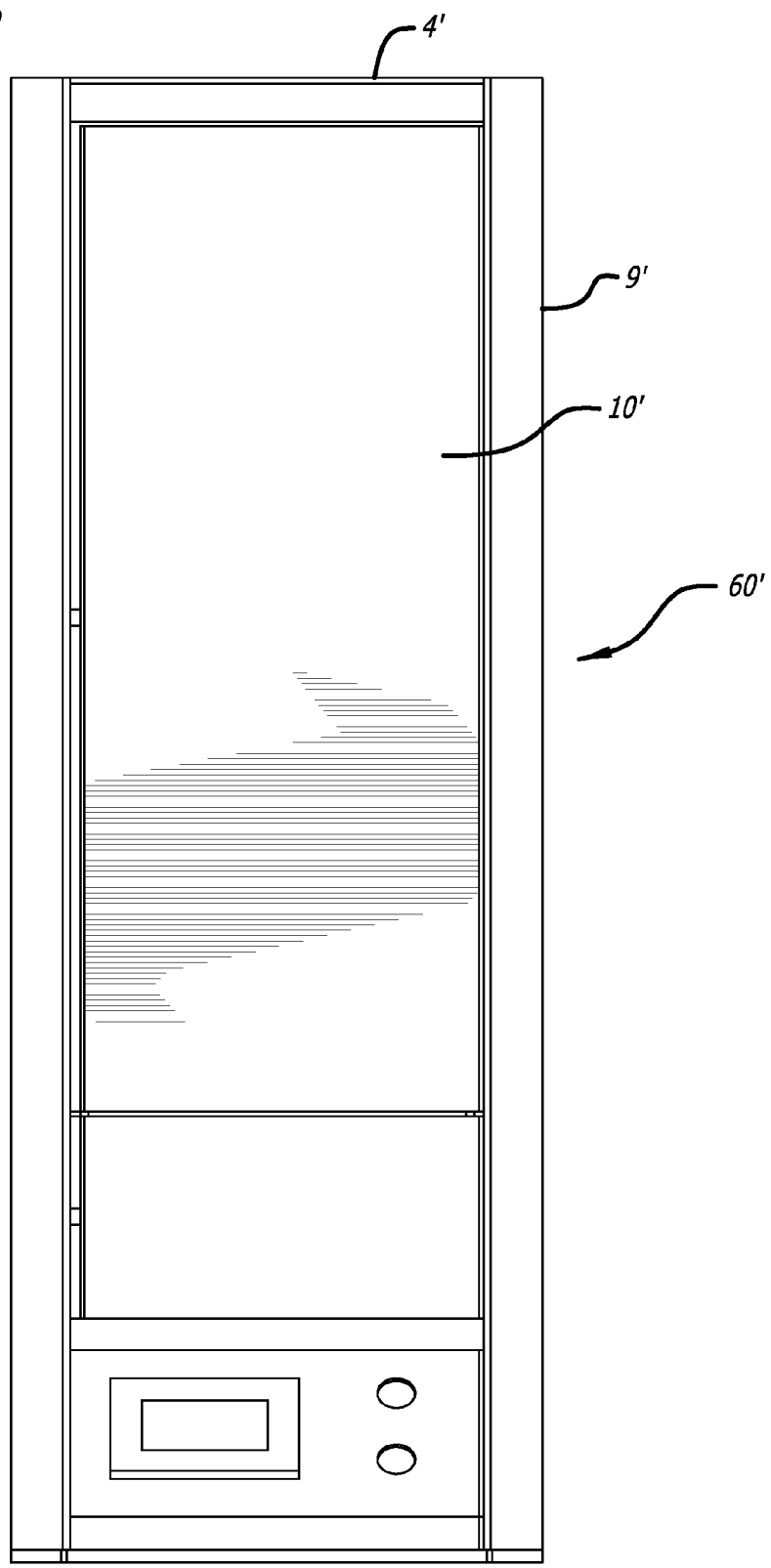
FIG. 13B shows a front view of the auto eject housing unit.
Figure 13C:
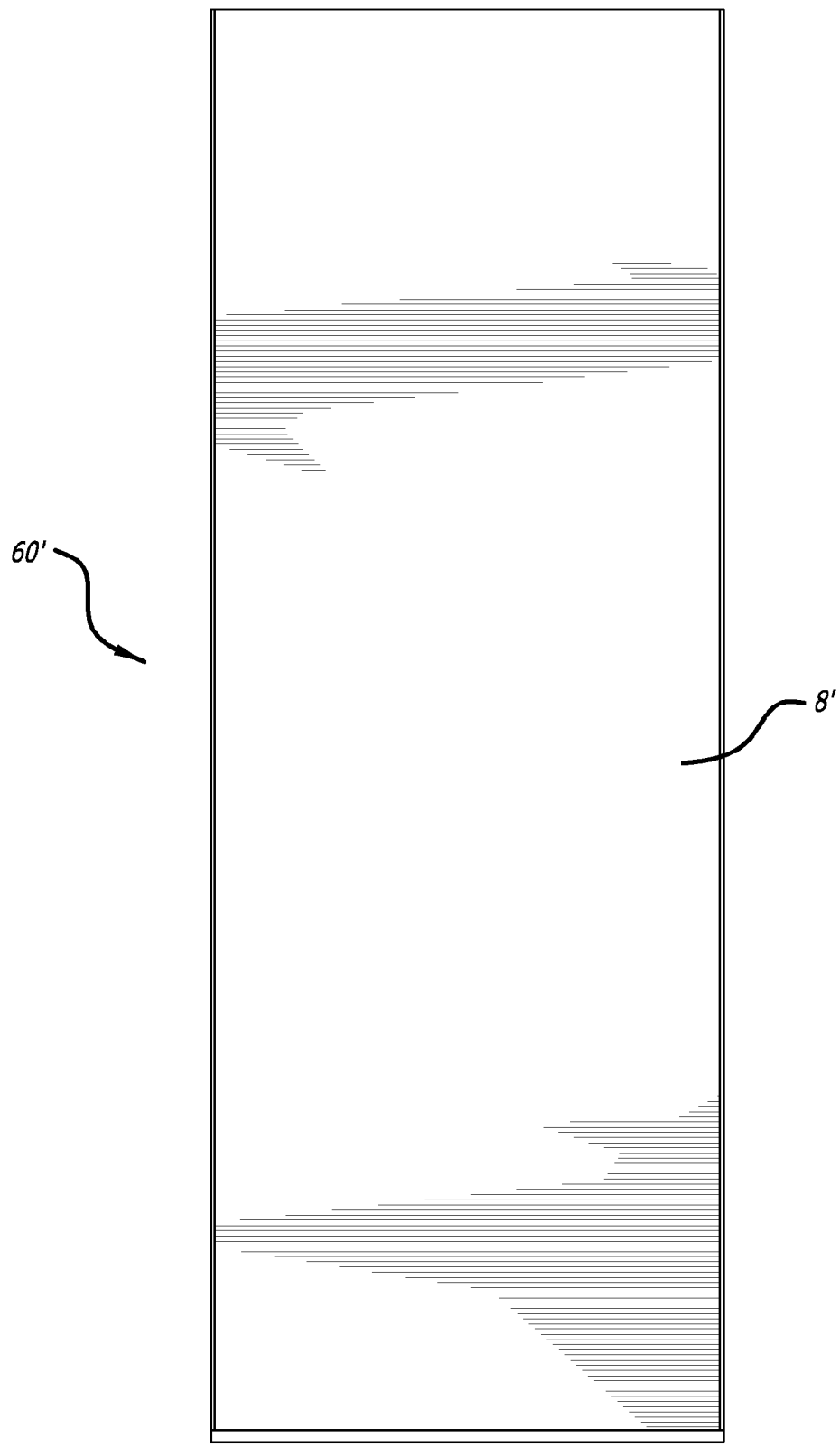
FIG. 13C shows a rear view of the auto eject housing unit.
Figure 13D:
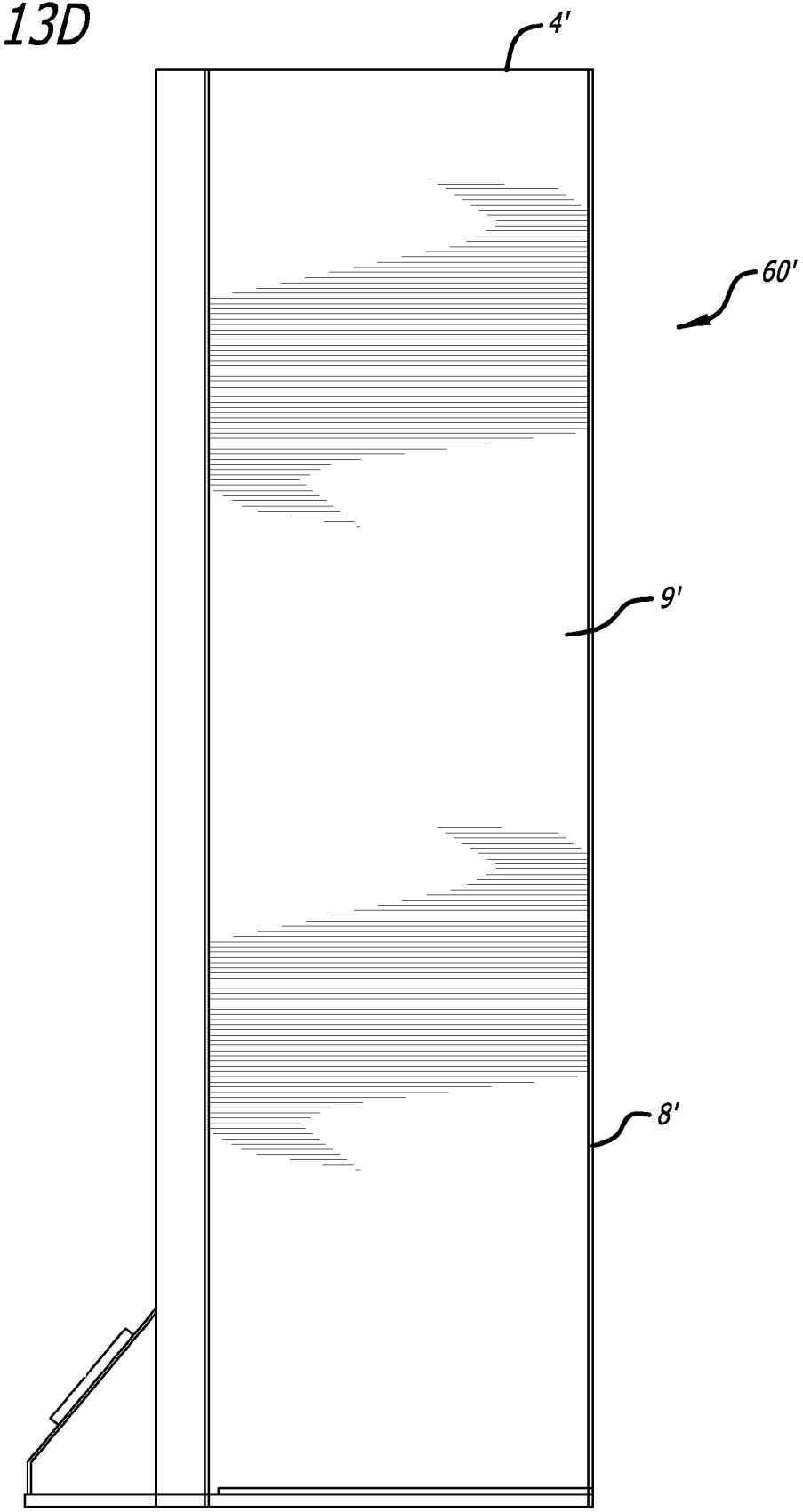
FIG. 13D shows a right side view of the auto eject housing unit.
Figure 13E:
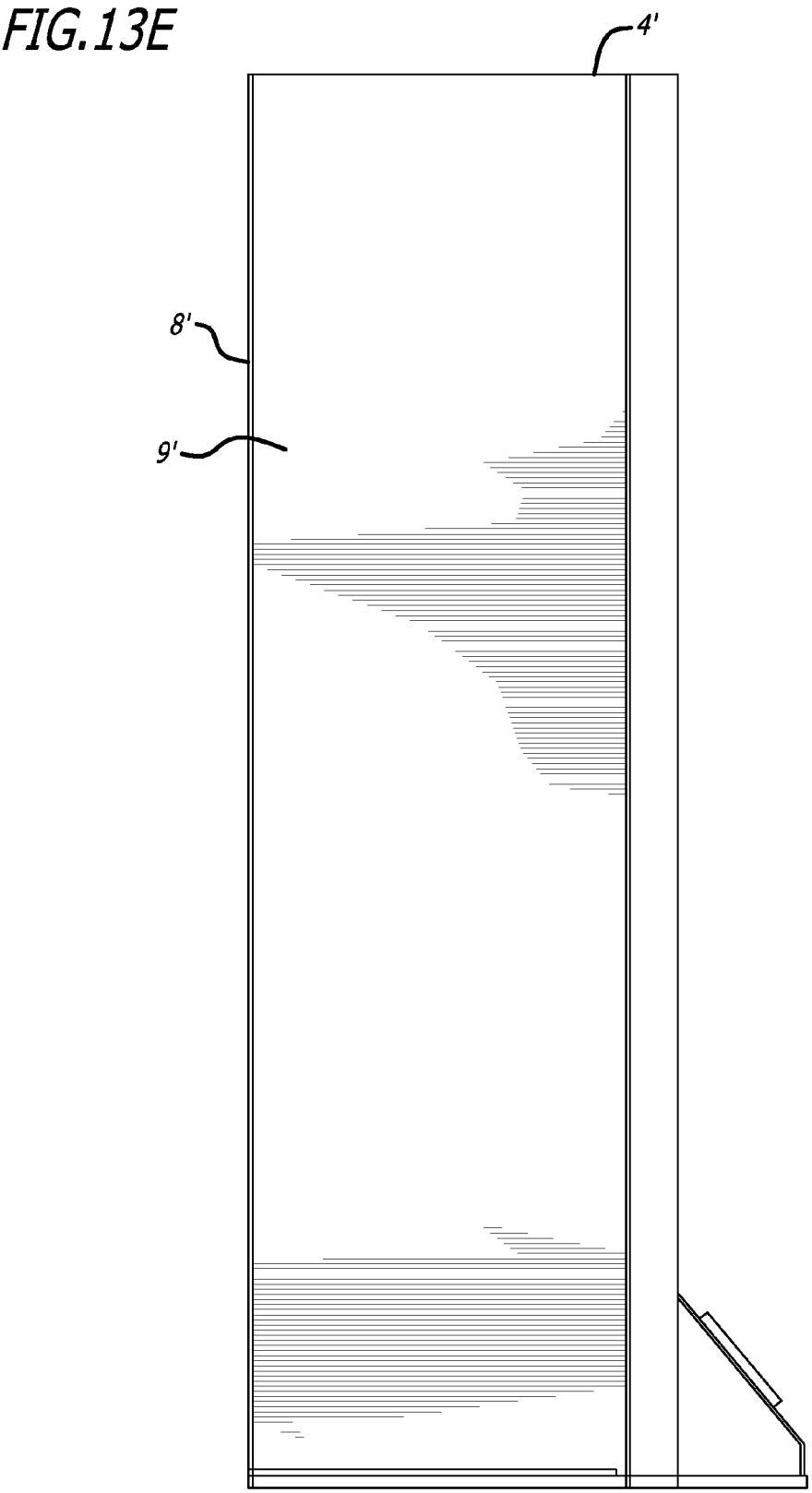
FIG. 13E shows a left side view of the auto eject housing unit.
Figure 13F:
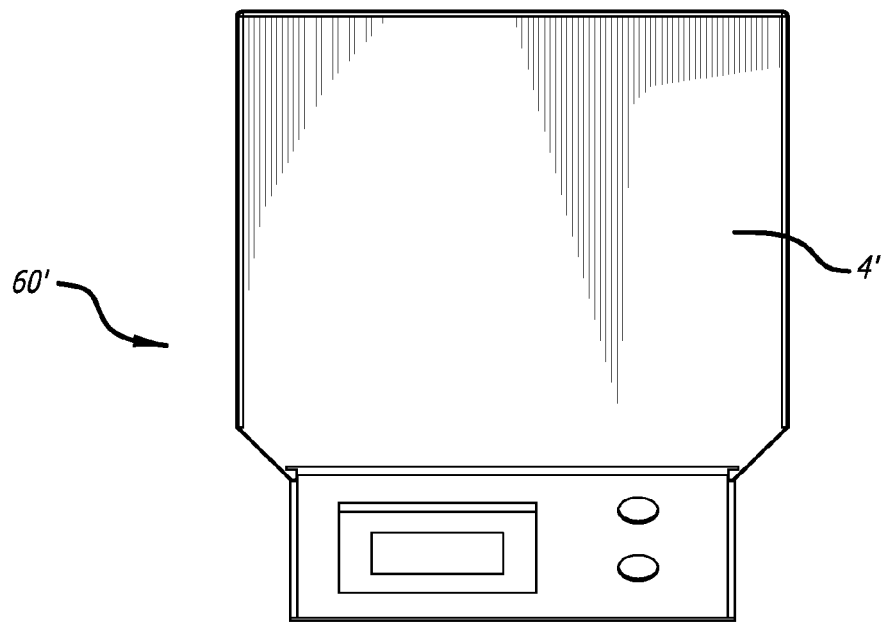
FIG. 13F shows a top view of the auto eject housing unit.
Figure 13G:
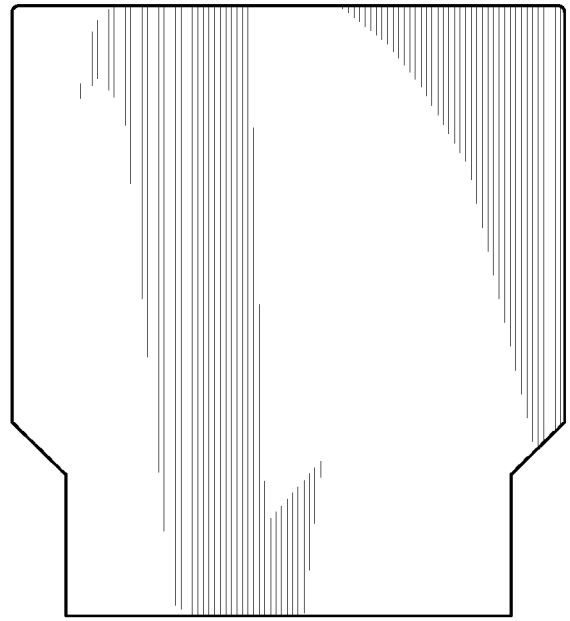
FIG. 13G shows a bottom view of the auto eject housing unit.
Figure 14B:
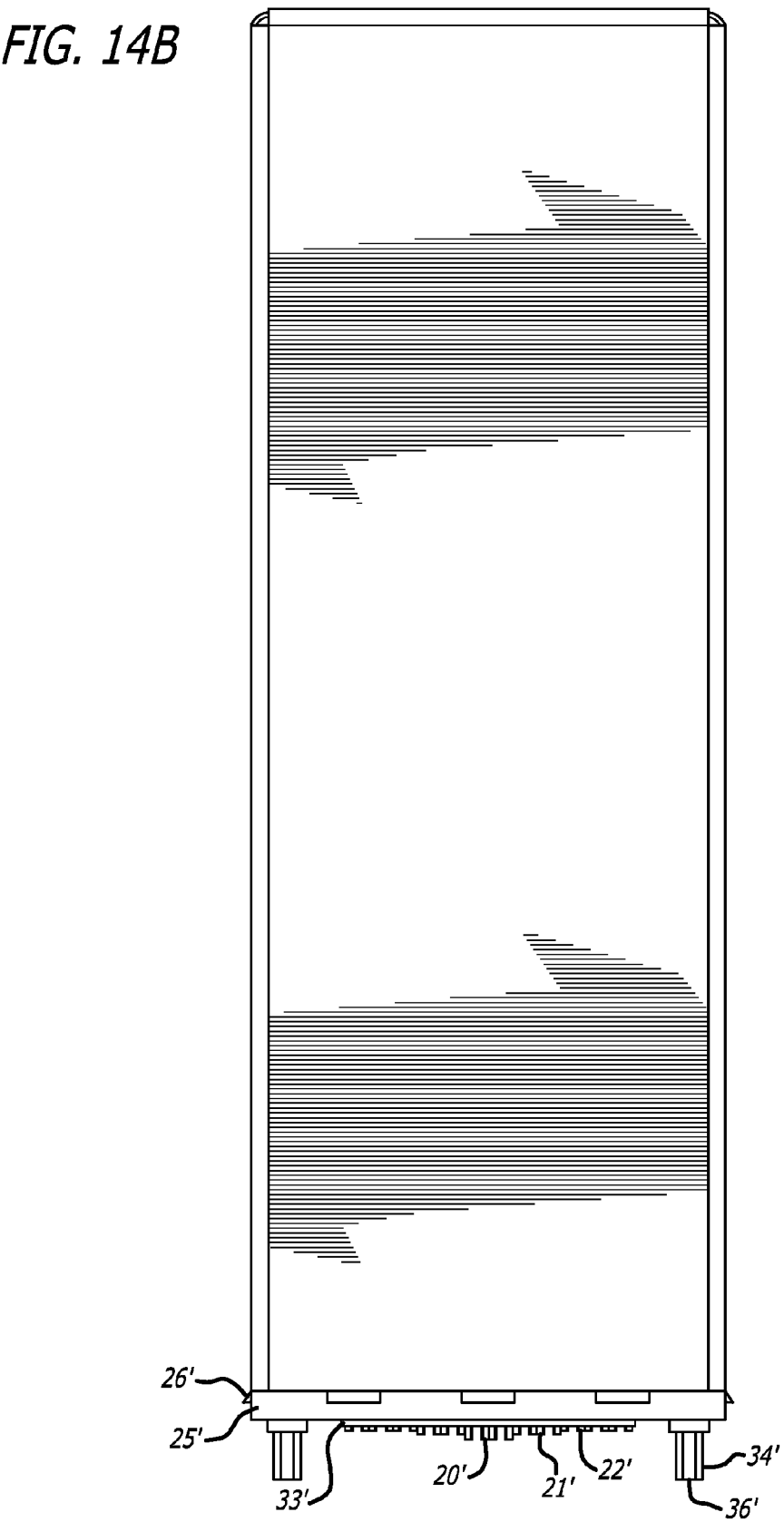
Figure 14C:
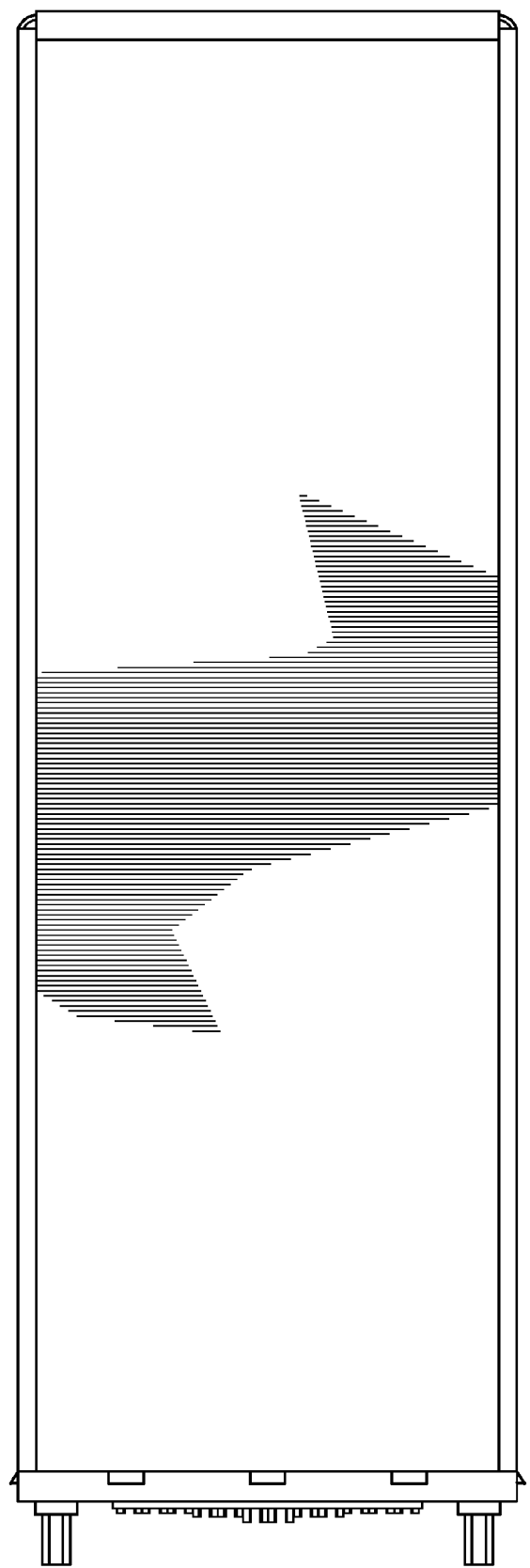
Figure 14F:
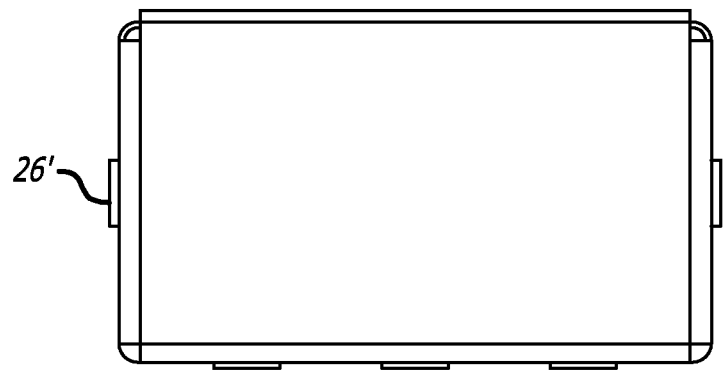
Figure 14G:
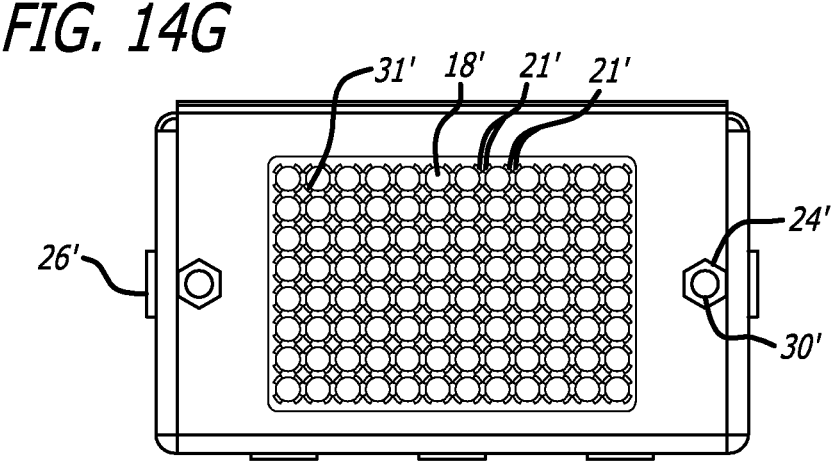

The term "sleeve" as used herein refers to a structure around plates and pipette tips of a cartridge. The sleeve is of any convenient shape for use with a pipette tip dispenser, and sometimes has a circle, oval, square, rectangle, rhombus, parallelogram and the like cross section, and sometimes a sleeve includes one or more surfaces that are planar, non-planar, curved, arced and the like. A sleeve sometimes includes four vertical sides, and sometimes includes a top. A sleeve comprises any suitable materials, and comprises in some embodiments, a polymer, biodegradable polymer, other degradable or biodegradable materials (e.g., bamboo, recycled banana peel, and the like), fiber product, paper, metal and the like, or a combination thereof. The material from which the sleeve is made can be of any suitable color or transparency. In some embodiments, the sleeve may be transparent. In certain embodiments, the sleeve can be semi-transparent. In some embodiments, the sleeve can be opaque. In certain embodiments, a sleeve can be semi-opaque. Opaque sleeves can be of any desired color, in certain embodiments. In some embodiments, the sleeve can be opaque in some regions and transparent in some regions. In certain embodiments, a sleeve can be translucent. In some embodiments, the sleeve comprises writing, and in certain embodiments the sleeve does not comprise writing. A cartridge with a transparent sleeve is illustrated in FIGS. 12-12H. A cartridge with an opaque sleeve is illustrated in FIGS. 14A-14G. The sleeve also may be optional.

Figure 9B:
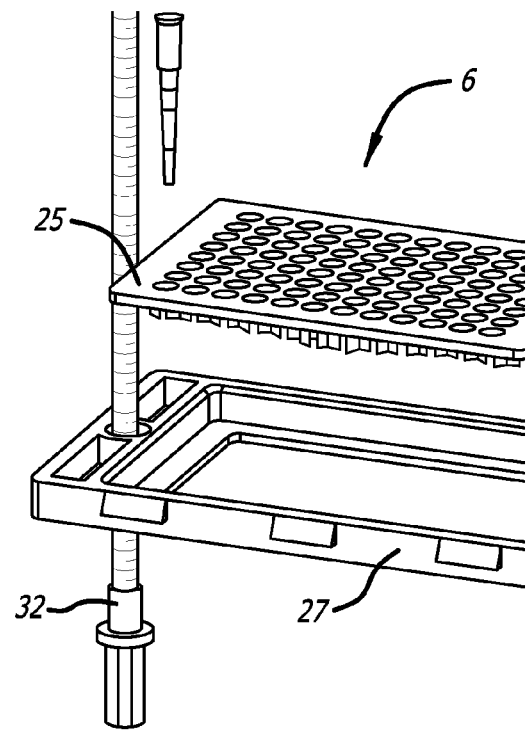
Figure 9C:
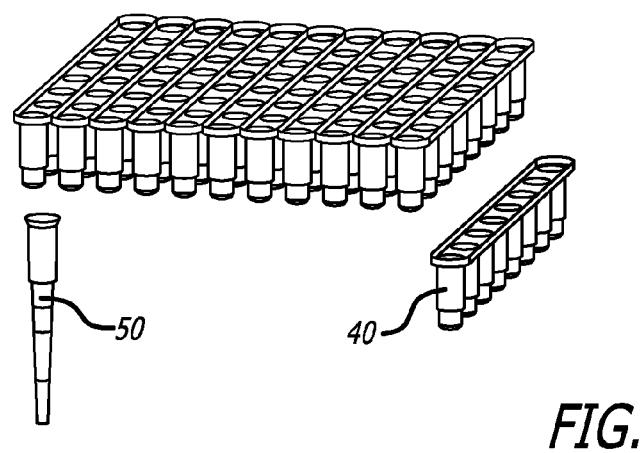

FIG. 9A (see also FIGS. 12A-12C) shows components in an auto eject cartridge with FIG. 9B showing an enlarged detail figure of the distal barrier plate 25, base plate 27, rod with grommet 32. FIG. 9C shows an enlarged detail figure of a plurality of proximal alignment members 40 and placement of one pipette tip 50 underneath.

FIG. 12H illustrates a cartridge with a transparent outer sleeve loaded with a nested array of regularly spaced pipette tips between a top activator plate and a bottom distal barrier plate. Pipette tips can be seen protruding below the distal barrier plate in FIG. 12H.

Housing Unit

Referring to FIGS. 8A-8B (see also FIGS. 13A-E), an automated pipette tip dispensing device is shown in detail. The structural housing components top 4, back 8, side 9, door 10 may be made from any type of material known to one of skill in the art, such as for example a clear, thin rigid material formed into a substantially rectangular configuration with a closed bottom portion such as a base plate and driver 1. The housing unit 60 substantially has planar back 8, sides 9, and door 10 components that may be arranged substantially perpendicular to each other and to the top surface 4 disposed on the upper end of the housing. For some embodiments, the housing may be made from a thin clear polymer material that is transparent or translucent and may have a thickness of about 0.005 inches to about 0.05 inches. For some embodiments, the housing may be made from suitable metals, such as aluminum or steel, or polymers such as polypropylene, polycarbonate, polyethylene, polystyrene, polyurethane and the like as well as any other suitable polymers that may be molded, thermoformed or the like. The housing may have a thickness that allows for some flexibility but provides sufficient structural strength to maintain its general shape upon manual manipulation, e.g., loading and unloading the auto eject cartridge, and automatic dispensing. The housing is also sufficiently rigid to be self-supporting and maintains integrity sufficient to support the full procedure of the automated pipette tip dispensing device. The procedure involves steps such as having a full auto eject cartridge 6 being placed within the housing, automated dispensing of the pipette tips 50 into the loading device 7. After a cartridge 6 is emptied, it can be removed from the housing unit 60, and replaced with a full cartridge 6.

In some embodiments, other housing components can include t-slot posts 2 which provide support as an inner frame for the housing unit. The posts 2 may also be optional, where the planar back 8, sides 9 and door 10 of the housing unit 60 may provide the structure for the housing without the posts 2. Vertical rails or tracks can facilitate placement and/or movement of components within the device, for example such as guide posts 16, see FIG. 8A. The guides 16 can provide alignment so that the moving plate 3 is raised and lowered to the correct positions within the device. The guides 16 may function manually or with a motor. Other components may also provide the same function as the guide posts 16, such as a lever or pulley that raises and lowers the moving plate 3 into position below the distal barrier plate 25. Posts, rails and tracks can be of any suitable geometry for vertically translating plates in an automated dispensing unit. The moving plate 3 is shown having two holes where the guides 16 pass through. One or more guides 16 can be included in the device for this function. The moving plate 3 may function by use of a motor 13 or electrical engine (see FIGS. 15 and 16) and functions to move the loading block 7 up and down in some embodiments, and sometimes a user can operate a lever that manually moves the loading block up and/or down. A user can place an empty loading block 7 onto the lowered moving plate 3. Upon activation the moving plate 3 transports the loading block 7 up and directly beneath the center plate 5 which holds the auto eject cartridge 6 in place in some embodiments. The proximity of the moving plate 3 to the center plate 5 aids in aligning the pipette tips into the loading block 7 before ejection into the block 7. And when the moving plate 3 and loading block 7 are most distal to the center plate 5 or resting above the base plate 1, the space between the loading block 7 and the center plate 5 allows for the user to remove the loading block and/or replace it with another block. Alternatively, the moving plate 3 can be optional, for example, the loading block 7 can be placed on the base plate 1 which can be directly distal to the center plate 5. The base plate 1 can provide a platform for the moving plate 3 and loading block 7 as well as an area for the controller 15 and motor 13 to be housed. However, the controller 15 and/or motor 13 may be housed in another area or areas of the housing unit. There also may be one or more motors 13, for example, one for powering the rods 28 in the cartridge 6 and another motor for powering the moving plate 3 and/or guide posts 16. Alternatively, there may be one motor 13 powering all electric functions including for example, an ionizer, UV light source, or other structure that can sterilize pipette tips. A device can include one or more sterilization components (e.g., UV light emitter, ionizer unit, gamma irradiation unit, sterilizing gas emitter, the like and combinations thereof). In some embodiments, sterilization components can be actuated by a user controlled mechanism, or by an automated mechanism that acts in conjunction with or whose action is initiated by movement of a device component or the action of a controller (e.g., controller 15). Sterilization can occur during the tip dispensing cycle or after the tips are dispensed into the waiting pipette tip rack, while the rack is still positioned on the platform occupying drive system cutout 80.

The controller 15 can centrally coordinate different functions occurring within the device, such as UV light emitter 11, ionizer 12, limit switch 14, etc. and have a user friendly display for adjusting settings and/or keeping track of how many pipette tip arrays are remaining in the auto eject cartridge 6 and/or when a new cartridge needs to be exchanged for an empty one and/or the type of pipette tips being housed in the device as well as specifications for the pipette tips themselves. The controller 15 may also provide a digital time/date and or history log of types of pipette tips used within the device as well as how many cartridges 6 have been used within a give time or history. Such inventory may be useful for budgeting purposes. The controller 15 may aid in a variety of other such user friendly support as well as coordinate other functioning mechanisms within the housing unit. The limit switch 14 can allow for one array of pipette tips to be ejected from the auto eject cartridge 6 per loading block 7. The limit switch 14 can also allow for more than one array of pipette tips to be ejected. The limit switch 14 can be performed by any variety of mechanisms necessary for this function. For example, the limit switch 14 can be a pressure sensor that stops the motor 13 powering the rods 28 from rotating and thereby stopping the activator plate 41 and the distal barrier plate 25 from translating towards one another. The limit switch 14 may function when a specific pressure is sensed on the loading block 7, rods 28, base plate 27, distal barrier plate 25, actuator plate 41, pipette tips 50, moving plate 3, center plate 5, guide posts 16 or any other component.

The limit switch 41 may also be a motion sensor that can allow one array of pipette tips to be ejected from the auto eject cartridge 6 per loading block 7 by sensing the ejection of tips as movement and thereby stop power to the motor 13.

The housing unit 60 may also support other devices for example such as voice activated power controls, lighting, automated locks and releases, audio sounds such as a chime or an audio narrative for the various functions occurring within the device and/or when the pipette tips have been loaded and are ready for use.

Pipette Tip Sterilization

Pipette tip sterilization ensures that living microorganisms (e.g., pathogenic or saprophytic bacteria, vegetative forms and spores or any unwanted organisms) are eliminated (e.g., partially eliminated or substantially eliminated) from pipette tips. Sterilization can be performed in any variety of methods. For example, sterilization can be performed by sterilizing gas treatment, UV irradiation, ionization, alcohol or gamma radiation. FIG. 8A shows a UV light 12 beneath the auto eject cartridge. UV light can bathe the array of pipette tips hanging down from the auto eject cartridge before, during and after ejection into the loading block 7. Any controller mechanism can activate a UV light source, such a motion sensor that detects movement of a loading block into the housing, a switch that is tripped by the pipette tip loading block, or a manual switch used by the operator, for example. The UV light source may work in conjunction with the motor 13 of the device and be activated when the loading block is lifted by the moving plate 3 into position underneath the center plate 5 in some embodiments.

Electrically Conductive Member(s)

Static charge can develop on pipette tips during use or shipping. This static charge can remain on the tips as they reside in dispensers or trays because there often is no flow or discharge of the electric charge from the tips to a ground source. Static charge in/on the tips and other components of a tray or dispenser may cause some of the tips to repel away from each other and other tray or dispenser components. This repulsion can result in the tips arranged in a different orientation than intended, and can negatively impact interaction with pipette devices (e.g., automated dispensers).

Pipette tips often are jostled within their pipette tip trays during shipment. The rubbing of the tips within the apertures of the perforated card that contains them can cause an electrostatic charge to develop on the exterior of the tips. This phenomenon often is applicable to tips of a smaller size (e.g., pipette tips that fit in 384 tip trays). The static charge can remain on the tips as they sit within their trays because there is no flow of the electric charge from the tips to the tip rack. The static charges on the tips and other components of the tray may cause some of the tips to repel away from each other and other tray components. This repulsion can result in the tips arranged in a different orientation than intended, and can negatively impact interaction with pipette devices (e.g., automated dispensers).

In certain embodiments, the pipette tips are in contact with an electrically conductive member, or portions thereof, which is in communication with the exterior of the sleeve and/or housing unit. This contact may allow static charge from the pipette tips to be discharged. Often the contact of an electrically conductive member or portions thereof, with the pipette tips involves the top proximal edges of the tips, which may involve direct, indirect, and/or in effective communication with the inner portion of the lid. The contact may also sometimes involve contact of the sides of the tips which may be in direct, indirect, and/or in effective communication with the card of the tray. In some embodiments, an electrically conductive member, or portions thereof, is in direct, indirect, and/or in effective communication with the pipette tips which ultimately aids in discharging the static charge within the pipette tips. The electrically conductive member, or portions thereof, may be in effective communication with any components of the device and be in effective communication with the exterior of the sleeve and/or housing. In certain embodiments, an electrically conductive member, or portions thereof, is located in any of the components of the device such as for example, the sleeve, housing, activator plate, distal barrier plate, channels, tails, and the like, which is in effective communication with the pipette tips, and is exposed through the sleeve and/or housing.

An electrically conductive member may comprise any type of electrically conductive material known, such as a conductive metal, for example. Examples of conductive metals include, without limitation, platinum (Pt), palladium (Pd), copper (Cu), nickel (Ni), silver (Ag) and gold (Au). The metals may be in any form in or on the conductive member, for example, such as metal flakes, metal powder, metal strands or coating of metal. An electrically conductive member, or portions thereof, may comprise a metal, polymeric material, foam, film, sheet, foil, salt or combinations thereof. In some embodiments, a conductive metal foil may be utilized for one or more components of a pipette tip device (e.g., copper-aluminum foil; label adhered to an electrically conductive tab on exterior of the housing or sleeve component). The electrically conductive materials, or portions thereof, may be any material that can contain movable electric charges, for example such as carbon. In some embodiments, the electrically conductive member comprises about 5% to about 40% or more carbon by weight (e.g., 7-10%, 9-12%, 11-14%, 13-16%, 15-18%, 17-20%, 19-22%, 21-24%, 23-26%, 25-28%, 27-30%, 29-32%, 32-34%, 33-36%, or 35-38% carbon by weight). In certain embodiments, an electrically conductive film is utilized that includes carbon (e.g., commercially available from Gemini Plastic Enterprises, Inc., California). An electrically conductive film in some embodiments contains ethylene vinyl acetate (EVA), which can impart a supple quality to the film (e.g., about 5% to about 25% EVA by weight; about 6, 7, 8, 9, 10, 11, 12, 13, 14, 15, 16, 17, 18, 19, 20, 21, 22, 23, 24% EVA). In some embodiments a conductive tab may be in effective communication with any one or combination or all of the components of the device and aid in discharging an electrical charge from the device. A tab often is in effective communication with a conductive material contacting the pipette tips and the exterior of the device (e.g., exterior surface of the housing or sleeve). The tab may be affixed to one or more portions of a device (e.g., by an electrically conductive label).

The term "effective communication" as used herein refers to direct (e.g., part of the conductive member) or indirect (e.g., via component not part of the conductive member) in communication with exterior of the housing and/or sleeve. The term "exposure of conductive member" as used herein may refer to exposure by a reveal in a plate or member which may extend to the sleeve and/or housing exterior or can be free hanging or may be affixed to an external surface of the sleeve, housing and/or loading block. The external surfaces of the housing are for example the roof or sides of the housing. The term "affixed" as used herein refer to attachment for example such as embossed or adhesive.

A component that dissipates electrostatic charge from the pipette tips, such as an ionizer or humidifier, may be included in the device. An ionizer 12, as depicted in FIGS. 8A and 8B, blows, directs and/or circulates an amount of ionized air towards the pipette tips 50 and loading block 7 that reduces or substantially eliminates any existing or potential build up of electrostatic charge on the tips. One of ordinary skill in the art will recognize various ways to activate such a device. Any controller mechanism can activate the ionizer, such as for example a motion sensor that detects movement of a loading block into the housing or a manual switch used by the operator. Or the ionizer may work in conjunction with the motor 13 of the device and be activated when the loading block is lifted by the moving plate 3 into position underneath the center plate 5.

Components described herein reduce the potential for static build-up and/or provide an alternate grounding path for harmlessly dissipating built-up electrostatic charge, or for discharging an electrostatic charge well before a substantial amount of charge may build up.

Method of Use

A pipette tip dispensing device described here can be used in conjunction with a method of simultaneously dispensing an array of multiple pipette tips into a loading block. In some embodiments, methods include: providing a dispensing device that includes a nested array of regularly spaced pipette tips between a top activator plate and a bottom distal barrier plate, wherein the activator plate and the distal barrier plate are in connection with two or more rods, wherein the distal barrier plate comprises: a plurality of channels, wherein each channel has a diameter larger than the widest portion of a pipette tip; a substantially flat top surface, and a substantially flat bottom surface that comprises a plurality of tails around some or all of the channels, wherein the tails extend in a nearly perpendicular orientation from the flat bottom surface; and actuating a motor of the dispensing device in effective connection with the rods that moves the rods, whereby the activator plate and the distal barrier plate are translated towards one another thereby applying an axial force on the array of pipette tips, wherein: (i) the axial force dispenses the array of pipette tips through the channels and past the tails, and (ii) the tails contact and deflect outwards against the pipette tips and impart a frictional force on the pipette tips, whereby the array of pipette tips is ejected into respective receptacles in the loading block. In certain embodiments, a pipette tip rack is loaded into the pipette tip dispenser housing unit, seated on the pipette tip rack holding platform in an appropriate location to receive pipette tips from the dispense, prior to activation of the pipette tip dispensing mechanism. In some embodiments, the pipette tip rack can be seated on the holding platform using manual loading methods, and in certain embodiments, the pipette rack can be seated on the holding platform using automated loading methods, prior to dispensing pipette tips into the pipette tip rack.

EXAMPLES

Provided hereafter are non-limiting examples of certain embodiments.

1. A pipette tip dispensing device, comprising:
a) a sleeve;
b) an activator plate within the sleeve;
c) a distal barrier plate within the sleeve disposed opposite to and spaced away from the activator plate;
d) two or more connectors in connection with the activator plate and distal barrier plate;
e) a plurality of nested pipette tip units between the activator and barrier plates, wherein: (i) each unit is aligned with a channel in the distal barrier plate, and (ii) the distal barrier plate comprises:
   a plurality of channels, wherein each channel has a diameter larger than the widest portion of a pipette tip;

a substantially flat top surface, and a substantially flat bottom surface that comprises a plurality of tails around some or all of the channels, wherein the tails extend in a nearly perpendicular orientation from the flat bottom surface, wherein the tails around each channel contact and deflect outwards against the proximal portion of a pipette tip when a pipette tip is dispensed and passes by the tails, thereby imparting a frictional force on the pipette tip when it is dispensed.

2. The pipette tip dispensing device of embodiment 1, wherein each channel comprises 2, 3, 4, 5, 6, 7, 8, 9, 10 or more tails.

2.1. The pipette tip dispensing device of embodiment 1 or 2, wherein a subset of channels in the distal barrier plate are surrounded by tails that eject pipette tips of an array at one time, and another subset of channels in the plate are surrounded by tails that eject pipette tips of the same array at another time.

2.2. The pipette tip dispensing device of embodiment 2.1, wherein:

the distal barrier plate comprises 2, 3, 4, 5, 6, 7, 8, 9, 10, 11, 12, 13, 14, 15, 16, 17, 18, 19 or 20 of different subsets of channels, and each subset ejects pipette tips of one array at different times.

3. The pipette tip dispensing device of any one of claims 1-2.2, wherein each channel of the barrier plate comprises tails of the same length.

4. The pipette tip dispensing device of any one of embodiments 1-2.2, wherein each channel of the barrier plate comprises tails of different lengths.

5. The pipette tip dispensing device of embodiment 4, wherein channels located in the center of the barrier plate comprise the longest tails.

6. The pipette tip dispensing device of embodiment 4, wherein channels located in the center of the barrier plate comprise the shortest tails.

7. The pipette tip dispensing device of embodiment 5, wherein subsequent channels concentrically disposed about a central longitudinal axis comprise sequentially shorter tails in length in a stepwise manner.

8. The pipette tip dispensing device of embodiment 6, wherein subsequent channels concentrically disposed about a central longitudinal axis comprise sequentially longer tails in length in a stepwise manner.

9. The pipette tip dispensing device of any one of embodiments 1-8, wherein channels located in the center of the barrier plate along the X axis comprise tails of the same length and channels along the Y axis comprise tails of varying length.

10. The pipette tip dispensing device of any one of embodiments 1-8, wherein channels located in the center of the barrier plate along the Y axis comprise tails of the same length and channels along the X axis comprise tails of varying length.

11. The pipette tip dispensing device of any one of embodiments 1-8, wherein channels located in the center of the barrier plate along the X and Y axes comprise tails of varying length.

12. The pipette tip dispensing device of any one of embodiments 1-8, wherein each channel comprises an even number of tails.

13. The pipette tip dispensing device of embodiment 12, wherein tails directly opposite one another around a channel have the same length.

14. The pipette tip dispensing device of embodiment 12, wherein tails directly opposite one another around a channel have a different length.

15. The pipette tip dispensing device of embodiment 12 or 13, wherein tails adjacent to one another have a different length.

16. The pipette tip dispensing device of any one of embodiments 1-15, wherein the tails are at an internal angle of about 89° to about 80° from the bottom surface of the distal barrier plate.

17. The pipette tip dispensing device of embodiment 16, wherein the tails are at an internal angle between 88-85°, 87-84°, 86-83° or 86-85° from the bottom surface of the distal barrier plate.

18. The pipette tip dispensing device of embodiment 16, wherein the tails are at an internal angle of about 87° from the bottom surface of the distal barrier plate.

19. The pipette tip dispensing device of any one of embodiments 1-18, wherein the tails are between 0.01 μm-2.0 mm in length.

20. The pipette tip dispensing device of embodiment 1, wherein the tails are between 0.05 μm-2.0 mm in length.

21. The pipette tip dispensing device of embodiment 1, wherein the tails around a channel are not in the channel.

22. The pipette tip dispensing device of embodiment 1, wherein the activator plate, distal barrier plate, connectors, and plurality of pipette tips are located in the sleeve.

22.1. The pipette tip dispensing device of embodiment 1, wherein the sleeve further comprises a top portion, four sides and a bottom lid.

22.2. The pipette tip dispensing device of embodiment 22.1, wherein the sleeve is comprised of one or more of a polymer material, chipboard, glass, Styrofoam, wood, metal, plastic, paper, or combination thereof.

23. The pipette tip dispensing device of embodiment 1, wherein the activator plate, distal barrier plate, connectors, plurality of pipette tips and sleeve are located inside a sleeve unit.

23.1 The pipette tip dispensing device of any one of the preceding embodiments, which is in association with a housing unit.

23.2. The pipette tip dispensing device of embodiment 23.1, wherein the housing unit further comprises a movable bottom platform that positions a loading block directly distal to the barrier plate to receive an ejected array of pipette tips from the dispensing device.

24. The pipette tip dispensing device of embodiment 23, wherein the housing unit comprises a polymer material.

25. The pipette tip dispensing device of embodiment 24, wherein the polymer material of the housing unit comprises molded polypropylene.

26. The pipette tip dispensing device of embodiment 25, wherein the polymer material of the housing unit comprises a thickness of about 0.005 inches to about 0.05 inches.

27. The pipette tip dispensing device of embodiment 1, wherein the activator plate comprises material on the top portion of the plate that maintains contact with and restricts lateral displacement of the proximal portion of the pipette tips.

28. The pipette tip dispensing device of embodiment 27, wherein the material is selected from the group consisting of foam, a raised grid, and a plurality of proximal alignment members.

29. The pipette tip dispensing device of embodiment 1, wherein the activator plate comprises a polymer material.

30. The pipette tip dispensing device of embodiment 29, wherein the polymer material of the activator plate comprises molded polypropylene.

31. The pipette tip dispensing device of embodiment 30, wherein the polymer material of the activator plate comprises a thickness of about 0.30 inches to about 0.65 inches.

31.1. The pipette tip dispensing device of embodiment 1, wherein the activator plate comprises a top portion and a roof portion.

32. The pipette tip dispensing device of embodiment 31.1, wherein the polymer material is molded with raised ridges on the top portion and the roof portion.

33. The pipette tip dispensing device of embodiment 1, wherein the distal barrier plate further comprises one or more fasteners along one or more of its vertical lateral sides configured to connect with the sleeve.

34. The pipette tip dispensing device of embodiment 1, wherein the pipette tip unit comprises 96, 384, or more numbers of pipette tips.

35. The pipette tip dispensing device of embodiment 1, wherein the pipette tip unit is arranged in an array of pipette tip units.

36. The pipette tip dispensing device of embodiment 1, wherein each nested pipette tip unit comprises 2, 3, 4, 5, 6, 7, 8, 9, 10, 11, 12, 13, 14, 15, 16, 17 or more pipette tips.

37. The pipette tip dispensing device of embodiment 1, wherein the connectors are rods.

37.1. The pipette tip dispensing device of embodiment 37, wherein the rods in connection with the activator plate and the distal barrier plate comprises threads.

38. The pipette tip dispensing device of embodiment 37.1, wherein the activator plate the distal barrier plate are translated towards one another by rotation of the rods.

38.1. The pipette tip dispensing device of embodiment 38, wherein the activator plate comprises threaded members, and each threaded member engages a threaded portion of each rod, whereby the activator plate translates towards the distal barrier plate by rotation of the rods.

39. The pipette tip dispensing device of embodiment 38, wherein the rods are rotated by a motor.

40. The pipette tip dispensing device of embodiment 39, wherein the motor is activated by a user controlled mechanism.

41. The pipette tip dispensing device of embodiment 40, wherein the user controlled mechanism is a lever switch, button, or sensor.

42. The pipette tip dispensing device of embodiment 39, wherein the motor stops rotating the rods by a pressure sensor gauge.

43. The pipette tip dispensing device of embodiment 35, wherein the pipette tips that have passed through the distal barrier plate are sterilized.

44. The pipette tip dispensing device of embodiment 43, wherein sterilization is by UV irradiation, ionization, alcohol or gamma radiation.

45. A method of simultaneously dispensing an array of multiple pipette tips into a loading block, comprising:
providing a dispensing device that includes a nested array of regularly spaced pipette tips between a top activator plate and a bottom distal barrier plate, wherein the activator plate and the distal barrier plate are in connection with two or more rods, wherein the distal barrier plate comprises:
    a plurality of channels, wherein each channel has a diameter larger than the widest portion of a pipette tip;
    a substantially flat top surface, and
    a substantially flat bottom surface that comprises a plurality of tails around some or all of the channels, wherein the tails extend in a nearly perpendicular orientation from the flat bottom surface; and
actuating a motor of the dispensing device in effective connection with the rods that moves the rods, whereby the activator plate and the distal barrier plate are translated towards one another thereby applying an axial force on the array of pipette tips, wherein: (i) the axial force dispenses the array of pipette tips through the channels and past the tails, and (ii) the tails contact and deflect outwards against the pipette tips and impart a frictional force on the pipette tips, whereby the array of pipette tips is ejected into respective receptacles in the loading block.

45.1. The method of embodiment 45, wherein the loading block is loaded prior to activation of the dispensing device.

45.2. The method of embodiment 45, wherein the motor directly or indirectly rotates the rods.

46. The method of embodiment 45, wherein the barrier plate comprises 2, 3, 4, 5, 6, 7, 8, 9, or more tails.

46.1. The pipette tip dispensing device of embodiment 45 or 46, wherein a subset of channels in the distal barrier plate are surrounded by tails that eject pipette tips of an array at one time, and another subset of channels in the plate are surrounded by tails that eject pipette tips of the same array at another time.

46.2. The pipette tip dispensing device of embodiment 46.1, wherein:
    the distal barrier plate comprises 2, 3, 4, 5, 6, 7, 8, 9, 10, 11, 12, 13, 14, 15, 16, 17, 18, 19 or 20 of different subsets of channels, and
    each subset ejects pipette tips of one array at different times.

47. The method of any one of embodiments 45-46.2, wherein each channel of the barrier plate comprises tails of the same length.

48. The method of embodiments 45-46.2, wherein each channel of the barrier plate comprises tails of different lengths.

49. The method of embodiment 48, wherein channels located in the center of the barrier plate comprise the longest tails.

50. The method of embodiment 48, wherein channels located in the center of the barrier plate comprise the shortest tails.

51. The method of embodiment 49, wherein subsequent channels concentrically disposed about a central longitudinal axis comprise sequentially shorter tails in length in a stepwise manner.

52. The method of embodiment 50, wherein subsequent channels concentrically disposed about a central longitudinal axis comprise sequentially longer tails in length in a stepwise manner.

53. The method of any one of embodiments 45-52, wherein channels located in the center of the barrier plate along the X axis comprise tails of the same length and channels along the Y axis comprise tails of varying length.

54. The method of any one of embodiments 45-52, wherein channels located in the center of the barrier plate along the Y axis comprise tails of the same length and channels along the X axis comprise tails of varying length.

55. The method of any one of embodiments 45-52, wherein channels located in the center of the barrier plate along the X and Y axes comprise tails of varying length.

56. The method of any one of embodiments 45-52, wherein each channel comprises an even number of tails.

57 The method of embodiment 56, wherein tails directly opposite one another around a channel have the same length.

58. The method of embodiment 56, wherein tails directly opposite one another around a channel have a different length.

59. The method of embodiment 56 or 57, wherein tails adjacent to one another have a different length.

60 The method of embodiment 45-59, wherein the tails are at an internal angle of about 89° to about 80° from the bottom surface of the distal barrier plate.

61. The method of embodiment 60, wherein the tails are at an internal angle between 88-85°, 87-84°, 86-83° or 86-85° from the bottom surface of the distal barrier plate.

62. The method of embodiment 60, wherein the tails are at an internal angle of about 87° from the bottom surface of the distal barrier plate.

63. The method of embodiment 45-62, wherein the tails are between 0.01 μm-2.0 mm in length.

64. The method of embodiment 45-62, wherein the tails are between 0.05 μm-2.0 mm in length.

65. The method of embodiment 45, wherein the tails around a channel are not in the channel.

66. The method of embodiment 45, wherein the actuating step is repeated by automatic or manual activation until all the nested pipette tips are ejected from the dispensing device.

67. The method of embodiment 66, wherein the automatic activation is performed by a pressure gauge sensor.

68. The method of embodiment 67, wherein the manual activation is performed by a lever switch, button, or sensor.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the claimed technology. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Embodiments of the technology are set forth in the claim(s) that follow(s).

What is claimed is:

1. A pipette tip dispensing device, comprising:
   (a) a sleeve;
   (b) an activator plate within the sleeve;
   (c) a distal barrier plate within the sleeve disposed opposite to and spaced away from the activator plate;
   (d) a plurality of nested pipette tip units between the activator plate and distal barrier plate, each of which nested pipette tip units is aligned with a channel in the distal barrier plate;
   which distal barrier plate comprises: a plurality of channels, each which channels has a diameter larger than the widest portion of a pipette tip; the plurality of channels comprising two or more different subsets of channels and each subset of channels is configured to eject tips at different times; a substantially flat top surface; and a substantially flat bottom surface comprising a plurality of projections around some or all of the channels;
   which plurality of projections around any one subset of channels are the same length and different subsets of channels comprise projections of different lengths.

2. The device of claim 1, which is in association with a housing unit.

3. The device of claim 1, wherein the plurality of nested pipette tip units are arranged as a planar array on the distal barrier plate.

4. The device of claim 3, wherein the array comprises 96, 384 or more pipette tip units.

5. The device of claim 1, wherein each nested pipette tip unit comprises two (2) or more nested pipette tips.

6. The device of claim 1, wherein the plurality of projections around each channel comprises four (4) or more projections.

7. The device of claim 1, wherein the plurality of projections extend in a nearly perpendicular orientation from the flat bottom surface of the distal barrier plate.

8. The device of claim 5, wherein the plurality of projections are at an internal angle of about 89° to about 80° from the bottom surface of the distal barrier plate.

9. The device of claim 1, wherein the plurality of projections around each channel are not in the channel.

10. The device of claim 2, wherein the housing comprises a polymer.

11. The device of claim 10, wherein the polymer comprises molded polypropylene.

12. The device of claim 10, wherein the polymer comprises a thickness of about 0.005 inches to about 0.05 inches.

13. The device of claim 1, wherein the projections are about 0.01 micrometers to about 2.0 millimeters in length.

14. The device of claim 1, wherein channels located in the center of the distal barrier plate comprise projections shorter in length than projections of channels located at the periphery of the distal barrier plate.

15. The device of claim 1, wherein subsequent channels concentrically disposed about a central longitudinal axis comprise sequentially shorter projections in length in a stepwise manner.

16. The device of claim 1, wherein subsequent channels concentrically disposed about a central longitudinal axis comprise sequentially longer projections in length in a stepwise manner.

17. The device of claim 1, wherein the distal barrier plate comprises an X axis and a Y axis, and wherein channels located in the center of the barrier plate along the X axis comprise projections of the same length and channels along the Y axis comprise projections of varying length.

18. The device of claim 1, wherein the distal barrier plate comprises an X axis and a Y axis and wherein channels located in the center of the barrier plate along the Y axis comprise projections of the same length and channels along the X axis comprise projections of varying length.

19. The device of claim 1, wherein the activator plate comprises material on the top portion of the plate that maintains contact with and restricts lateral displacement of the proximal portion of the pipette tips.

20. The pipette tip dispensing device of claim 1, which comprises two or more connectors in connection with the activator plate and distal barrier plate.

21. The device of claim 20, wherein the activator plate, distal barrier plate, connectors, and plurality of pipette tips are located in the sleeve.

22. The pipette tip dispensing device of claim 20, wherein the connectors are rods, which rods are configured to translate the activator plate towards the distal barrier plate upon rotation of the rods.

* * * * *